US010908159B2

(12) United States Patent
Steere et al.

(10) Patent No.: US 10,908,159 B2
(45) Date of Patent: Feb. 2, 2021

(54) IDENTIFICATION OF A T CELL EPITOPE OF *PREVOTELLA COPRI* THAT INDUCES T CELL RESPONSES IN PATIENTS WITH RHEUMATOID ARTHRITIS

(71) Applicant: THE GENERAL HOSPITAL CORPORATION, Boston, MA (US)

(72) Inventors: Allen C. Steere, Wellesley, MA (US); Elise E. Drouin, Boston, MA (US)

(73) Assignee: THE GENERAL HOSPITAL CORPORATION, Boston, MA (US)

( * ) Notice: Subject to any disclaimer, the term of this patent is extended or adjusted under 35 U.S.C. 154(b) by 0 days.

(21) Appl. No.: 16/307,055

(22) PCT Filed: Jun. 6, 2017

(86) PCT No.: PCT/US2017/036198
§ 371 (c)(1),
(2) Date: Dec. 4, 2018

(87) PCT Pub. No.: WO2017/214180
PCT Pub. Date: Dec. 14, 2017

(65) Prior Publication Data
US 2019/0137491 A1 May 9, 2019

Related U.S. Application Data

(60) Provisional application No. 62/346,666, filed on Jun. 7, 2016.

(51) Int. Cl.
*G01N 33/564* (2006.01)
*G01N 33/569* (2006.01)
*G01N 33/68* (2006.01)
*C07K 16/12* (2006.01)
*G01N 33/533* (2006.01)

(52) U.S. Cl.
CPC ....... *G01N 33/564* (2013.01); *C07K 16/1257* (2013.01); *G01N 33/533* (2013.01); *G01N 33/56916* (2013.01); *G01N 33/6878* (2013.01); *C07K 2317/34* (2013.01); *G01N 2469/20* (2013.01); *G01N 2800/102* (2013.01)

(58) Field of Classification Search
None
See application file for complete search history.

(56) References Cited

U.S. PATENT DOCUMENTS

| 4,208,479 | A | 6/1980 | Zuk et al. |
| 5,248,595 | A | 9/1993 | Boyer |
| 2005/0130117 | A1 | 6/2005 | Davis |
| 2006/0094056 | A1 | 5/2006 | Chappell |
| 2007/0148704 | A1 | 6/2007 | Klause |
| 2007/0264673 | A1 | 11/2007 | Wild |
| 2011/0052488 | A1 | 3/2011 | Dennis et al. |
| 2013/0302329 | A1 | 11/2013 | Steere |
| 2015/0010631 | A1 | 1/2015 | Getts |

FOREIGN PATENT DOCUMENTS

| JP | 200512008 A | 9/2000 | |
| WO | 2002/048310 A2 | 6/2002 | |
| WO | 2004/078098 A2 | 9/2004 | |
| WO | 2005/029091 A2 | 3/2005 | |
| WO | 2005/064307 A2 | 7/2005 | |
| WO | 2005/085858 A1 | 9/2005 | |
| WO | 2006/008183 A1 | 1/2006 | |
| WO | 2007/039280 A1 | 4/2007 | |
| WO | 20110052488 A1 | 3/2011 | |
| WO | WO-2013056222 A1 * | 4/2013 | ............. C12Q 1/689 |
| WO | 2017214180 A1 | 12/2017 | |

OTHER PUBLICATIONS

Pianta et al. 2015 (Identification of a Broadly Immunogenic Prevotella copri T Cell Epitope in Patents with Rheumatoid Arthritis; Abstract No. 1930; ACR/ARHP Annual Meeting; Arthritis Rheumatol. 2015: 67 (10)) (Year: 2015).*
Scher et al. 2013 (Expansion of intestinal Prevotella copri correlates with enhanced susceptibility to arthritis; eLife 2013;2:e01202. DOI: 10.7554/eLife.01202; p. 1-20) (Year: 2013).*
Pianta et al. 2015 (Identification of a Broadly Immunogenic Prevotella Copri T-cell epitopein patients with Rheumatoid Arthritis; Abstract No. 1930; T Cell Biology and Targets in Autoimmune Disease Poster session B; ACR/ARHP Annual Meeting; Nov. 9, 2015. (Year: 2015).*
Aletaha et al., "2010 rheumatoid arthritis classification criteria: an American College of Rheumatology/European League Against Rheumatism collaborative initiative", Ann Rheum Dis 69(9) 1580-1588 (2010).
Alvarez-Navarro et al., "Novel HLA-B27-restricted epitopes from Chlamydia trachomatis generated upon endogenous processing of bacterial proteins suggest a role of molecular mimicry in reactive arthritis", J Biol Chem 288(36) 25810-25825 (2013).
Arnett et al., "The American Rheumatism Association 1987 revised criteria for the classification of rheumatoid arthritis", Arthritis Rheum 31(3) 315-324 (1988).
Bassani-Sternberg et al., "Mass spectrometry of human leukocyte antigen class I peptidomes reveals strong effects of protein abundance and turnover on antigen presentation", Mol Cell Proteomics 14(3) 658-673 (2015).

(Continued)

*Primary Examiner* — Mary Maille Lyons
(74) *Attorney, Agent, or Firm* — Nixon Peabody LLP; David S. Resnick

(57) ABSTRACT

Disclosed herein are methods of diagnosing Rheumatoid arthritis in a subject comprising determining whether the subject is immunologically reactive with *P. copri* or a portion thereof. In one aspect of the invention the immunological reactivity of the subject to one or more protein of *P. copri* or polypeptide fragments thereof such as protein Pc-p27 or polypeptide fragments thereof, as compared to an appropriate control, indicates the subject has rheumatoid arthritis. Examples of specific assays and kits for use with the methods are also disclosed.

14 Claims, 20 Drawing Sheets
Specification includes a Sequence Listing.

(56) References Cited

OTHER PUBLICATIONS

Bassani-Sternberg et al., "Soluble plasma HLA peptidome as a potential source for cancer biomarkers", Proc Natl Acad Sci USA 107(44) 18769-18776 (2010).
Behera et al., "Induction of host matrix metalloproteinases by Borrelia burgdorferi differs in human and murine lyme arthritis", Infect Immun 73(1) 126-134 (2005).
Berglin et al., "Radiological outcome in rheumatoid arthritis is predicted by presence of antibodies against cyclic citrullinated peptide before and at disease onset, and by IgA-RF at disease onset", Ann Rheum Dis 65(4) 453-458 (2006).
Burkhardt et al., "Humoral immune response to citrullinated collagen type II determinants in early rheumatoid arthritis", Eur J Immunol 35(5) 1643-1652 (2005).
Campbell, "Monoclonal Antibody Technology, Laboratory Techniques in Biochemistry and Molecular Biology", Elsevier Sci Pub 13 75-83 (1984).
Caron et al., "An open-source computational and data resource to analyze digital maps of immunopeptidomes", Elife 8; (2015).
Caron et al., "Analysis of Major Histocompatibility Complex (MHC) Immunopeptidomes Using Mass Spectrometry", Mol Cell Proeomics 14(12) 3105-3117 (2015).
Chen et al., "Modification of cysteine residues in vitro and in vivo affects the immunogenicity and antigenicity of major histocompatibility complex class I-restricted viral determinants", J Exp Med 189(11) 1757-1764 (1999).
Chicz et al., "Specificity and promiscuity among naturally processed peptides bound to HLA-DR alleles", J Exp Med 178(1) 27-47 (1993).
Cobbold et al., "MHC class I-associated phosphopeptides are the targets of memory-like immunity in leukemia", Sci Transl Med 5(203) 203ra125 (2013).
Collado et al., "Composition of the HLA-DR-associated human thymus peptidome", Eur J Immunol 43(9) 2273-2282 (2013).
Crowley et al., "A Highly Expressed Human Protein, Apolipoprotein B-100, Serves as an Autoantigen in a Subgroup of Patients With Lyme Disease", J Infect Dis 212(11) 1841-1850 (2015).
Crowley et al., "Matrix metalloproteinase-10 is a target of T and B cell responses that correlate with synovial pathology in patients with antibiotic-refractory Lyme arthritis", Journal of Autoimmunity 69; 24-37 (2016).
De Vries-Bouwstra et al., "Progression of joint damage in early rheumatoid arthritis: association with HLA-DRB1, rheumatoid factor, and anti-citrullinated protein antibodies in relation to different treatment strategies", Arthritis Rheum 58(5) 1293-1298 (2008).
Dengiel et al., "Unexpected abundance of HLA class II presented peptides in primary renal cell carcinomas", Clin Cancer Res 12(14 Pt 1) 4163-4170 (2006).
Drouin et al., "A novel human autoantigen, endothelial cell growth factor, is a target of T and B cell responses in patients with Lyme disease", Arthritis Rheum 65(1) 186-196 (2013).
Gordon et al., "Purification and characterization of endogenous peptides extracted from HLA-DR isolated from the spleen of a patient with rheumatoid arthritis", Eur J Immuno 25(5) 1473-1476 (1995).
Gregersen et al., "The shared epitope hypothesis. An approach to understanding the molecular genetics of susceptibility to rheumatoid arthritis", Arthritis Rheum 30(11) 1205-1213 (1987).
Guasp et al., "The Peptidome of Behçet's Disease-Associated HLA-B*51:01 Includes Two Subpeptidomes Differentially Shaped by Endoplasmic Reticulum Aminopeptidase 1", Arthritis Rheumatol 68(2) 505-515 (2016).
Haque et al., "Cysteinylation of MHC class II ligands: peptide endocytosis and reduction within APC influences T cell recognition", J Immunol 166(7) 4543-4551 (2001).
Hill et al., "Cutting edge: the conversion of arginine to citrulline allows for a high-affinity peptide interaction with the rheumatoid arthritis-associated HLA-DRB1*0401 MHC class II molecule", J Immunol 171(2) 538-541 (2003).
Holoshitz et al., "The rheumatoid arthritis HLA-DRB1 shared epitope", Curr Opin Rheumatol 22(3) 293-298 (2010).
Huizinga et al., "Refining the complex rheumatoid arthritis phenotype based on specificity of the HLA-DRB1 shared epitope for antibodies to citrullinated proteins", Arthritis Rheum 52(11) 3433-3438 (2005).
Hunt et al., "Characterization of peptides bound to the class I MHC molecule HLA-A2.1 by mass spectrometry", Science 255(5049) 1261-1263 (1992).
Katchar et al., "Natural killer cells and natural killer T cells in Lyme arthritis", Arthritis Res Ther 15(6) R183 (2013).
Kinloch et al., "Identification of citrullinated alpha-enolase as a candidate autoantigen in rheumatoid arthritis", Arthritis Res Ther 7(6) R1421-R1429 (2005).
Ladd et al., "Autoantibody signatures involving glycolysis and splicesome proteins precede a diagnosis of breast cancer among postmenopausal women." Cancer Research 73(5):1502-1513 (2013).
Li et al., "Structural basis for the presentation of tumor-associated MHC class II-restricted phosphopeptides to CD4+ T cells", J Mol Biol 399(4) 596-603 (2010).
Ling et al., "Citrullinated calreticulin potentiates rheumatoid arthritis shared epitope signaling", Arthritis Rheum 65(3) 618-626 (2013).
Lippolis et al., "Analysis of MHC class II antigen processing by quantitation of peptides that constitute nested sets", J Immunol 169(9) 5089-5097 (2002).
Londono et al., "Antibodies to endothelial cell growth factor and obliterative microvascular lesions in the synovium of patients with antibiotic-refractory lyme arthritis", Arthritis Rheumatol 66(8) 2124-2133 (2014).
Meadows et al., "The HLA-A*0201-restricted H-Y antigen contains a posttranslationally modified cysteine that significantly affects T cell recognition", Immunity 6(3) 273-281 (1997).
Moret et al., "Intra-articular CD1c-expressing myeloid dendritic cells from rheumatoid arthritis patients express a unique set of T cell-attracting chemokines and spontaneously induce Th1, Th17 and Th2 cell activity", Arthritis Res Ther 15(5) R155 (2013).
Oshitani et al., "Analysis of intestinal HLA-DR bound peptides and dysregulated immune responses to enteric flora in the pathogenesis of inflammatory bowel disease", Int J Mol Med 11(1) 99-104 (2003).
Pianta et al., "Annexin A2 is a target of autoimmune T and B cell responses associated with synovial fibroblast proliferation in patients with antibiotic-refractory Lyme arthritis", Clin Immunol 160(2) 336-341 (2015).
Pianta et al., "Identification of N-Acetylglucosamine-6-Sulfatase and Filamin a as Novel Targets of Autoimmune T and B Cell Responses in Rheumatoid Arthritis.", Annals of the Rheumatic Diseases 74:112 (2015). Abstract.
Pianta et al., "Identification of N-Acetylglucosamine-6-Sulfatase and Filamin a as Novel Targets of Autoimmune T and B Cell Responses in Rheumatoid Arthritis.", MGH Harvard Medical School; Boston U.S; Jun. 11, 2015, Poster No. 30.
Pianta et al., "(OP0116) Identification of N-Acetylglucosamine-6-Sulfatase and Filamin a as Novel Targets of Autoimmune T and B Cell Responses in Rheumatoid Arthritis." Annals of the Rheumatic Diseases 74(2):112.2 (2015).
Pierce et al., "Cutting edge: the HLA-A*0101-restricted HY minor histocompatibility antigen originates from DFFRY and contains a cysteinylated cysteine residue as identified by a novel mass spectrometric technique", J Immunol 163(12) 6360-6364 (1999).
Plenge, "Rheumatoid arthritis genetics: 2009 update", Curr Rhematol Rep 11(5) 351-356 (2009).
Pratesi et al., "HLA shared epitope and ACPA: just a marker or an active player?", Autoimmun Rev 12(12) 1182-1187 (2013).
Salle et al., "Anti-annexin II antibodies in systemic autoimmune diseases and antiphospholipid syndrome", J Clin Immunol 28(4) 291-297 (2008).
Seki et al., "Use of differential subtraction method to identify genes that characterize the phenotype of cultured rheumatoid arthritis synoviocytes", Arthritis Rheum 41(8) 1356-1364 (1998).
Seward et al., "Peptides presented by HLA-DR molecules in synovia of patients with rheumatoid arthritis or antibiotic-refractory Lyme arthritis", Mol Cell Proteomics 10(3) M110.002477 (2011).

(56) References Cited

OTHER PUBLICATIONS

Snir et al., "Multiple antibody reactivities to citrullinated antigens in sera from patients with rheumatoid arthritis: association with HLA-DRB1 alleles", Ann Rheum Dis 68(5) 736-743 (2009).

Spengler et al., "Release of Active Peptidyl Arginine Deiminases by Neutrophils Can Explain Production of Extracellular Citrullinated Autoantigens in Rheumatoid Arthritis Synovial Fluid", Arthritis Rheumatol 67(12) 3135-3145 (2015).

Steere et al., "Spirochetal antigens and lymphoid cell surface markers in Lyme synovitis. Comparison with rheumatoid synovium and tonsillar lymphoid tissue", Arthritis Rheum 31(4) 487-495 (1988).

Stefanova et al., "On the role of self-recognition in T cell responses to foreign antigen", Immunol Rev 191; 97-106 (2003).

Takemura et al., "Lymphoid neogenesis in rheumatoid synovitis", J Immunol 167(2) 1072-1080 (2001).

Takizawa et al., "Citrullinated fibrinogen detected as a soluble citrullinated autoantigen in rheumatoid arthritis synovial fluids", Ann Rheum Dis 65(8) 1013-1020 (2006).

Van Beers et al., "The rheumatoid arthritis synovial fluid citrullinome reveals novel citrullinated epitopes in apolipoprotein E, myeloid nuclear differentiation antigen, and β-actin", Arthritis Rheum 65(1) 69-80 (2013).

Vossenaar et al., "Rheumatoid arthritis specific anti-Sa antibodies target citrullinated vimentin", Arthritis Res Ther 6(2) R142-R150 (2004).

Wahlstrom et al., "Identification of HLA-DR-bound peptides presented by human bronchoalveolar lavage cells in sarcoidosis", J Clin Invest 117(11) 3576-3582 (2007).

Ytterberg et al., "Shared immunological targets in the lungs and joints of patients with rheumatoid arthritis: identification and validation", Ann Rheum Dis 74(9) 1772-1777 (2015).

Zhang et al., "DeMix workflow for efficient identification of cofragmented peptides in high resolution data-dependent tandem mass spectrometry", Mol Cell Protemoics 13(11) 3211-3223 (2014).

Moen et al., "Immunoglobulin G and A antibody responses to Bacteroides forsythus and Prevotella intermedia in sera and synovial fluids of arthritis patients", Clin Diagn Lab Immunol 10(6) 1043-1050 (2003).

Pianta et al., "Identification of a Broadly Immunogenic Prevotella Copri T Cell Patients with Theumatoid Arthritis", 2015 ACR/ARHP Annual Meeting (Abstract No. 1930) Sep. 2015.

Schellekens et al., "The diagnostic properties of rheumatoid arthritis antibodies recognizing a cyclic citrullinated peptide", Arthritis Rheum 43(1) 155-163 (2000).

Tan et al., "Specificity of T cells in synovial fluid: high frequencies of CD8(+) T cells that are specific for certain viral epitopes", Arthitis Res 2(2) 154-164 (2000).

Pianta et al. "Two rheumatoid arthritis-specific autoantigens correlate microbial immunity with autoimmune responses in joints." The Journal of Clinical Investigation, 127(8): 2946-2956 (2017).

Steere, A. C., Klitz, W., Drouin, E. E., Falk, B. A., Kwok, W. W., Nepom, G. T. and Baxter-Lowe, L. A. Antibiotic-refractory Lyme arthritis is associated with HLA-DR molecules that bind a Borrelia burgdorferi peptide J Exp Med 2006, 203, 961-971.

Van Steendam et al. "Quantification of IFNy- and IL 17-producting cells after stimulation with citrullinated proteins in healthy subjects and RA patients." Rheumatology Int. 33(10): 2661-2664 (2013).

\* cited by examiner

FIGs. 3A-3D
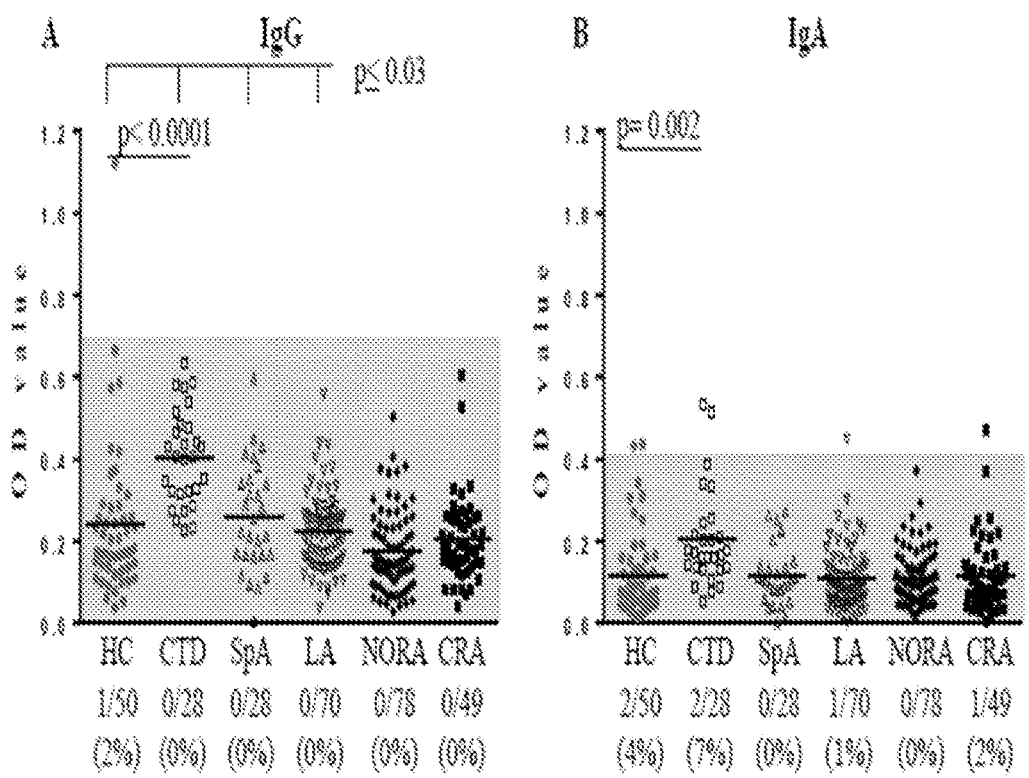
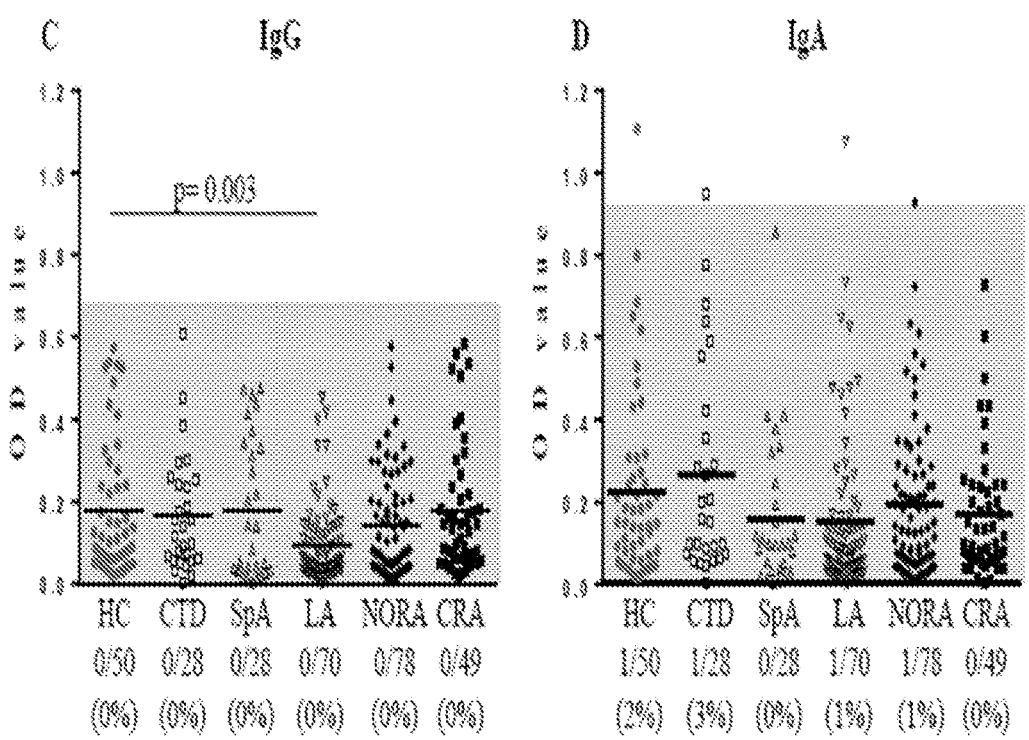

A

B

A  Correlation of GNS or FLNA autoantibodies with *P. copri* antibodies

B  Correlation of GNS or FLNA autoantibodies with *P. gingivalis* antibodies

SEQUENCE LISTING

```
<160> NUMBER OF SEQ ID NOS: 46

<210> SEQ ID NO 1
<211> LENGTH: 223
<212> TYPE: PRT
<213> ORGANISM: Prevotella copri

<400> SEQUENCE: 1

Met Lys Arg Ile Ile Leu Ile Leu Thr Val Leu Leu Ala Met Leu Gly
1               5                   10                  15

Gln Val Ala Tyr Ala Gln Lys Thr Cys Val Ile Ala Ser Ala Glu Asn
            20                  25                  30

His Val Pro Ile Arg Glu Ala Leu Ile His Thr Asn Asn Asn His Trp
        35                  40                  45

Ala Arg Thr Asp Tyr Arg Gly Tyr Trp Thr Met Arg Tyr Gln Phe Asp
    50                  55                  60

Ser Ala Thr Val Ser Lys Pro Gly Phe Met Lys Ala Thr Ile Arg Tyr
65                  70                  75                  80

Lys Glu Leu Pro Asp Thr Leu Phe Leu Leu Pro Asp Ala Lys Gln Leu
                85                  90                  95

Gly Glu Val Thr Val Trp Gly Lys Asn Gln Glu Gly Ile Lys Asn Met
            100                 105                 110

Glu Glu Asp Ile Gln Glu Lys Ile Asn Ser Leu Pro Thr Ser Ser Thr
        115                 120                 125

Gly Ile Gly Phe Asp Ala Phe Gly Trp Met Asp Lys Gln Gly Lys Arg
    130                 135                 140

Asp Lys Lys His Leu Gln Gln Ala Lys Lys Val Phe Glu Lys Met Glu
145                 150                 155                 160

His Lys Asp Pro Val Val Ala Ala Tyr Glu Lys Ala Thr Gly Lys Lys
                165                 170                 175

Tyr Glu Leu Thr Asn Pro Tyr Asp Val Ser Ala Phe Lys Lys Asp Pro
            180                 185                 190

Pro Ser Glu Met Ala Thr Glu Leu Lys Lys Ala Thr Ser Asp Ala Glu
        195                 200                 205

Ser Lys Ser Lys Lys Glu Asn Pro Glu Lys Tyr Ala Gln Glu
    210                 215                 220

<210> SEQ ID NO 2
<211> LENGTH: 19
<212> TYPE: PRT
<213> ORGANISM: Prevotella copri

<400> SEQUENCE: 2
```

Lys Arg Ile Ile Leu Ile Leu Thr Val Leu Leu Ala Met Leu Gly Gln
1               5                   10                  15

Val Ala Tyr

<210> SEQ ID NO 3
<211> LENGTH: 18
<212> TYPE: PRT
<213> ORGANISM: Prevotella copri

<400> SEQUENCE: 3

Asp Tyr Arg Gly Tyr Trp Thr Met Arg Tyr Gln Phe Asp Ser Ala Thr
1               5                   10                  15

Val Ser

<210> SEQ ID NO 4
<211> LENGTH: 13
<212> TYPE: PRT
<213> ORGANISM: Prevotella copri

<400> SEQUENCE: 4

Glu Lys Ile Asn Ser Leu Pro Thr Ser Ser Thr Gly Ile
1               5                   10

<210> SEQ ID NO 5
<211> LENGTH: 19
<212> TYPE: PRT
<213> ORGANISM: Prevotella copri
<220> FEATURE:
<221> NAME/KEY: MOD_RES
<222> LOCATION: (16)..(16)
<223> OTHER INFORMATION: Gln(deamidated)

<400> SEQUENCE: 5

Lys Arg Ile Ile Leu Ile Leu Thr Val Leu Leu Ala Met Leu Gly Gln
1               5                   10                  15

Val Ala Tyr

<210> SEQ ID NO 6
<211> LENGTH: 19
<212> TYPE: PRT
<213> ORGANISM: Prevotella copri

<400> SEQUENCE: 6

Lys Arg Ile Ile Leu Ile Leu Thr Val Leu Leu Ala Met Leu Gly Gln
1               5                   10                  15

Val Ala Tyr

<210> SEQ ID NO 7
<211> LENGTH: 18
<212> TYPE: PRT
<213> ORGANISM: Prevotella copri

<400> SEQUENCE: 7

Asp Tyr Arg Gly Tyr Trp Thr Met Arg Tyr Gln Phe Asp Ser Ala Thr
1               5                   10                  15

Val Ser

<210> SEQ ID NO 8
<211> LENGTH: 13
<212> TYPE: PRT
<213> ORGANISM: Prevotella copri

<400> SEQUENCE: 8

Glu Lys Ile Asn Ser Leu Pro Thr Ser Ser Thr Gly Ile
1               5                   10

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ccaagtagcg tgcaggatga                                               20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ttcaagcccg ggtaaggttc                                               20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cgcggtaata cggaaggtcc                                               20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gatacccgca ctttcgagct                                               20

<210> SEQ ID NO 13
<211> LENGTH: 13
<212> TYPE: PRT
<213> ORGANISM: Homo sapiens

<400> SEQUENCE: 13

Pro Asn Val Val Leu Leu Leu Thr Asp Asp Gln Asp Glu
1               5                   10

<210> SEQ ID NO 14
<211> LENGTH: 14
<212> TYPE: PRT
<213> ORGANISM: Homo sapiens

<400> SEQUENCE: 14

Phe Glu Pro Phe Phe Met Met Ile Ala Thr Pro Ala Pro His
1               5                   10

```
<210> SEQ ID NO 15
<211> LENGTH: 15
<212> TYPE: PRT
<213> ORGANISM: Homo sapiens

<400> SEQUENCE: 15

Thr Tyr Ala Cys Val Arg Thr Met Ser Ala Leu Trp Asn Leu Gln
1               5                   10                  15

<210> SEQ ID NO 16
<211> LENGTH: 15
<212> TYPE: PRT
<213> ORGANISM: Homo sapiens

<400> SEQUENCE: 16

Asn Tyr Arg Leu Met Met Leu Gln Ser Cys Ser Gly Pro Thr Cys
1               5                   10                  15

<210> SEQ ID NO 17
<211> LENGTH: 16
<212> TYPE: PRT
<213> ORGANISM: Homo sapiens

<400> SEQUENCE: 17

Asp Gly Leu Arg Leu Ile Ala Leu Leu Glu Val Leu Ser Gln Lys Lys
1               5                   10                  15

<210> SEQ ID NO 18
<211> LENGTH: 15
<212> TYPE: PRT
<213> ORGANISM: Homo sapiens

<400> SEQUENCE: 18

Ser Ile Lys Leu Val Ser Ile Asp Ser Lys Ala Ile Val Asp Gly
1               5                   10                  15

<210> SEQ ID NO 19
<211> LENGTH: 13
<212> TYPE: PRT
<213> ORGANISM: Homo sapiens

<400> SEQUENCE: 19

Val Glu Val Val Ile Gln Asp Pro Met Gly Gln Lys Gly
1               5                   10

<210> SEQ ID NO 20
<211> LENGTH: 15
<212> TYPE: PRT
<213> ORGANISM: Homo sapiens

<400> SEQUENCE: 20

Asn Pro Ala Glu Phe Val Val Asn Thr Ser Asn Ala Gly Ala Gly
1               5                   10                  15

<210> SEQ ID NO 21
<211> LENGTH: 14
<212> TYPE: PRT
<213> ORGANISM: Homo sapiens

<400> SEQUENCE: 21

Phe Glu Pro Phe Phe Met Met Ile Ala Thr Pro Ala Pro His
1               5                   10

<210> SEQ ID NO 22
```

```
<211> LENGTH: 14
<212> TYPE: PRT
<213> ORGANISM: Prevotella sp. DNF00663

<400> SEQUENCE: 22

Lys Lys Pro Phe Phe Met Met Val Ala Met Asn Pro Pro His
1               5                   10

<210> SEQ ID NO 23
<211> LENGTH: 14
<212> TYPE: PRT
<213> ORGANISM: Parabacteroides sp. HGS0025

<400> SEQUENCE: 23

Asp Val Pro Phe Phe Met Met Trp Thr Thr Pro Leu Pro His
1               5                   10

<210> SEQ ID NO 24
<211> LENGTH: 15
<212> TYPE: PRT
<213> ORGANISM: Homo sapiens

<400> SEQUENCE: 24

Asn Pro Ala Glu Phe Val Val Asn Thr Ser Asn Ala Gly Ala Gly
1               5                   10                  15

<210> SEQ ID NO 25
<211> LENGTH: 13
<212> TYPE: PRT
<213> ORGANISM: Prevotella sp. HUN102

<400> SEQUENCE: 25

Gln Gly Phe Val Val Lys Thr Ala Asn Ala Gly Ala Leu
1               5                   10

<210> SEQ ID NO 26
<211> LENGTH: 13
<212> TYPE: PRT
<213> ORGANISM: Butyricimonas sp. Marseille-P2440

<400> SEQUENCE: 26

Ala Asn Phe Met Ile Asn Val Ser Asn Ala Gly Ala Leu
1               5                   10

<210> SEQ ID NO 27
<211> LENGTH: 50
<212> TYPE: DNA
<213> ORGANISM: Prevotella copri

<400> SEQUENCE: 27
gaaatgtaga cgctcaacgt ctgcactgca gcgcgaactg gtttccttga          50

<210> SEQ ID NO 28
<211> LENGTH: 50
<212> TYPE: DNA
<213> ORGANISM: Prevotella copri

<400> SEQUENCE: 28
gaaaaatacc ggctcaaccg gtatcctgca gcgcgaactg cctggcttga          50

<210> SEQ ID NO 29
<211> LENGTH: 50
<212> TYPE: DNA
<213> ORGANISM: Prevotella copri
<220> FEATURE:
```

<221> NAME/KEY: modified_base
<222> LOCATION: (9)..(10)
<223> OTHER INFORMATION: a, c, t, g, unknown or other

<400> SEQUENCE: 29
gaaatgtann cgctcaacgt ctgcactgca gcgcgaactg gtttccttga                50

<210> SEQ ID NO 30
<211> LENGTH: 50
<212> TYPE: DNA
<213> ORGANISM: Prevotella copri

<400> SEQUENCE: 30 gaaaaccgt cgctcaacga cggccgtgca gcgcgaactg gacgccttga                 50

<210> SEQ ID NO 31
<211> LENGTH: 50
<212> TYPE: DNA
<213> ORGANISM: Prevotella copri
<220> FEATURE:
<221> NAME/KEY: modified_base
<222> LOCATION: (5)..(6)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other
<220> FEATURE:
<221> NAME/KEY: modified_base
<222> LOCATION: (25)..(25)
<223> OTHER INFORMATION: a, c, t, g, unknown or other
<220> FEATURE:
<221> NAME/KEY: modified_base
<222> LOCATION: (44)..(44)
<223> OTHER INFORMATION: a, c, t, g, unknown or other

<400> SEQUENCE: 31
gaaanntagn cgctcaacgt ctgcnctgca gcgcgaactg gttnccttga                50

<210> SEQ ID NO 32
<211> LENGTH: 50
<212> TYPE: DNA
<213> ORGANISM: Prevotella copri

<400> SEQUENCE: 32
gtacgcacaa agtgggcgga attcgtggtg tagcggtgaa atgcttagat                50

<210> SEQ ID NO 33
<211> LENGTH: 50
<212> TYPE: DNA
<213> ORGANISM: Prevotella copri

<400> SEQUENCE: 33
gtgtgcgcaa cgttggcgga attcgtcgtg tagcggtgaa atgcttagat                50

<210> SEQ ID NO 34
<211> LENGTH: 50
<212> TYPE: DNA
<213> ORGANISM: Prevotella copri

<400> SEQUENCE: 34
gtacgcacaa agtgggcgga attcgtggtg tagcggtgaa atgcttagat                50

<210> SEQ ID NO 35
<211> LENGTH: 50
<212> TYPE: DNA
<213> ORGANISM: Prevotella copri

```
<400> SEQUENCE: 35
gtgcgctgaa agtgggcgga atttgtggtg tagcggtgaa atgcttagat         50

<210> SEQ ID NO 36
<211> LENGTH: 50
<212> TYPE: DNA
<213> ORGANISM: Prevotella copri
<220> FEATURE:
<221> NAME/KEY: modified_base
<222> LOCATION: (3)..(3)
<223> OTHER INFORMATION: a, c, t, g, unknown or other

<400> SEQUENCE: 36
gtncgcacaa agtgggcgga attcgtggtg tagcggtgaa atgcttagat         50

<210> SEQ ID NO 37
<211> LENGTH: 14
<212> TYPE: PRT
<213> ORGANISM: Homo sapiens

<400> SEQUENCE: 37

Phe Glu Pro Phe Phe Met Met Ile Ala Thr Pro Ala Pro His
1               5                   10

<210> SEQ ID NO 38
<211> LENGTH: 12
<212> TYPE: PRT
<213> ORGANISM: Prevotella sp.

<400> SEQUENCE: 38

Pro Phe Phe Met Met Val Ala Met Asn Pro Pro His
1               5                   10

<210> SEQ ID NO 39
<211> LENGTH: 12
<212> TYPE: PRT
<213> ORGANISM: Parabacteroides sp.

<400> SEQUENCE: 39

Pro Phe Phe Met Met Trp Thr Thr Pro Leu Pro His
1               5                   10

<210> SEQ ID NO 40
<211> LENGTH: 15
<212> TYPE: PRT
<213> ORGANISM: Homo sapiens

<400> SEQUENCE: 40

Asn Pro Ala Glu Phe Val Val Asn Thr Ser Asn Ala Gly Ala Gly
1               5                   10                  15

<210> SEQ ID NO 41
<211> LENGTH: 10
<212> TYPE: PRT
<213> ORGANISM: Prevotella sp.

<400> SEQUENCE: 41

Phe Val Val Lys Thr Ala Asn Ala Gly Ala
1               5                   10

<210> SEQ ID NO 42
<211> LENGTH: 10
<212> TYPE: PRT
<213> ORGANISM: Butyricimonas sp.
```

```
<400> SEQUENCE: 42

Phe Met Ile Asn Val Ser Asn Ala Gly Ala
1               5                   10

<210> SEQ ID NO 43
<211> LENGTH: 14
<212> TYPE: PRT
<213> ORGANISM: Homo sapiens

<400> SEQUENCE: 43

Phe Glu Pro Phe Phe Met Met Ile Ala Thr Pro Ala Pro His
1               5                   10

<210> SEQ ID NO 44
<211> LENGTH: 14
<212> TYPE: PRT
<213> ORGANISM: Homo sapiens

<400> SEQUENCE: 44

Phe Glu Pro Phe Phe Met Met Ile Ala Thr Pro Ala Pro His
1               5                   10

<210> SEQ ID NO 45
<211> LENGTH: 15
<212> TYPE: PRT
<213> ORGANISM: Homo sapiens

<400> SEQUENCE: 45

Asn Pro Ala Glu Phe Val Val Asn Thr Ser Asn Ala Gly Ala Gly
1               5                   10                  15

<210> SEQ ID NO 46
<211> LENGTH: 15
<212> TYPE: PRT
<213> ORGANISM: Homo sapiens

<400> SEQUENCE: 46

Asn Pro Ala Glu Phe Val Val Asn Thr Ser Asn Ala Gly Ala Gly
1               5                   10                  15
```

IDENTIFICATION OF A T CELL EPITOPE OF *PREVOTELLA COPRI* THAT INDUCES T CELL RESPONSES IN PATIENTS WITH RHEUMATOID ARTHRITIS

RELATED APPLICATIONS

This application is a 35 U.S.C. § 371 National Entry Application of International Application No. PCT/US2017/036198 filed Jun. 6, 2017, which designates the U.S. and claims the benefit under 35 U.S.C. § 119(e) of U.S. Provisional Application No. 62/346,666, filed Jun. 7, 2016, the contents of each of which are incorporated herein by reference in their entirety.

GOVERNMENTAL SUPPORT

This invention was made with government support under Grant Nos. P41 GM104603, S10 RR020946 and S10 OD010724 awarded by the National Institutes of Health (NIH). The government has certain rights in the invention.

SEQUENCE LISTING

The instant application contains a Sequence Listing which has been submitted electronically in ASCII format and is hereby incorporated by reference in its entirety. Said ASCII copy, created on Jun. 27, 2017, is named 030258-087241-PCT_SL.txt and is 11,219 bytes in size.

TECHNICAL FIELD

The present invention relates to the field of diagnostics using humoral and cellular autoimmune responses to gut microbe *Prevotella copri* (*P. copri*). In particular it relates to use of *P. copri* proteins in diagnosis and treatment of Rheumatoid arthritis.

BACKGROUND

Rheumatoid arthritis (RA), the prototypic autoimmune joint disease, results from a complex interplay between genetic and environmental factors (Firestein, 2003; McInnes and Schett, 2011). Great progress has been made in the identification of genetic factors and inflammatory pathways that influence the disease (McInnes and Schett, 2011; Plenge, 2009), but environmental factors are only now being determined (Catrina et al., 2014). A key hypothesis is that specific organisms in the mouth or gut microbiota, the composition of which is strongly influenced by environmental cues, may shape mucosal and systemic immune responses that affect joints in RA patients (Catrina et al., 2014; Han and Wang, 2013; Longman and Littman, 2015; Scher and Abramson, 2011).

In seminal studies, Littman and colleagues explored the role of the gut microbiota in shaping immune responses in animal models. In mice, segmented filamentous bacteria (SFB) penetrate the mucus layer of the gut and bind epithelial cells where they stimulate Th17-cell responses (Hooper et al., 2012; Ivanov et al., 2009; Ivanov and Honda, 2012). These studies highlight the potential benefits and disadvantageous aspects of Th17 responses. These cells promote barrier protection at the mucosal surface, but they can also contribute to systemic inflammation and autoimmunity.

Although humans do not have SFB, other bacteria may serve a similar function in human autoimmune disease. Using high-through-put sequencing, Scher et al. showed that *Prevotella copri* in the gut microbiota was over-expanded in stool samples from patients with new-onset RA (NORA) compared with patients with chronic RA (CRA), psoriatic arthritis, or healthy people (Scher et al., 2013). In NORA patients, *Prevotella* abundance in the gut was at the expense of *Bacteroides fragilis*, an organism that is important for Treg function (Atarashi et al., 2011; Round et al., 2011). In addition, according to the NCBI database, *P. copri* has a gene sequence that would code for a peptidylarginine deiminase-related protein (WP_006847349), which could potentially contribute to citrullination of proteins and production of anti-citrullinated protein antibodies (ACPA), a specific autoantibody response in RA (Nishimura et al., 2007; Schellekens et al., 1998; Suzuki et al., 2003).

A recent metagenome-wide analysis of fecal, dental, and salivary samples in RA patients showed similar dysbiosis not only in the gut, but also in the mouth and salivary glands (Zhang et al., 2015). In this study, a trend toward increased abundance of *P. copri* in stool samples was also seen during the first year of disease. Therefore, two studies have now shown that the gut microbiome in RA patients is distinct from that of healthy individuals. However, it is unclear whether over-expansion of *P. copri* in stool is simply the result of gut dysbiosis or whether the organism has the potential to regulate immune cell functions at both mucosal and systemic sites, thereby contributing to RA disease pathogenesis.

SUMMARY

Aspects of the invention relate to a method for determining whether a biological sample comprising antibodies and/or immunological cells obtained from a subject is immunologically reactive with *P. copri* Pc-p27 protein or antigen thereof, comprising performing an assay for identifying the presence of antibodies that specifically bind *P. copri* Pc-p27 protein or antigen thereof or performing an assay for identifying T cells specifically reactive to *P. copri* Pc-p27 protein or antigen thereof, and determining the sample is reactive with the *P. copri* Pc-p27 protein or antigen thereof if the assay produces positive results compared to an appropriate control.

In some embodiments, the assay that identifies the presence of the antibodies comprises contacting the sample with *P. copri* Pc-p27 protein or antigen thereof, under conditions that allow an immunocomplex of the antibody and the *P. copri* Pc-p27 protein or antigen thereof to form, and detecting the presence or absence of the immunocomplex, wherein the presence of the immunocomplex indicates the biological sample is immunoreactive with the *P. copri* Pc-p27 protein or antigen thereof and wherein the absence of the immunocomplex indicates the biological sample is not immunoreactive with the *P. copri* Pc-p27 protein or antigen thereof.

In some embodiments the antibodies are IgG or IgA. In some embodiments the assay is an ELISA, agglutination test, direct immunofluorescence assay, indirect immunofluorescence assay, or an immunoblot assay.

In some embodiments, the assay for identifying T cells specifically reactive to *P. copri* Pc-p27 protein or antigen thereof comprises: (a) stimulating peripheral blood mononuclear cells (PBMC) of the subject or the synovial fluid mononuclear cells (SFMC) of the subject in vitro with *P. copri* Pc-p27 protein or antigen thereof; (b) measuring T cell proliferation in vitro or secretion of IFN-γ into cell culture supernatants; and (c) identifying the subject as having T cells specifically reactive to *P. copri* Pc-p27 protein or antigen thereof, when T cell proliferation or secretion of IFN-γ measured is substantially increased over that of an appropriate control.

In some embodiments of the foregoing aspects the assay for identifying T cells specifically reactive to *P. copri* Pc-p27 protein or antigen thereof, is a T cell proliferation assay. In some embodiments the assay is a ³H-thymdine incorporation assay, CFSE dilution, or an ELISPOT.

In some embodiments of the foregoing aspects the assay for identifying T cells specifically reactive to *P. copri* Pc-p27 protein or antigen thereof, is a T cell reactivity assay.

In some embodiments of the foregoing aspects, the biological sample is obtained from peripheral blood, synovial fluid, synovial tissue, peripheral blood mononuclear cells (PBMC), or synovial fluid mononuclear cells (SFMC).

Another aspect of the invention relates to diagnosing Rheumatoid arthritis in a subject comprising determining whether the subject is immunologically reactive with *P. copri* or a portion thereof, wherein immunological reactivity of the subject to *P. copri* or a portion thereof as compared to an appropriate control, indicates the subject has Rheumatoid arthritis.

In some embodiments, the determining is by evaluating a biological sample obtained from the subject for immunological reactivity with the *P. copri* or a portion thereof. In some embodiments, determining immunological reactivity is by detecting a T cell response to *P. copri* or a portion thereof in the subject by processing a biological sample obtained from the subject.

In some embodiments of the foregoing aspects, detecting a T cell response is by detecting the presence of T cells reactive to *P. copri* or a portion thereof. In some embodiments, the T cell response is a Th17 response.

In some embodiments, the detecting the presence of T cells comprises: (a) stimulating peripheral blood mononuclear cells (PBMC) of the subject or the synovial fluid mononuclear cells (SFMC) of the subject in vitro with *P. copri* or a portion thereof, and (b) measuring T cell proliferation in vitro or secretion of IFN-γ into cell culture supernatants; (c) identifying the subject as having T cells reactive to *P. copri* or a portion thereof when T cell proliferation or secretion of IFN-γ is measured as significantly increased over that of an appropriate control.

In some embodiments of the foregoing aspects, determining immunological reactivity comprises determining if the subject has a B-cell response to *P. copri* or a portion thereof resulting in the production of antibodies that specifically recognize the *P. copri* or a portion thereof, by contacting the sample with the *P. copri* or a portion thereof, under conditions that allow an immunocomplex of the antibody and the *P. copri* or a portion thereof to form, and detecting the presence or absence of an immunocomplex, wherein the presence of an immunocomplex indicates the subject presents a B-cell response to the *P. copri* or a portion thereof and wherein the absence of an immunocomplex indicates the subject fails to present a B-cell response to the *P. copri* or a portion thereof.

In some embodiments, the assay is an enzyme-linked immunosorbent assay (ELISA), agglutination test, direct immunofluorescence assay, indirect immunofluorescence assay, or an immunoblot assay.

In some embodiments the biological sample is obtained from peripheral blood, synovial fluid, synovial tissue, peripheral blood mononuclear cells (PBMC), or synovial fluid mononuclear cells (SFMC).

In some embodiments, the portion of *P. copri* is a protein or polypeptide fragment(s) of *P. copri*. In some embodiments the protein is Pc-p27 whole protein or polypeptide fragment(s) thereof. In some embodiments, the Pc-p27 polypeptide fragment is predicted to be presented by HLA-DR molecules associated with chronic inflammatory arthritis.

In some embodiments of the foregoing aspects, the polypeptide fragment is selected from the group consisting of KRIILILTVLLAMLGQVAY (SEQ ID NO: 2), or antigenic portion thereof; DYRGYWTMRYQFDSATVS (SEQ ID NO: 3) or antigenic portion thereof; EKINSLPTSSTGI (SEQ ID NO: 4) or antigenic portion thereof; and combinations thereof.

In some embodiments, the subject exhibits symptoms of arthritis or other autoimmune related disease manifestation. In some embodiments, the subject is suspected of having Rheumatoid arthritis. In some embodiments, the subject is suspected of having or suffers from new onset rheumatoid arthritis or chronic rheumatoid arthritis. In some embodiments, the subject has been further tested for one or more of rheumatoid factor (RF), anti-citrullinated protein antibodies (ACPA), *Prevotella* DNA in their synovial fluid, and one or more HLA-DR alleles. In some embodiments, the subject is further tested for *P. copri* in a biological sample of the subject.

In some embodiments, the biological sample is synovial fluid or serum, and the subject is tested for the presence of *P. copri* 16S rDNA.

In some embodiments, the subject tests positive for one or more of (RF), (ACPA), *Prevotella* DNA in their synovial fluid, and one or more HLA-DR alleles. In some embodiments, the subject tests negative for one or more of (RF), (ACPA), *Prevotella* DNA in their synovial fluid, and one or more HLA-DR alleles. In some embodiments, the HLA-DR allele is HLA-DRB1*0101 and/or HLA-DRB1*0401.

In some embodiments, the methods of the foregoing aspects further comprises the step of treating the subject who comprises the antibodies and/or immune cells for rheumatoid arthritis. In some embodiments, the treating is by administration of a therapeutically effective amount of one or more of a nonsteroidal anti-inflammatory drug (NSAIDs), a steroid, a disease modifying anti-rheumatic drug (DMARD), an antibiotic, and a biologic, to the subject.

Another aspect of the invention relates to a kit comprising, one or more of *P. copri* or a portion thereof, and reagents for conducting an assay for detecting the presence of an antibody in a sample that binds to the one or more of *P. copri* or a portion thereof.

In some embodiments, the kit further comprises reagents for conducting an assay for detecting the presence of one or more cytokines or chemokines. In some embodiments, the cytokines or chemokines comprise one or more of IL-23, IL-22, IL-17E, IL-17F IFN-γ, TNF, IFN-α, MIP-1α, MMP-1β, IL-17F, IL-1β, CXCL9, CXCL10, IL-12.

In some embodiments, the assay is an enzyme-linked immunosorbent assay (ELISA). In some embodiments, the assay is a western blot. In some embodiments, the kit further comprises *E. coli* and/or *B. fragilis* whole cells or potential antigens derived from them.

In some embodiments of the present invention, the kit or method of the foregoing aspects are used in identifying a patient with Rheumatoid arthritis. In some embodiments, the Rheumatoid arthritis is new onset rheumatoid arthritis or chronic rheumatoid arthritis.

Definitions

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

As used herein, the terms "diagnose" or "diagnosis" or "diagnosing" refers to determining the nature or the identity of a condition or disease or disorder, detecting and/or classifying the disease and/or disorder in a subject. A diagnosis may be accompanied by a determination as to the severity of the disease. The term also encompasses assessing or evaluating the disease status (progression, regression, stabilization, response to treatment, etc.) in a patient known to have the disease). Diagnosis as it relates to the present invention, relates to the diagnosis of chronic inflammatory arthritis e.g., Rheumatoid arthritis. The diagnosis can be differential diagnosis. As used herein, "differential diagnosis" refers to determination of which two or more diseases with similar symptoms (e.g., RA, osteoarthritis, systemic lupus erythematosus, Lyme arthritis, reactive arthritis, psoriatic arthritis, ankylosing spondylitis) is the one from which a patient is suffering from based on an analysis of clinical data such as for example results obtained from methods described herein.

As used herein, the term "biological sample" refers to a sample obtained for evaluation in vitro. The biological sample can be any sample that is expected to contain antibodies and/or immune cells. The sample can be taken from a part of the body that is specifically affected by the disorder, such as taken specifically from a site of inflammation or pathology in the subject (e.g., synnovial fluid, synovial tissue, synovial fluid mononuclear cells (SFMC), spinal fluid, etc.) or can be a more systemic sample (e.g., peripheral blood, peripheral blood mononuclear cells (PBMC), whole blood or whole blood pre-treated with an anticoagulent such as heparin, ethylenediamine tetraacetic acid, plasma or serum). Sample can be pretreated prior to use, such as preparing plasma from blood, diluting viscous liquids, or the like; methods of treatment can also involve separation, filtration, distillation, concentration, inactivation of interfering components, and the addition of reagents.

As used herein, "immunologically reactive" or "immunoreactive" is defined as the capability of the molecule (e.g., *P. copri* whole cell, whole protein thereof or polypeptide fragments thereof, protein Pc-p27 or one or more polypeptide fragment thereof) of the present invention to induce a specific immune response (e.g., T cell reactivity, B cell response) in appropriate subjects or cells and to bind with specific antibodies. The immunological reactivity can be assayed in a biological sample comprising immunological cells and/or antibodies obtained from a subject by methods described herein.

As used herein "autoantigen/self-antigen" is any substance normally found within a subject which, in an abnormal situation, is no longer recognized as part of the subject itself by the lymphocytes or antibodies of that subject, and is therefore attacked by the immune system as though it were a foreign substance. An autoantigen can be a naturally occurring molecule such as a protein normally produced and used by the subject itself, eliciting an immune response possibly leading to an autoimmune disease (e.g. RA) in the subject.

The term "antibody," as used herein, refers to an immunoglobulin molecule which is able to "specifically recognize" and/or "specifically bind" to a specific epitope on an antigen. Antibodies can be intact immunoglobulins derived from natural sources or from recombinant sources and can be immunoreactive portions of intact immunoglobulins. Antibodies are typically immunoglobulin molecules. As it relates to the present invention, the antibody can be IgG or IgA antibody.

As used herein, "autoantibody" means an antibody produced by the immune system of a subject that is directed to, and specifically binds to an "autoantigen/self-antigen" or an "antigenic epitope" thereof.

As used herein, the term "epitope" refers to that portion of any molecule capable of being recognized by, and bound by, a T cell or an antibody (the corresponding antibody binding region may be referred to as a paratope), and/or eliciting an immune response. In general, B cell epitopes consist of chemically active surface groupings of molecules, e.g., amino acids, and have specific three-dimensional structural characteristics as well as specific charge characteristics. T cell epitopes are linear groups of amino acids that are presented to the immune system by HLA-DR or DQ molecules on host antigen presenting cells. As used herein, "immunogenic epitope", as determined by any method known in the art, is defined as a portion of a polypeptide that causes an immune response in a subject. As used herein, "antigenic epitope", as determined by any methods well known in the art, in that a given antibody or T cell receptor specifically recognizes and specifically binds to a given antigen. It can be, and is defined as a portion of a protein (e.g. Pc-p27). As used herein, "antigenic portion" refers to the portion of Pc-p27 that includes the antigenic epitopes.

"Specifically bind" and/or "specifically recognize" as used herein, refers to the higher affinity of a binding molecule for a target molecule compared to the binding molecule's affinity for non-target molecules. A binding molecule that specifically binds a target molecule does not substantially recognize or bind non-target molecules. e.g., an antibody "specifically binds" and/or "specifically recognize" another molecule, meaning that this interaction is dependent on the presence of the binding specificity of the molecule structure, e.g., an antigenic epitope. For example, an antibody that specifically binds to the antigenic epitope of protein molecules such as Pc-p27 and/or polypeptide fragments thereof, instead of indiscriminately binding to cause non-specific binding and/or background binding. As used herein, "non-specific binding" and "background binding" refers to the interaction that does not depend on the presence of specific structure (e.g., a specific antigenic epitopes).

As used herein, an "immunoassay" refers to any binding assay that uses an antibody capable of binding specifically to a target molecule to detect and quantify the target molecule.

As used herein, an "appropriate control" refers to one or more biological samples obtained from a subject not afflicted with a disease or disorder that features abnormal level of the molecule and measurement of the molecule therein. An example of an appropriate control can be biological sample from a subject not afflicted from RA. As it relates to the present invention, an appropriate negative control sample would not be positive for T cell reactivity to and/or show presence of antibodies to *P. copri* or a portion thereof, protein Pc-p27 or one or more polypeptide fragments thereof when tested using the methods described herein.

The terms "disease", "disorder", or "condition" are used interchangeably herein, refer to any alternation in state of the body or of some of the organs, interrupting or disturbing the performance of the functions and/or causing symptoms such as discomfort, dysfunction, distress, or even death to the person afflicted or those in contact with a person. A disease or disorder can also be related to a distemper, ailing, ailment, malady, disorder, sickness, illness, complaint, or affectation.

As used herein, the terms "treat," "treatment," "treating," or "amelioration" refer to therapeutic treatments, wherein the object is to reverse, alleviate, ameliorate, inhibit, slow down or stop the progression or severity of Rheumatoid arthritis, (e.g. new onset rheumatoid arthritis or chronic rheumatoid arthritis), an associated condition and/or a symptom thereof. The term "treating" includes reducing or alleviating at least one adverse effect or symptom of RA. Treatment is generally "effective" if one or more symptoms or clinical markers (e.g. antibodies to one or more of Pc-p27 or cyclic citrullinated peptide (anti-CCP) and/or rheumatoid factors) are reduced. Alternatively, or in addition, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Accordingly in case of chronic inflammatory arthritis such as RA, "effective treatment" can for example reduce inflammation, swelling and joint pain, bone deformity and/or result in reduction in T or B cell reactivity to *P. copri*, Pc-p27 and/or polypeptides thereof and/or reduction in antibodies to *P. copri*, Pc-p27 and/or polypeptides thereof compared to that observed pre-treatment, as determined by methods described herein. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality. For example, treatment is considered effective if the condition is stabilized. The term "treatment" of a disease also includes providing relief from the symptoms or side-effects of the disease (including palliative treatment).

As used herein, a "subject", "patient", "individual" and like terms are used interchangeably and refers to a vertebrate, preferably a mammal, more preferably a primate, still more preferably a human. Mammals include, without limitation, humans, primates, rodents, wild or domesticated animals, including feral animals, farm animals, sport animals, and pets. Primates include, for example, chimpanzees, cynomologous monkeys, spider monkeys, and macaques, e.g., Rhesus. Rodents include, for example, mice, rats, woodchucks, ferrets, rabbits and hamsters. Domestic and game animals include, for example, cows, horses, pigs, deer, bison, buffalo, feline species, e.g., domestic cat, and canine species, e.g., dog, fox, wolf, avian species, e.g., chicken, emu, ostrich, and fish, e.g., trout, catfish and salmon. The terms, "individual," "patient" and "subject" are used interchangeably herein. In one embodiment the subject is male. In another embodiment, the subject is female.

Preferably, the subject is a mammal. The mammal can be a human, non-human primate, mouse, rat, dog, cat, horse, or cow, but is not limited to these examples. Mammals other than humans can be advantageously used as subjects that represent animal models of conditions or disorders associated with RA. Such models are known in the art and are described in (Asquith et al., 2009). In addition, the compositions and methods described herein can be used to diagnose domesticated animals and/or pets.

A subject can be one who has been previously diagnosed with or identified as suffering from or under medical supervision for a chronic inflammatory and/or autoimmune disease (e.g., RA). A subject can be one who is diagnosed and currently being treated for, or seeking treatment, monitoring, adjustment or modification of an existing therapeutic treatment, or is at a risk of developing RA, e.g., due to family history, carrying alleles or genotype associated with RA (e.g. HLA-DRB1*0101 and DRB1*0401, HLA-DRB1*0405 and DRB1*0408). The subject can exhibit one or more symptoms of autoimmune disease (e.g., RA) (e.g. swollen joints, joint pains). The subject may have tested positive with other assays for RA associated factor. Such factors include rheumatoid factor, anti-citrullinated protein antibodies (ACPA), one or more of HLA-DR alleles associated with RA, or other autoantigens. The subject may lack one or more symptoms of autoimmune disease. The subject may be identified as testing negative for other RA associated factors (rheumatoid factor, anti-citrullinated protein antibodies (ACPA), one or more of HLA-DR alleles, and other autoantigens).

As used herein, the terms "protein", "peptide" and "polypeptide" are used interchangeably to designate a series of amino acid residues connected to each other by bonds between the alpha-amino and carboxy groups of adjacent residues. The terms "protein", "peptide" and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein", "peptide" and "polypeptide" are used interchangeably herein when referring to a gene product and fragments thereof.

The term "statistically significant" or "significantly" refers to statistical significance and generally means a difference of two standard deviations (2SD) or more.

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Immunology by Werner Luttmann, published by Elsevier, 2006. Definitions of common terms in molecular biology can also be found in Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (3 ed.), Cold Spring Harbor Laboratory Press, Cold Spring Harbor, N.Y., USA (2001); Davis et al., Basic Methods in Molecular Biology, Elsevier Science Publishing, Inc., New York, USA (1995); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Although methods and materials similar or equivalent to those described herein can be used in the practice or testing of this disclosure, suitable methods and materials are described below. The abbreviation, "e.g.," is derived from the Latin exempli gratia, and is used herein to indicate a non-limiting example. Thus, the abbreviation "e.g.," is synonymous with the term "for example."

As used in this specification and appended claims, the singular forms "a," "an", and "the" include plural references unless the context clearly dictates otherwise. Thus for example, reference to "the method" included one or more methods, and/or steps of the type described herein and/or which will become apparent to those persons skilled in the art upon reading this disclosure and so forth.

In this application and the claims, the use of the singular includes the plural unless specifically stated otherwise. In addition, use of "or" means "and/or" unless stated otherwise. Moreover, the use of the term "including", as well as other forms, such as "includes" and "included", is not limiting. Also, terms such as "element" or "component" encompass both elements and components comprising one unit and elements and components that comprise more than one unit unless specifically stated otherwise.

BRIEF DESCRIPTION OF THE DRAWINGS

(FIG. 1A) Tandem mass spectra of the precursor ions [M+3H]$^{3+}$ at m/z 710.4430 from RA1 PBMC. Collision-induced dissociation was used to fragment the precursor ions on the LTQ-Orbitrap XL mass spectrometer, and the LTQ XL linear ion trap was used as the detector for the fragment ions. The resulted fragment ions were submitted to *P. copri* protein database using three search engines, Mascot, OMSSA, and X!Tandem. Consensus peptide identification was achieved as KRIILILTVLLAMLGQ(deamidated)VAY (SEQ ID NO: 5) by OMSSA and X!Tandem. The insert panel shows the IFN-γ ELISpot assay using matching patient's PBMC stimulated with the peptide (1, 2 and 4 µM). Reactivity of >3 times background (no antigen) was considered positive. (FIG. 1B) IFN-γ ELISpot assay using PBMC from patients with rheumatoid arthritis (RA), Lyme arthritis (LA), and healthy controls (HC) incubated with the HLA-DR-presented peptide identified from the PBMC of patient RA1 (Peptide1, 1 µM). (FIG. 1C) IFN-γ secretion of PBMC from patients and control subjects incubated with 2 predicted promiscuous HLA-DR binding peptides from Pc-p27 (1 µM each). A positive response was defined as >3 SD above the mean value of the HC (area above the shaded region). The value for patient RA1 is indicated with a star. Horizontal lines represent the mean values of each group. (FIG. 1D) IFN-γ secretion of PBMC from patients and controls stimulated with peptide 1 with and without citrullination. (FIG. 1E) Comparison of T cell reactivity between peptide 1 with or without citrullination in RA patients. SFU=spot forming units.

FIGS. 3A-3D show IgG and IgA responses to *B. fragilis* and *E. coli* in RA patients and controls. Serum samples from the same 303 individuals, shown in FIG. 2, were tested for antibody responses to other commensal bacteria. ELISA of serum IgG (FIG. 3A) and IgA (FIG. 3B) against 1% formalin-inactivated *B. fragilis*; ELISA of serum IgG (FIG. 3C) and IgA (FIG. 3D) against 1% formalin-inactivated *E. coli*. For all analyses, positivity was defined as >3 SD above the mean value of healthy controls (area above the shaded region). Symbols represent values in individual patients and horizontal lines show mean values. Only significant P values are shown. HC, healthy control; CTD, connective tissue diseases; SpA, spondyloarthropathies; LA, Lyme arthritis; NORA, new onset rheumatoid arthritis; CRA, chronic rheumatoid arthritis.

(FIG. 7A) Nested PCR of *P. copri* 16S rDNA amplicons (254 bp) analyzed on 1.5% agarose gels stained with ethidium bromide. Results from serum and SF samples from the 3 positive patients are shown. Patient RA1 had 4 paired serum and SF samples; patient RA2 had 1 serum and 2 SF samples, and patient RA5 had 1 serum and 1 SF samples. In patients RA2 and RA5, enough material was available for testing in duplicate. M, 100 bp DNA ladder; +, positive control (*P. copri* DSM 18205); H, water control. (FIG. 7B) Sequence alignment of the 16S gene amplicons obtained from patient RA1, RA2 and RA5 using CLC Genomic Workbench software. The sequence of *P. copri* (DSM 18205) 16S gene is shown as the reference and the conservation of all sequence positions is shown below the alignment.

FIG. 10 shows T cell reactivity against GNS and FLNA peptides in rheumatoid arthritis patients and comparison groups. In initial experiments, (FIG. 10A) PBMC from patients with rheumatoid arthritis (RA), Lyme arthritis (LA), or healthy controls (HC) subjects were stimulated with a pool of 4 peptides, including the single GNS HLA-DR presented peptide isolated from the synovial tissue of patient RA1 and 3 predicted promiscuous HLA-DR binding peptides from GNS (1 µM each).

FIG. 11 shows IgG and IgA responses to GNS and FLNA in RA patients and comparison groups. Serum samples from 259 individuals with RA, other forms of chronic inflammatory arthritis or healthy controls were tested for autoantibodies by ELISA.

FIG. 13 shows autoantibody responses to citrullinated GNS and FLNA, and correlations with ACPA. Serum samples from 46 RA patients and 15 healthy individuals were tested for IgG antibody responses to citrullinated vs uncitrullinated GNS or FLNA. Plates were coated with GNS (FIG. 13A) or FLNA (FIG. 13C) with and without citrullination, and incubated with serum from patients or control subjects, and tested in duplicate. Symbols represent values in individual patients and horizontal lines show mean values. Only significant P-values calculated with an unpaired t test with Welch's correction are indicated. HC, healthy control; RA, rheumatoid arthritis.

FIG. 14 shows protein levels of N-acetylglucosamine-6-sulfatase and filamin A in RA patients and comparison groups.

FIG. 16 show sequence homology between self and microbial peptides.

FIG. 17 show HLA-DR binding prediction for self and microbial peptides. Prediction analysis were performed using the Immune Epitope Database (IEDB) analysis resource consensus tool. A low percentile rank indicates good peptide binders.

DETAILED DESCRIPTION

Figure 1A:
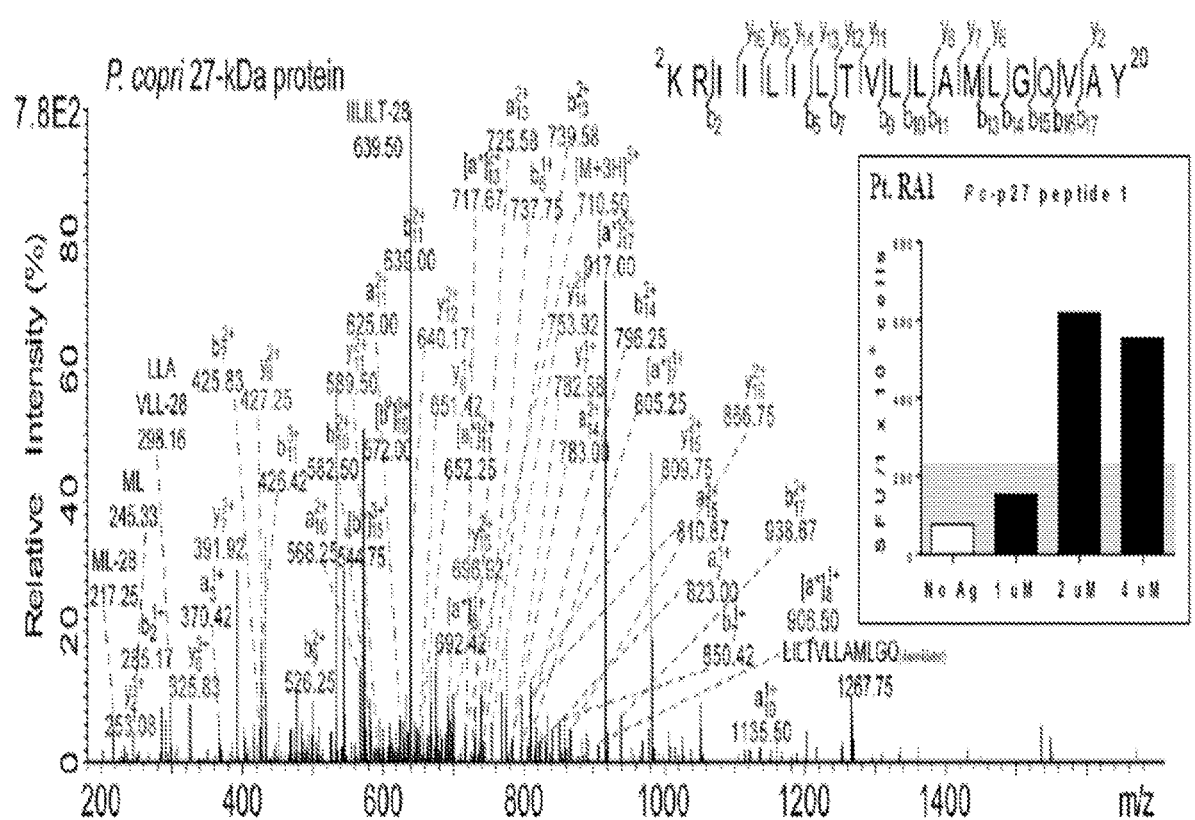
FIGS. 1A-1E show identification and characterization of a broadly immunogenic *P. copri* T cell epitope.

Aspects of invention relate to the identification of peptides presented by HLA-DR molecules (T cell epitope) in PBMC of RA patients, to be derived from a 27 kD protein (Pc-p27) of the intestinal commensal organism *Prevotella copri* (*P. copri*). Aspects of the invention also relate to the findings that *P. copri* induced immune responses to whole organism, protein Pc-p27 and polypeptide fragments thereof. One subgroup of patients was shown to have IgA antibody responses to Pc-p27 or to *P. copri*, correlating with Th17 cytokine responses and frequent anti-citrullinated protein antibodies (ACPA). The other subgroup had IgG *P. copri* antibodies, sometimes with *Prevotella* DNA in synovial fluid, which was associated with *P. copri*-specific Th1 responses and infrequent ACPA. *P. copri* antibody responses were rarely found in patients with other rheumatic diseases for e.g., Lyme disease or in healthy subjects. These findings indicate that *P. copri*, Pc-p27, and immunogenic polypeptides thereof, can be used to identify immunoreactivity in a subject, with that immunoreactivity being indicative of RA disease.

Test antigen for use in the methods and kits herein described include, without limitation, *P. copri* or a portion thereof. In some embodiments the portion of *P. copri* can be protein of *P. copri* or polypeptide fragments thereof. In some embodiments the protein can be full length Pc-p27 and/or polypeptide fragments thereof.

sample obtained from a subject. Positive immunoreactivity will indicate the subject has Rheumatoid arthritis. The deposited strain DSM 18205 is a non-limiting representative strain of *P. copri* which can be used in the assays, methods and kits disclosed herein. A mutant form of the bacterium which retains, at minimum its biological activity of inducing immune reactivity in a subject and or biological sample obtained from a subject as tested by the methods disclosed herein can also be used. In some embodiments the mutant *P. copri* has at least about 70%, 80%, 90%, or 100% immunological reactivity of the wild-type *P. copri*. In some embodiments, the *P. copri* can be one that preferably expresses the protein Pc-p27. The *P. copri* can be obtained from a commercial vendor or purified from a biological sample or grown as a bacterial culture in vitro under routine laboratory conditions known to one skilled in the art. The *P. copri* can be a bacterial cell-suspension which is typically heat inactivated or inactivated and fixed using solutions such as formalin.

The term "portion thereof" as used herein is defined as an antigenic component derived from *P. copri* which retains the ability, at a minimum, to induce immune reactivity in a subject or a biological sample obtained from the subject as determined by methods described herein. In some embodiments, the portion thereof has at least about 70%, 80%, 90%, 100% or more than 100% of the immunological reactivity of whole intact *P. copri* cell. Non limiting examples of antigenic components derived from *P. copri* can be cell wall, cell membranes, proteins, lipoproteins, polysaccharides, nucleic acids. The antigenic portion of *P. copri* of the methods and kits disclosed herein, can be synthetic, recombinant, purified, or contained in a *P. copri* cell extract. Methods to prepare cell extracts i.e., extracts comprising one or more antigenic portions of *P. copri* are known in the art, for example can include solubilization of the bacterial cells or cell lysis by sonication. Methods for obtaining portions of *P. copri* which can be used as test antigens in the methods and kits of the present invention are known to those skilled in the art. In some embodiments, the portion can be *P. copri* protein or one or more polypeptide fragments of the *P. copri* protein. In some embodiments the protein can be Pc-p27 or one or more polypeptide fragment thereof.

The term "Pc-p27" as used herein refers to the full length 27-kD protein of *P. copri* or to a polypeptide fragment or a derivative thereof that retains the ability, at a minimum, to induce immune reactivity in a subject or a biological sample obtained from the subject as determined by methods described herein. The sequence of the full length Pc-p27 is defined by GenBank Accession No. WP_022121928.1, which is incorporated herein by reference in its entirety as SEQ ID NO:1

```
                                                            SEQ ID NO: 1
  1  mkriffiltv  llamlgqvay  aqktcviasa  enhvpireal  ihtnnnhwar  tdyrgywtmr 61  yqfdsatvsk  pgfmkatiry  kelpdtlfll  pdakqlgevt  vwgknqegik  nmeediqeki 121  nslptsstgi  gfdafgwmdk  qgkrdkkhlq  qakkvfekme  hkdpvvaaye  katgkkyelt 181  npydvsafkk  dppsematee  kkatsdaesk  skkkenpeky  aqe
```

As used herein the term *P. copri* refers to the whole intact cell of the gram negative microorganism. In some embodiments of the methods and kits disclosed herein, the whole intact cell of *P. copri* or a portion thereof is used as a test antigen to determine immunoreactivity of a subject or a In some embodiments the "Pc-p27" of the methods and kits described herein can be a polypeptide fragment including or derived from full length Pc-p27 having the amino acid sequence of SEQ ID NO. 1. The polypeptide fragment refers to fragment of the full length Pc-p27 of at least 5, at least 6, at least 7, at least 8, at least 9, at least 10, at least 11, at least 12, at least 13, at least 14, at least 15, at least 16, at least 17, at least 18, at least 19, at least 20 consecutive amino acids of SEQ ID NO:1, that has at least about 70%, 80%, 90%, 100% or more than 100% of the immunological reactivity of Pc-p27 of SEQ ID NO:1. In some embodiments the polypeptide fragment can be signal sequence of Pc-p27. In some embodiments the polypeptide fragment comprises the amino acid sequence; KRIILILTVLLAMLGQVAY (SEQ ID NO: 2), or antigenic portion thereof; DYRGYWTMRYQFD-SATVS (SEQ ID NO: 3) or antigenic portion thereof; EKINSLPTSSTGI (SEQ ID NO: 4) or antigenic portion thereof. In some embodiments the polypeptide fragments are predicted to be presented by HLA-DR molecules associated with rheumatoid arthritis. In one embodiment, the Pc-p27, or fragment thereof, is attached to a solid support matrix, such as a plate for ELISAs, such as in the kits described herein.

One aspect of the invention relates to a method for determining immunoreactivity of a biological sample to one or more of *P. copri* Pc-p27 protein or antigen thereof. Immunoreactivity of a subject to a test antigen (for example protein Pc-p27 or one or more of polypeptide fragments thereof) is determined, for example, by obtaining a biological sample from the subject containing antibodies or immune cells (e.g., T cells), and then assaying that biological sample for test antigen immunoreactivity. A variety of methods are available for determining immunoreactivity to a molecule, a few of which are set forth herein by way of non-limiting example. Immunoreactivity for example can be determined by assaying for B cell reactivity i.e., assaying for presence of antibodies that specifically bind *P. copri* Pc-p27 protein or antigen thereof. Immunoreactivity can also be determined by performing an assay for identification of T cells specifically reactive to *P. copri* Pc-p27 protein or antigen thereof. Accordingly in some embodiments, immunoreactivity can be determined by assaying T cell reactivity and/or B cell reactivity. The determination of which method to utilize can be determined by the skilled practitioner. Immunoreactivity to a molecule (e.g., a protein) can be determined using the full length molecule or one or more representative fragments or epitopes thereof.

In one embodiment, the assay is for the presence of antibodies in the subject that specifically bind to *P. copri* Pc-p27 protein or antigen thereof. The assay involves contacting a biological sample obtained from the subject with the full length protein or representative fragments thereof (referred to as the antigen thereof), under conditions that allow an immunocomplex of the antibody and the polypeptide to form, and then assaying for the presence of the immunocomplex. Various methods of detecting the presence of an antibody-antigen complex are available in the art, and are suitable for use in the methods described herein, such as ELISA, agglutination test, direct immunofluorescence assay, indirect immunofluorescence assay, and immunoblot assay. In one embodiment, the assay involves a detectable label that is used to facilitate detection of the complex through detection of the label. The label present in the test sample is compared to label present in a positive control and/or absent in a negative control. Appropriate controls can be determined by the skilled practitioner. In one embodiment, a negative control is the same type of biological sample obtained, for example, from a healthy subject. In one embodiment, the antibodies can be IgG or IgA type.

Reactivity that indicates a detection of a significant level of the antibody complex above background (e.g., that in a negative control) is expected to serve as a positive result. In one embodiment, reactivity is indicated by detection of the label. In one embodiment, a determination of reactivity that is ≥3 standard deviations (SD) above the mean of samples of healthy control subjects is considered a positive result. In one embodiment, a result that is at least 2-fold above background (e.g., of the signal of a sample obtained from a healthy control subject) is indicative of positive. In one embodiment, higher levels of detection are used to indicate a positive result (e.g., at least 3-fold, 4-fold, or 5-fold above background).

In one embodiment, the assay is for identifying the presence of T cells in the biological sample that are specifically reactive to the *P. copri* Pc-p27 protein or antigen thereof. This is typically accomplished by exposing the cells in the biological sample to a test antigen or one or more representative fragments thereof, and assaying for a response such as stimulation of proliferation. In one embodiment, peripheral blood mononuclear cells (PBMC) or synovial fluid mononuclear cells (SFMC) are contacted with the test antigen in vitro under conditions conducive to stimulation. The cells are then monitored for a response that indicates stimulation. In one embodiment, T cell proliferation in vitro or cytokine production (e.g., IFN-γ) into the supernatant that indicates stimulation is monitored. Identification of a response (e.g., T cell proliferation or cytokine secretion) substantially over that of an appropriate control sample indicates stimulation has occurred. The level of one or more cytokines that are indicative of T cell activation can be monitored in the supernatant of the cells as an indication of T cell activation. One such cytokine is IFN-γ. Other cytokines to monitor include, without limitation IL-17, IL-12, and IL-10. The levels of one or more of such cytokines can be monitored. An increase in IFN-γ, IL-17, and/or IL-12, and/or a decrease in IL-10 levels indicates activation. In one embodiment, the T cell reactivity as determined by T cell response is a Th17 and/or Th1 response. Typically a Th17 response can be indicated by an increase in IL-17 and Th1 response can be indicated by an increase in IFN-γ.

Detection of the stimulation indicates that the sample comprises immunological cells that are immunologically reactive to the test antigen, which in turn indicates that the subject from whom the sample was obtained is immunologically reactive to the test antigen. Put another way, a positive assay result indicate that the test antigen is an autoantigen in the subject. Typical assays for use in this method are T cell proliferation assays, such as 3H-thymdine incorporation assay, CFSE dilution, or an ELISPOT, and also T cell reactivity assays.

Reactivity that indicates a detection of a significant level of stimulation above background (e.g., that in a negative control) is expected to serve as a positive result. In one embodiment, a determination of stimulation that is ≥3 standard deviations (SD) above the mean of samples of healthy control subjects is considered a positive result. In one embodiment, a result that is at least 2-fold above background (e.g., of the signal of a sample obtained from a healthy control subject) is indicative of positive. In one embodiment, higher levels of stimulation is used to indicate a positive result (e.g., at least 3-fold, 4-fold, or 5-fold above background).

One aspect of the invention relates to a method of diagnosing rheumatoid arthritis in a subject by determining whether the subject demonstrates immunological reactivity to *P. copri* or portion thereof, for example proteins such as Pc-p27 or polypeptide fragments thereof. Immunological reactivity of the subject to one or more of *P. copri* or a portion thereof, e.g., protein Pc-p27 or polypeptide fragments thereof, as compared to an appropriate control, indicates the subject has rheumatoid arthritis.

Immunoreactivity of a subject to the *P. copri* is determined, for example, by obtaining a biological sample from the subject containing antibodies or immune cells (e.g., T cells), and then assaying that biological sample for immunoreactivity.

Immunoreactivity to a portion thereof (e.g, a protein) can be determined using the full length molecule or one or more representative fragments or epitopes thereof. The immunological reactivity demonstrated by the subject can be T cell reactivity or B cell reactivity (e.g., has antibodies that specifically bind to the Pc-p27 or polypeptide fragments thereof. T cell and B cell reactivity of a subject to Pc-p27 or polypeptide fragments thereof can be determined by various methods known in the art. Typically, T cell reactivity is performed with an antigenic fragment of the full length molecule. B-cell reactivity can be determined using a full length protein, however in some embodiment, shorter fragments may be used. Any method known in the art can be used to identify the immunological reactivity.

One aspect of the invention relates to a method for diagnosing rheumatoid arthritis in a subject by identifying the presence of antibodies in the subject that specifically bind to *P. copri* or portion thereof, (e.g., protein Pc-p27 or polypeptide fragments thereof. The assay involves contacting a biological sample obtained from the subject with *P. copri* or portion thereof (referred to as the test antigen), under conditions that allow an immunocomplex of the antibody and the test antigen to form, and then assaying for the presence of the immunocomplex. In some embodiments the portion of *P. copri* can be a full length protein of *P. copri* or one or more representative polypeptide fragments thereof. In some embodiments, the protein is Pc-p27 or one or more polypeptide fragments thereof. Various methods of detecting the presence of an antibody-antigen complex are available in the art, and are suitable for use in the methods described herein, such as ELISA, agglutination test, direct immunofluorescence assay, indirect immunofluorescence assay, radioimmunoassay and immunoblot assay. A variety of immunoassay formats may be used to select antibodies specifically immunoreactive with a particular protein, (see, e.g., Harlow & Lane, Antibodies, A Laboratory Manual (1988), for a description of immunoassay formats and conditions that can be used to determine specific immunoreactivity). In one embodiment, the assay involves a detectable label that is used to facilitate detection of the complex through detection of the label. The label present in the test sample is compared to label present in a positive control and/or absent in a negative control. Appropriate controls can be determined by the skilled practitioner. In one embodiment, a negative control is the same type of biological sample obtained, for example, from a healthy subject.

Reactivity that indicates detection of a significant level of the antibody complex above background (e.g., that in a negative control) indicates a positive result. In one embodiment, reactivity is identified by detection of the label. In one embodiment, a determination of reactivity that is ≥3 standard deviations (SD) above the mean of a sample of a healthy control subject is considered a positive result. In one embodiment, a result that is at least 2-fold above background (e.g., of the signal of a sample obtained from a healthy control subject) is indicative of positive. In one embodiment, higher levels of detection are used to indicate a positive result (e.g., at least 3-fold, 4-fold, or 5-fold above background).

One aspect of the invention relates to a method for diagnosing rheumatoid arthritis in a subject by identifying the presence of T cells in the subject that are specifically reactive to *P. copri* or a portion thereof. This is typically accomplished by obtaining a biological sample from the subject that contains PBMC, and exposing the cells in the biological sample to *P. copri* or one or more portion thereof (also referred to as the test antigen), and assaying for a response to the test antigen such as stimulation of proliferation. In one embodiment, peripheral blood mononuclear cells (PBMC) or synovial fluid mononuclear cells (SFMC) of the subject (e.g., in or obtained from the biological sample) are contacted with the test antigen in vitro under conditions conducive to stimulation. The cells are then monitored for a response that indicates stimulation. In one embodiment, T cell proliferation in vitro or cytokine production (e.g., IFN-γ) into the supernatant that indicates stimulation is monitored. Identification of a response (e.g., T cell proliferation or cytokine secretion) substantially over that of an appropriate control sample indicates stimulation has occurred. The level of one or more cytokines that are indicative of T cell activation can be monitored in the supernatant of the cells as an indication of T cell activation. One such cytokine is IFN-γ.

Other cytokines to monitor include, without limitation IL-17, IL-12, and IL-10. The levels of one or more of such cytokines can be monitored. An increase in IFN-γ, IL-17, and/or IL-12, and/or a decrease in IL-10 levels indicates activation. In some embodiments the portion of *P. copri* can be a full length protein of *P. copri* or representative polypeptide fragments thereof. In some embodiments, the protein is Pc-p27 or polypeptide fragments thereof. Detection of the stimulation indicates that the sample comprises immunological cells that are immunologically reactive to the test antigen, which in turn indicates that the subject from whom the sample was obtained is immunologically reactive to the test antigen. Put another way, a positive assay result indicates that the test antigen is an autoantigen in the subject, and that the subject has rheumatoid arthritis. Typical assays for use in this method are T cell proliferation assays, such as 3H-thymdine incorporation assay, CFSE dilution, or an ELISPOT, and also T cell reactivity assays. Methods of determining T cell reactivity are well known in the art and are described in for example U.S. Pat. No. 5,750,356A.

Reactivity that indicates a detection of a significant level of stimulation above background (e.g., that in a negative control) is expected to serve as a positive result. In one embodiment, a determination of stimulation that is ≥3 standard deviations (SD) above the mean of a sample of a healthy control subject is considered a positive result. In one embodiment, a result that is at least 2-fold above background (e.g., of the signal of a sample obtained from a healthy control subject) is indicative of positive. In one embodiment, higher levels of stimulation is used to indicate a positive result (e.g., at least 3-fold, 4-fold, or 5-fold above background).

Test antigen for use in the methods and kits herein described include, without limitation, *P. copri* or a portion thereof. In some embodiments the portion of *P. copri* can be protein of *P. copri* or polypeptide fragments thereof. In some embodiments the protein can be full length Pc-p27 and/or polypeptide fragments thereof. The sequence of the full length Pc-p27 is defined by GenBank Accession No. WP_022121928.1, which is incorporated herein by reference in its entirety as SEQ ID NO:1.

In some embodiments the "Pc-p27" of the methods and kits described herein can be a polypeptide fragment including or derived from full length Pc-p27 having the amino acid sequence of SEQ ID NO. 1. The polypeptide fragment refers to fragment of the full length Pc-p27 of at least 5, at least 6, at least 7, at least 8, at least 9, at least 10, at least 11, at least 12, at least 13, at least 14, at least 15, at least 16, at least 17, at least 18, at least 19, at least 20 consecutive amino acids of SEQ ID NO:1, that has at least about 70%, 80%, 90%, 100% or more than 100% of the immunological reactivity of Pc-p27 of SEQ ID NO:1. In some embodiments the polypeptide fragment can be signal sequence of Pc-p27. In some embodiments the polypeptide fragment comprises the amino acid sequence; KRIILILTVLLAMLGQVAY (SEQ ID NO: 2), or antigenic portion thereof; DYRGYWTMRYQFD-SATVS (SEQ ID NO: 3) or antigenic portion thereof; EKINSLPTSSTGI (SEQ ID NO: 4) or antigenic portion thereof. In some embodiments the polypeptide fragments are predicted to be presented by HLA-DR molecules associated with rheumatoid arthritis.

The polypeptide and encoding nucleic acid sequences of Pc-p27 are publically available e.g., from the NCBI website. The Pc-p27 or a polypeptide fragment can be a homolog of *P. copri* Pc-p27 or a polypeptide fragment thereof. In some embodiments, the Pc-p27 polypeptide has an amino acid sequence at least 85%, at least 90%, at least 95%, at least 97% or at least 99% identical to the amino acid sequence of SEQ ID NO:1 and has at least about 70%, 80%, 90%, 100% or more than 100% of the immunological reactivity of Pc-p27 of SEQ ID NO:1. In some embodiments, the Pc-p27 polypeptide has an amino acid sequence that has at least 85%, at least 90%, at least 95%, at least 97% or at least 99% amino acid sequence homology to amino acid sequence of SEQ ID NO:1 and has at least about 70%, 80%, 90%, 100% or more than 100% of the immunological reactivity of Pc-p27 of SEQ ID NO:1. In some embodiments, the Pc-p27 is a polypeptide fragment of SEQ ID NO:1 of at least 5, at least 6, at least 7, at least 8, at least 9, at least 10, at least 11, at least 12, at least 13, at least 14, at least 15, at least 16, at least 17, at least 18, at least 19, at least 20 consecutive amino acids of SEQ ID NO:3, that has at least about 70%, 80%, 90%, 100% or more than 100% of the immunological reactivity of Pc-p27 of SEQ ID NO:1.

Percent (%) amino acid sequence identity for a given polypeptide sequence relative to a reference sequence is defined as the percentage of identical amino acid residues identified after aligning the two sequences and introducing gaps if necessary, to achieve the maximum percent sequence identity, and not considering any conservative substitutions as part of the sequence identity. Percent (%) amino acid sequence homology for a given polypeptide sequence relative to a reference sequence is defined as the percentage of identical or strongly similar amino acid residues identified after aligning the two sequences and introducing gaps if necessary, to achieve the maximum percent homology. Non identities of amino acid sequences include conservative substitutions, deletions or additions that do not affect immunological reactivity of Pc-p27. Strongly similar amino acids can include, for example, conservative substitutions known in the art. Percent identity and/or homology can be calculated using alignment methods known in the art, for instance alignment of the sequences can be conducted using publicly available software such as BLAST, Align, ClustalW2. Those skilled in the art can determine the appropriate parameters for alignment, but the default parameters for BLAST are specifically contemplated.

The immunological reactivity can be determined by T cell reactivity or B cell response to Pc-p27 and one or more of polypeptide fragments thereof by the skilled practitioner by assays known in the art, some of which are described herein. Examples of assays for T cell reactivity include, without limitation, measurement of in vitro T cell proliferation, measurement of in vitro IFN-γ secretion, induced in PBMC or SFMC of the subject in response to Pc-p27 (e.g., using an immunogenic polypeptide fragment). Example of assays for B cell responses include, without limitation, detection and/or measurement of antibodies in a biological sample that specifically recognize and/or specifically bind to Pc-p27. Examples of assays for T cell reactivity include, without limitation, measurement of T cell proliferation and IFN-γ secretion by PBMC or SFMC of the subject by Pc-p27 in vitro.

The entire full length protein Pc-p27 or protein fragments can be used in the assays described herein. Combinations of full length protein and protein fragments can also be used, as can combinations of proteins/fragments that represent the different antigens (e.g., testing for one or more of Pc-p27 and other known RA autoantigens reactivity in the same assay, or side by side in the same patient). The appropriate polypeptide or fragment thereof for use in the specific method can be determined by the skilled practitioner. The proteins or fragments can be recombinant, purified, isolated, naturally occurring or synthetically produced. The term "recombinant" when used in reference to a nucleic acid, protein, cell or a vector indicates that the nucleic acid, protein, vector or cell containing them have been modified by introduction of a heterologous nucleic acid or protein or the alteration of a native nucleic acid or a protein, or that the cell is derived from a cell so modified. The term "heterologous" (meaning 'derived from a different organism') refers to the fact that often the transferred protein was initially derived from a different cell type or a different species from the recipient. Typically the protein itself is not transferred, but instead the genetic material coding for the protein (often the complementary DNA or cDNA) is added to the recipient cell. Methods of generating and isolating recombinant polypeptides are known to those skilled in the art and can be performed using routine techniques in the field of recombinant genetics and protein expression. For standard recombinant methods, see Sambrook et al, Molecular Cloning: A Laboratory Manual, Cold Spring Harbor Laboratory Press, NY (1989); Deutscher, Methods in Enzymology 182:83-9 (1990); Scopes, Protein Purification: Principles and Practice, Springer-Verlag, NY (1982).

Either the full length protein, or protein fragments derived from the full length protein, can be used to identify immunoreactivity of a subject to the proteins disclosed herein. The specific molecules used in the assays described herein (e.g., full length protein(s), representative fragments thereof, or a combination of the full length and fragments) are referred to as the "test antigen" in the assay descriptions. Which fragments of a full length protein to use in the assay can be determined by the skilled practitioner. Typically, a cocktail of fragments derived from the same protein are used for determination of reactivity of a subject to that protein. Depending upon the length, the number of different protein fragments can be determined and optimized by the skilled practitioner. In one embodiment, 2 or more protein fragments are used. In one embodiment, 3 or more, 4, 5, 6, 7, 8, 9, or 10 or more protein fragments are used. In one embodiment, a protein fragment is at least 8 amino acids in length (e.g., ≥8, ≥9, ≥10, ≥11, ≥12, ≥13, ≥14, ≥15 amino acids).

Specific protein fragments can be identified for use in the herein described methods such as those predicted for presentation by HLA-DR molecules. Such protein fragment can be identified by the methods described in the examples and also by a variety of software programs available to the skilled practitioner (Lin et al. BMC Immunology 2008, 9:8). In one embodiment, TEPITOPE 2000 (Sturniolo et al. 1999 Nature Biotechnology. 17; 555-561) is used. Other freely accessible online programs offered by the Immune Epitope Database and Analysis Resource (http://www.iedb.org/) are also available.

Examples of specific protein fragments of Pc-p27 include, without limitation KRIILILTVLLAMLGQVAY (SEQ ID NO: 2), or antigenic portion thereof; DYRGYWTM-RYQFDSATVS (SEQ ID NO: 3) or antigenic portion thereof; EKINSLPTSSTGI (SEQ ID NO: 4) or antigenic portion thereof; and combinations thereof.

In one embodiment, reactivity in a subject to other suspected autoantigens is also performed in combination with the herein described assays. One such autoantigen is cyclic citrullinated peptide (CCP). Several assays for detecting anti-citrullinated protein antibody (ACPAs) are known in the art employing mutated citrullinated Vimentin (MCV-assay), filaggrin-derived peptides (CCP-assay) and viral citrullinated peptides (VCP-assay). Methods for determination of reactivity of a subject for anti-CCP and/or other markers for disease diagnosis are known in the art. Non limiting examples include WO 2005/085858 discloses a method of assessing RA by measuring CCP and serum amyloid A (SAA). WO 2005/064307 and US 2007/0264673 assess RA by measuring CCP and IL-6. WO 2005/029091 and US 2006/094056 provide methods to diagnose, treat, or evaluate inflammatory/autoimmune diseases such as RA by sampling fluids from a human with a suspected diagnosis by detecting CCP. US 2007/0148704 and WO 2007/039280 disclose use of CCP and antibodies as biomarkers in diagnosing RA. WO 2006/008183 discloses various biomarkers for RA.

Symptoms of RA

A subject suspected of having rheumatoid arthritis can be tested by the methods described herein. The subject may exhibit one or more symptoms of rheumatoid arthritis prior to performance of the methods. Rheumatoid arthritis (RA) is an autoimmune disease that causes the body's immune system to attack joint tissues, which leads to inflammation of joint lining. Inflammation of the joints is the primary manifestation of RA. Early symptoms of RA include affected joints being swollen, tender, warm, painful and stiff especially in the morning. The stiffness is shown to last for at least an hour. The pain associated with RA is induced at the site of inflammation. Non limiting examples of other symptoms for RA include presence of rheumatoid nodules in the skin, fatigue, joint deformity and reduction in range of motion of affected joints, dryness of eyes and mouth. Early symptoms associated with RA are also seen in patients with other autoimmune related disease such osteoarthritis, fibromyalgia, lupus. Accordingly, in some embodiments of the present invention, the subject exhibits symptoms of RA and/or other autoimmune related disease manifestation known in the art e.g., Tenosynovitis, osteoporosis, carpal tunnel syndrome.

Diagnosis of Rheumatoid Arthritis in a Subject

There is no unique test or feature that is pathognomonic for RA. Rather, the diagnosis is made by recognizing a pattern of signs and symptoms. Classification criteria based on symptoms for identifying subjects suffering to early stages of RA and therefore aiding in disease diagnosis are known in the art and are for example set forth in 1987 American College of Rheumatology (ACR) criteria (Arnett et al; 1987) and recently 2010 criteria by ACR and the European League Against Rheumatism (EULAR) (Aletaha et al; 2010).

The diagnostic methods of RA includes X-ray, MRI and/or ultrasound imaging of the affected joints and blood/serological tests. Non limiting examples of blood/serology tests known in the art to be conducted for diagnosis of RA include measurements of; Erythrocyte Sedimentation Rate (ESR), Rheumatoid factor (RF), Anti-cyclic Citrullinated Peptide (anti-CCP), Antinuclear Antibody (ANA), Uric Acid, complete blood count: measures the numbers of red and white cells in your blood, C-reactive protein (CRP). In RA, 10 HLA-DR alleles with a shared epitope, including the HLA-DRB1*0101 and 0401 alleles (Sturniolo et al., 1999) convey the greatest risk. Accordingly, in some embodiments, the subject has been or is further tested for one or more of RF, ACPA, and one or more of HLA-DR alleles. Non-limiting examples of HLA-DR alleles that can be tested for include HLA-DRB1*0101, HLA-DRB1*0401.

In some embodiments, identification of immunoreactivity to *P. copri* or portion thereof described herein can be used in diagnosis of RA. In some embodiments, the methods disclosed herein can be used to identify a patient with RA. In some embodiments, the methods disclosed herein can be used for differential diagnosis of RA. Immunoreactivity of a subject to one or more of the proteins can determined in vitro using suitable biological samples disclosed herein by a variety of methods available to the skilled practitioner.

The discoveries presented herein indicate that reactivity to *P. copri* or portion thereof can be used as a biomarker for the diagnosis of a condition (e.g., RA and associated symptoms). More specifically, subject immunoreactivity (e.g., antigen reactive T cells, and/or antibody response to antigen) is indicative of the condition. As such, another aspect of the invention relates to a method of diagnosing the condition in a subject (e.g., RA) by determining whether the subject is immunologically reactive with *P. copri* or portion thereof by the herein described methods. The determination may be made in conjunction with the presence of other such symptoms of the condition present in the subject, for example, arthritic symptoms in a subject, or neurologic symptoms in a subject, or cardiac symptoms in a subject. The determination of immunological reactivity of a subject, as compared to an appropriate control, indicates the subject has, or is likely to develop, the condition. The condition can be further confirmed by the determination of immunological reactivity to additional proteins such as antibodies to citrullinated peptides (ACPA), antinuclear antibody (ANA), anti-neutrophil cytoplasmic antibodies (ANCA) and presence of rheumatoid factors and other diagnostic tests known to those skilled in the art and described above. In some embodiments, the subject can test negative for one or more of RF, ACPA, *Prevotella* DNA in their synovial fluid, and or more HLA-DR alleles.

Various assays can be used to identify antibodies present in a serum sample that bind the test antigen (e.g., ELISA, agglutination test, direct immunofluorescence assay, indirect immunofluorescence assay, western blot, an immunoblot assay). For example, the assay could be an immunoblot that carries a recombinant test antigen (full length or peptide fragment(s)).

The methods described herein can also include determination of rheumatoid factor, ACPA and/or ANA. For example, the test antigens disclosed herein can be included in or used in conjunction with an assay such as the Sure-Vue® RF (Fishersci), RFscan™ Card Test Kit (BD Biosciences), Anti-Rheumatoid Factor IgM ELISA Kit (abcam), AVITEX®-RF (Omega diagnostics) Citrullinated Protein Antibodies IgG ELISA Kit (Omega diagnostics) Anti-CCP EIA (Bio-Rad), BioPlex® 2200 Anti-CCP (Bio-Rad), CCPoint® (Eurodiagnostica), DIASTAT® anti-nuclear antibody (ANA) test (Eurodiagnostica), DIASTATR PR3-ANCA® (Eurodiagnostica). The methods described herein can also include determination of one or more of immunological reactivity to filamin-A, immunological reactivity to N-acetylglucosamine-6-sulfatase, such as disclosed in International Patent Publication WO 2016/183310, the contents of which are incorporated herein by reference.

Test-antigen reactive T cells in PBMC and SFMC can be assessed using a number of assays. For example, reactive T cells in PBMC and SFMC can be assessed using tetramer reagents comprising recombinant HLA-DR molecules and test antigen epitopes.

The test antigen may comprise naturally occurring or analog or derivative amino acids, as long as the immunoreactive or immunostimulatory nature of the peptide is retained to sufficient degree to allow T cell activation and/or antibody binding. Thus, some amino acids may be added to or subtracted from the native protein or polypeptide fragments as known in the art. Additionally, some amino acids of the native human protein or polypeptide fragments may be substituted with amino acids that occur in other species, or be substituted as known in the art. Amino acid substitution exchange groups and empirical similarities between amino acid residues, can be found in standard texts such as Schulz et al., Principles of Protein Structure, 14 16 (Springer-Verlag, New York, 1979). There is a limit to how much substitution can be tolerated before the original tertiary structure is lost. Typically, tertiary structure conservation would be lost when the amino acid sequence varies by more than 50%. See, e.g., Chothia & Lesk, Relation between the divergence of sequence & structure in proteins, 5 EMBO J. 823 (1986).

Guidance concerning which amino acid changes are likely to be phenotypically silent is found in Bowie et al., 247 Science 1306 (1990). Amino acids that are essential for function can be identified by methods known in the art, such as site-directed mutagenesis or alanine-scanning mutagenesis. Cunningham et al., 244 Science 1081 (1989). The latter procedure introduces single alanine mutations at every residue in the molecule. The resulting mutant molecules are then tested for biological activity such as antibody binding and/or T cell stimulation. Sites that are critical for ligand-receptor binding can also be determined by structural analysis such as crystallography, nuclear magnetic resonance, or photoaffinity labeling. Smith et al., 224 J. Mol. Biol. 899 (1992); de Vos et al., 255 Science 306 (1992).

The genes and encoded proteins of the autoantigens described herein have been sequenced and are available at numerous sources. Further, the genes are conserved in human, chimpanzee, rat, and zebrafish. Hence, these peptides can include those derived from non-human sources or appropriate sequence information. In an aspect of the invention, the test peptide is predicted to be presented by HLA-DR molecules associated with chronic inflammatory arthritis (e.g., RA). In some embodiments the peptide of the present invention can be presented by one or more HLA-DR disclosed in reference (Sturniolo et al., 1999), the contents of which are incorporated herein in its entirety.

As noted above, generally, amino acid substitutions should be made conservatively; i.e., a substitute amino acid should replace an amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. Variants within the scope of this invention may also, or alternatively, contain other modifications, including the deletion or addition of amino acids, that have minimal influence on the stimulatory properties, antibody binding, tertiary structure of the peptide. Thus, for example, conservative substitutions in a protein fragment can be made with the proviso that functional activity is retained to a meaningful degree such that the particular assay (e.g., T cell reactivity or immunoassay) works as intended to provide evidence in diagnosing subjects (e.g., with RA).

Moreover, peptides often contain amino acids other than the twenty "naturally occurring" amino acids. Further, many amino acids, including the terminal amino acids, may be modified by natural processes, such as processing and other post-translational modifications, or by chemical modification techniques well known in the art. Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as Creighton, PROTEINS—STRUCTURE & MOLECULAR PROPERTIES (2nd ed., W. H. Freeman & Co., New York, 1993). Many detailed reviews are available on this subject, such as by Wold, POSTTRANSLATIONAL COVALENT MODIFICATION OF PROTEINS, 1-12 (Johnson, ed., Academic Press, New York, 1983); Seifter et al. 182 Meth. Enzymol. 626 (1990); Rattan et al., 663 Ann. N.Y. Acad. Sci. 48 (1992). Accordingly, the peptides of the present invention also encompass derivatives or analogs in which a substituted amino acid residue is not one encoded by the genetic code.

Further, "derivatives" of a test antigen contain additional chemical moieties not normally a part of the protein. Covalent modifications of the autoantigens are included within the scope of this invention. Such modifications may be introduced into the molecule by reacting targeted amino acid residues of the antibody with an organic derivatizing agent that is capable of reacting with selected side chains or terminal residues. For example, derivatization with bifunctional agents, well-known in the art, is useful for cross-linking the antigen or fragment to a water-insoluble support matrix or to other macromolecular carriers. Derivatives also include radioactively labeled peptides that are labeled, for example, with radioactive iodine ($^{125}I$, $^{131}I$), carbon ($^{14}C$), sulfur ($^{35}S$), tritium ($^{3}H$) or the like; conjugates of peptides with biotin or avidin, with enzymes, such as horseradish peroxidase, alkaline phosphatase, (β-D-galactosidase, glucose oxidase, glucoamylase, carboxylic acid anhydrase, acetylcholine esterase, lysozyme, malate dehydrogenase or glucose 6-phosphate dehydrogenase; and also conjugates of monoclonal antibodies with bioluminescent agents (such as luciferase), chemoluminescent agents (such as acridine esters), or fluorescent agents (such as phycobiliproteins).

Structural analogs of the autoantigens identified herein are provided by known method steps based on the teaching and guidance presented herein. Knowledge of the three-dimensional structures of proteins is crucial in understanding how they function. The three-dimensional structures of hundreds of proteins are currently available in protein structure databases (in contrast to the thousands of known protein sequences in sequence databases). Analysis of these structures shows that they fall into recognizable classes of motifs. It is thus possible to model a three-dimensional structure of a protein based on the protein's homology to a related protein of known structure. Many examples are known where two proteins that have relatively low sequence homology, can have very similar three dimensional structures or motifs.

It is possible to determine the three dimensional structures of proteins of up to about 15 kDa by nuclear magnetic resonance (NMR). The technique only requires a concentrated solution of pure protein. No crystals or isomorphous derivatives are needed. The structures of a number of proteins have been determined by this method. The details of NMR structure determination are well-known in the art. See, e.g., Wuthrich, NMR of Proteins & Nucleic Acids (Wiley, N.Y., 1986); Wuthrich, 243 Science 45 (1989); Clore et al., 24 Crit. Rev. Bioch. Molec. Biol. 479 (1989); Cooke et al., 8 Bioassays 52 (1988).

Thus, according to the present invention, use of NMR spectroscopic data can combined with computer modeling to arrive at structural analogs of at least portions of the autoantigen (peptides or epitopes) based on a structural understanding of the topography. Using this information, one of ordinary skill in the art can achieve structural analogs of the autoantigens such as by rationally-based amino acid substitutions allowing the production of peptides in which the binding affinity or avidity is modulated in accordance with the requirements of the expected diagnostic use of the molecule, for example, the achievement of greater binding specificity or affinity.

The herein described methods may further be used to indicate a therapy for the subject who tests positive. The identification of immunoreactivity to *P. copri*, portion derived from it e.g., to protein Pc-p27 or polypeptide fragments thereof in RA, as provided herein, is an important addition to the clinician's arsenal in combating chronic inflammatory arthritis, and assists the clinician in choosing the course of therapy. For example, when RA is diagnosed, nonsteroidal anti-inflammatory drugs (NSAIDs) (e.g., ibuprofen, naproxen sodium) or steroids (e.g., corticosteroid medication such as prednisone); or disease modifying antirheumatic drugs (DMARDs), such as hydroxychloroquine, sulfasalzine or methotrexate, may be prescribed. DMARDs can be synthetic or biologic in nature. Additionally or alternatively, anti-TNF therapy (e.g., HUMIRA® (adalimumab), ENBREL® (etanercept), may be beneficial. Other non-limiting examples include Orencia® (abatacept), Kineret® (anakinra), Certolizumab® (Cimzia), Simponi® (golimumab), Remicade® (infliximab), Actemra® (tocilizumanb) and Xelijanz® (tofacitinib).

It is also contemplated that *P. copri*—directed therapy, such as targeting *P. copri* with antibiotics, consumption of probiotic supplements may also be beneficial. In one embodiment, the subject is provided one or more therapies following an indication that they are immunoreactive to an autoantigen. As such, another aspect of the invention relate to a method of treating a subject diagnosed with a RA. The method comprises diagnosing the subject for the disorder by one or more of the herein described methods, and then treating the subject for said condition. Diagnosis may further include assessing the subject for other symptoms such as a neurological condition or heart condition typically seen with secondary RA symptoms. In some embodiments of the present invention, the methods to determine immunoreactivity to autoantigens disclosed herein can be conducted prior to, during and/or after a therapeutic treatment and therefore aid in assessment of effectiveness of the treatment and/or monitor disease progression.

Another aspect of the invention relates to a kit for identifying a subject with a condition such as rheumatoid arthritis. (e.g., citrullinated protein/peptides such as citrullinated filaggrin, fibrinogen, fibronectin, α-enolase, collagen type II, histones, vimentin). The kit comprises one or more of *P. copri* or a portion thereof as test antigens. In some embodiments the portion of *P. copri* can be protein of *P. copri* or a polypeptide fragment thereof. In some embodiments the protein can be Pc-p27 or one or more polypeptide fragments thereof, such as a set of synthesized peptides, fragments, or epitopes thereof. In some embodiments the kit further comprises reagents necessary for conducting an assay capable of detecting the presence of immunoreactivity of a subject to that test antigen (e.g., an antibody in a sample obtained from said subject that binds to Pc-p27 or polypeptide fragment thereof). The kit can be designed for any of the various assays described herein. In one embodiment, the assay in the kit is an enzyme-linked immunosorbent assay (ELISA) or immunoblot, the components for which are well-known in the art. The peptides may be synthesized or obtained from natural or recombinant sources, each of which is well-known in the art. The kit may further include other autoantigens (e.g, citrullinated protein or fragments/epitopes thereof) known in the art, such as those described herein.

In some embodiments, the kit can further comprise reagents for conducting an assay for detecting the presence of one or more cytokines and/or chemokines. Non-limiting examples of cytokines and/or chemokines that can be assayed include one or more of IL-23, IL-22, IL-17E, IL-17F IFN-γ, TNF, IFN-α, MIP-1α, MMP-1β, IL-17F, IL-1β, CXCL9, CXCL10, IL-12. In some embodiments, the kit can further comprise *E. coli* and/or *B. fragilis* whole cells or potential antigen derived from it. In some embodiments, the kit can also include components to assay for *Prevotella* DNA in the biological sample. Methods to assay *Prevotella* DNA in a biological sample are disclosed herein and are known in the art for example in WO2013056222A1, the teachings of which are incorporated herein in its entirety. The kit may alternately further comprise buffers, enzymes, and/or containers for performing the reactions or analyses. The various reagents within the kit may be provided separately or together as is convenient in a container such as a vial, test tube, flask, bottle or even syringe. The components may be suitably aliquotted for performance of the methods. The kit may further contain one or more positive and/or negative controls. The antigens or other components of the kit may be labeled with a detectable marker. In some embodiments the kit can be used to identify a patient with new onset rheumatoid arthritis or chronic rheumatoid arthritis.

In some embodiments, the subject is further tested for *Prevotella* DNA in their synovial fluid. Assays for *P. copri* DNA in a biological sample are disclosed herein and are known in the art for example in WO2013056222A1, the teachings of which are incorporated herein in its entirety. In some embodiments, the subject tests negative for *Prevotella* DNA. In some embodiments, the subject can test positive for *Prevotella* DNA. In some embodiments the test antigens can be included in kit for use in differential diagnosis of rheumatoid arthritis and other diseases for example for Lyme disease. Accordingly, the test antigens of the present invention can be used in conjunction with an assay such as the *Borrelia* ViraStripe® IgG, IgM test kit (Viramed Biotech AG, Planegg, Germany). The *Borrelia* ViraStripe® is an immunoblot that carries native, purified antigens from *Borrelia afzelii* (Pko), *Borrelia burgdorferi sensu stricto*, and recombinant *Borrelia* antigen VlsE. Alternatively, the test antigen may be included in or used in conjunction with an immunoassay such as the *Borrelia* B31 ViraBlot® Western blot test kits (Viramed Biotech AG, Planegg, Germany) which identify anti-*Borrelia* antigen-binding IgG and/or IgM in the serum of suspected *Borrelia*-infected patients.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used to described the present invention, in connection with percentages means±1%.

In one respect, the present invention relates to the herein described compositions, methods, and respective component(s) thereof, as essential to the invention, yet open to the inclusion of unspecified elements, essential or not ("comprising). In some embodiments, other elements to be included in the description of the composition, method or respective component thereof are limited to those that do not materially affect the basic and novel characteristic(s) of the invention ("consisting essentially of"). This applies equally to steps within a described method as well as compositions and components therein. In other embodiments, the inventions, compositions, methods, and respective components thereof, described herein are intended to be exclusive of any element not deemed an essential element to the component, composition or method ("consisting of").

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The present invention may be as defined in any one of the following numbered paragraphs:

1. A method for determining whether a biological sample comprising antibodies and/or immunological cells obtained from a subject is immunologically reactive with *P. copri* Pc-p27 protein or antigen thereof, comprising performing an assay for identifying the presence of antibodies that specifically bind *P. copri* Pc-p27 protein or antigen thereof or performing an assay for identifying T cells specifically reactive to *P. copri* Pc-p27 protein or antigen thereof, and determining the sample is reactive with the *P. copri* Pc-p27 protein or antigen thereof if the assay produces positive results compared to an appropriate control.
2. The method of paragraph 1, wherein the assay that identifies the presence of the antibodies comprises contacting the sample with *P. copri* Pc-p27 protein or antigen thereof, under conditions that allow an immunocomplex of the antibody and the *P. copri* Pc-p27 protein or antigen thereof to form, and detecting the presence or absence of the immunocomplex, wherein the presence of the immunocomplex indicates the biological sample is immunoreactive with the *P. copri* Pc-p27 protein or antigen thereof and wherein the absence of the immunocomplex indicates the biological sample is not immunoreactive with the *P. copri* Pc-p27 protein or antigen thereof.
3. The method of any one of paragraphs 1-2, wherein the antibodies are IgG or IgA.
4. The method of any one of paragraphs 1-3, wherein the assay is an ELISA, agglutination test, direct immunofluorescence assay, indirect immunofluorescence assay, or an immunoblot assay.
5. The method of paragraph 1, wherein the assay for identifying T cells specifically reactive to *P. copri* Pc-p27 protein or antigen thereof comprises:
    a. stimulating peripheral blood mononuclear cells (PBMC) of the subject or the synovial fluid mononuclear cells (SFMC) of the subject in vitro with *P. copri* Pc-p27 protein or antigen thereof;
    b. measuring T cell proliferation in vitro or secretion of IFN-γ into cell culture supernatants; and
    c. identifying the subject as having T cells specifically reactive to *P. copri* Pc-p27 protein or antigen thereof, when T cell proliferation or secretion of IFN-γ measured is substantially increased over that of an appropriate control.
6. The method of any one of paragraphs 1 or 5, wherein the assay is a T cell proliferation assay.
7. The method of paragraph 6, wherein the assay is a $^3$H-thymdine incorporation assay, CFSE dilution, or an ELISPOT.
8. The method of any one of paragraphs 1 or 4, wherein the assay is a T cell reactivity assay.
9. The method of any one of paragraphs 1-8, wherein said biological sample is obtained from peripheral blood, synovial fluid, synovial tissue, peripheral blood mononuclear cells (PBMC), or synovial fluid mononuclear cells (SFMC).
10. A method of diagnosing Rheumatoid arthritis in a subject comprising determining whether the subject is immunologically reactive with *P. copri* or a portion thereof, wherein immunological reactivity of the subject to *P. copri* or a portion thereof as compared to an appropriate control, indicates the subject has Rheumatoid arthritis.

11. The method of paragraph 10, wherein determining is by evaluating a biological sample obtained from the subject for immunological reactivity with the *P. copri* or a portion thereof.
12. The method of any one of paragraphs 10-11, wherein determining immunological reactivity is by detecting a T cell response to *P. copri* or a portion thereof in the subject by processing a biological sample obtained from the subject.
13. The method of paragraph 12, wherein detecting a T cell response is by detecting the presence of T cells reactive to *P. copri* or a portion thereof.
14. The method of paragraph 12 wherein the T cell response is a Th17 response.
15. The method of any one of paragraphs 13 or 14, wherein detecting the presence of T cells comprises:
    a. stimulating peripheral blood mononuclear cells (PBMC) of the subject or the synovial fluid mononuclear cells (SFMC) of the subject in vitro with *P. copri* or a portion thereof; and
    b. measuring T cell proliferation in vitro or secretion of IFN-γ into cell culture supernatants;
    c. identifying the subject as having T cells reactive to *P. copri* or a portion thereof when T cell proliferation or secretion of IFN-γ is measured as significantly increased over that of an appropriate control.
16. The method of any one of paragraphs 10-11, wherein determining immunological reactivity comprises determining if the subject has a B-cell response to *P. copri* or a portion thereof resulting in the production of antibodies that specifically recognize the *P. copri* or a portion thereof, by contacting the sample with the *P. copri* or a portion thereof, under conditions that allow an immunocomplex of the antibody and the *P. copri* or a portion thereof to form, and detecting the presence or absence of an immunocomplex, wherein the presence of an immunocomplex indicates the subject presents a B-cell response to the *P. copri* or a portion thereof and wherein the absence of an immunocomplex indicates the subject fails to present a B-cell response to the *P. copri* or a portion thereof.
17. The method of paragraph 16, wherein the assay is an enzyme-linked immunosorbent assay (ELISA), agglutination test, direct immunofluorescence assay, indirect immunofluorescence assay, or an immunoblot assay.
18. The method of any one of paragraphs 11-17, wherein said biological sample is obtained from peripheral blood, synovial fluid, synovial tissue, peripheral blood mononuclear cells (PBMC), or synovial fluid mononuclear cells (SFMC).
19. The method of any one of paragraphs 1-18, wherein the portion of *P. copri* is a protein or polypeptide fragment(s) of *P. copri*.
20. The method of paragraph 19, wherein the protein is Pc-p27 whole protein or polypeptide fragment(s) thereof.
21. The method of any one of paragraphs 1-20, wherein the Pc-p27 polypeptide fragment is predicted to be presented by HLA-DR molecules associated with chronic inflammatory arthritis
22. The method of any one of paragraphs 1-21, wherein the polypeptide fragment is selected from the group consisting of KRIILILTVLLAMLGQVAY (SEQ ID NO: 2), or antigenic portion thereof; DYRGYWTMRYQFDSATVS (SEQ ID NO: 3) or antigenic portion thereof; EKINSLPTSSTGI (SEQ ID NO: 4) or antigenic portion thereof; and combinations thereof.
23. The method of any one of paragraphs 1-22, wherein the subject exhibits symptoms of arthritis or other autoimmune related disease manifestation.
24. The method of any one of paragraphs 1-23, wherein the subject is suspected of having Rheumatoid arthritis.
25. The method of any one of paragraphs 1-23, wherein the subject is suspected of having or suffers from new onset rheumatoid arthritis or chronic rheumatoid arthritis.
26. The method of any one of paragraphs 1-25, wherein the subject has been further tested for one or more of rheumatoid factor (RF), anti-citrullinated protein antibodies (ACPA), *Prevotella* DNA in their synovial fluid, immunological reactivity to filamin-A, immunological reactivity to N-acetylglucosamine-6-sulfatase, and one or more HLA-DR alleles.
27. The method of any one of paragraphs 1-26, wherein the subject is further tested for *P. copri* in a biological sample of the subject.
28. The method of paragraph 27, wherein the biological sample is synovial fluid or serum, and the subject is tested for the presence of *P. copri* 16S rDNA.
29. The method of any one of paragraphs 1-28, wherein the subject tests positive for one or more of (RF), (ACPA), *Prevotella* DNA in their synovial fluid, immunological reactivity to filamin-A, immunological reactivity to N-acetylglucosamine-6-sulfatase, and one or more HLA-DR alleles.
30. The method of any one of paragraphs 1-29, wherein the subject tests negative for one or more of (RF), (ACPA), *Prevotella* DNA in their synovial fluid, immunological reactivity to filamin-A, immunological reactivity to N-acetylglucosamine-6-sulfatase, and one or more HLA-DR alleles.
31. The method of paragraph 30, wherein the HLA-DR allele is HLA-DRB1*0101 and/or HLA-DRB1*0401.
32. The method of any one of paragraphs 1-31, further comprising the step of treating the subject who comprises the antibodies and/or immune cells for rheumatoid arthritis.
33. The method of paragraph 32 wherein treating is by administration of a therapeutically effective amount of one or more of a nonsteroidal anti-inflammatory drug (NSAIDs), a steroid, a disease modifying anti-rheumatic drug (DMARD), an antibiotic, and a biologic, to the subject.
34. A kit comprising, one or more of *P. copri* or a portion thereof, and reagents for conducting an assay for detecting the presence of an antibody in a sample that binds to the one or more of *P. copri* or a portion thereof.
35. The kit of paragraph 34, further comprises reagents for conducting an assay for detecting the presence of one or more cytokines or chemokines.
36. The kit of paragraph 35 wherein the cytokines or chemokines comprise one or more of IL-23, IL-22, IL-17E, IL-17F IFN-γ, TNF, IFN-α, MIP-1α, MMP-1β, IL-17F, IL-1β, CXCL9, CXCL10, IL-12.
37. The kit of any one of paragraphs 35-36, wherein the assay is an enzyme-linked immunosorbent assay (ELISA).
38. The kit of any one of paragraphs 34-37, wherein the assay is a western blot.
39. The kit of any one of paragraphs 34-38, wherein said kit further comprises *E. coli* and/or *B. fragilis* whole cells or potential antigens derived from them.
40. The kit or method of any one of paragraphs 1-39 for use in identifying a patient with Rheumatoid arthritis.

41. The kit or method of paragraph 40, wherein the Rheumatoid arthritis is new onset rheumatoid arthritis or chronic rheumatoid arthritis.

42. A composition comprising an antigen from *P. copri* attached to a support matrix.

43. The composition of paragraph 42, wherein the antigen is *P. copri* Pc-p27 protein or a portion thereof.

The invention is further illustrated by the following examples, which should not be further construed as further limiting.

EXAMPLES

Example 1

An unbiased, discovery-based approach was developed to identify novel, immunogenic T cell epitopes in patients with chronic inflammatory arthritis. With this approach, in vivo HLA-DR presented peptides in patients' synovial tissue, synovial fluid mononuclear cells (SFMC), or peripheral blood mononuclear cells (PBMC) are identified by tandem mass spectrometry (LC-MS/MS) (Seward et al., 2011), followed by testing with patients' samples to determine the antigenicity of identified peptides and their source proteins. Using this method, 4 novel autoantigens in Lyme arthritis (Crowley et al., 2015; Crowley et al., 2016; Drouin et al., 2013; Pianta et al., 2015) and 2 new autoantigens in RA (Pianta A, 2015b) that are targets of T and B cell responses in many patients with these diseases were identified.

Recently, this approach was used to search for T cell epitopes of proteins derived from microbes implicated in RA. Reported herein is the identification of an HLA-DR-presented peptide (T cell epitope) derived from a *P. copri* 27-kD protein (Pc-p27), which stimulated Th1 responses in 42% of RA patients. It was also found that *P. copri* induced differential immune responses to this protein or the whole organism in a substantial portion of RA patients. Although not mutually exclusive, one type of immune response, a Th17 response, was indicative of a mucosal immunity that may help contain the organism but enhance autoimmunity. The other was indicative of a systemic Th1 immune response, accompanied by spread of *Prevotella* to joints, but with less frequent ACPA. Taken together, *P. copri* appears to be an immune-relevant bacterium in RA disease pathogenesis.

Methods

RA Patients and Control Subjects.

The study, "Autoantigens in RA," was approved by the Human Investigations Committee at Massachusetts General Hospital (MGH); all subjects gave written informed consent. All RA patients met the American College of Rheumatology/European League Against Rheumatism Collaborative Initiative criteria for that disease (Aletaha et al., 2010). All study patients with RA or other rheumatic diseases were recruited from the Rheumatology Clinic at Massachusetts General Hospital (MGH) or from suburban MGH clinics.

For isolation of HLA-DR-presented peptides, synovial tissue, SFMC or PBMC were obtained from 5 patients with RA. To test implicated peptides and their source proteins for immunoreactivity in larger numbers of patients, the cohort of NORA patients were used from whom systematic clinical information, PBMC and serum samples, and in some cases, SF were available. For comparison, PBMC and serum samples were available from patients with Lyme arthritis. In addition, serum and sometimes SF samples were collected from CRA patients, and serum samples were obtained from patients with other types of arthritis or connective tissue diseases, and from healthy control subjects. HLA-DR typing was performed on blood samples from RA patients at the American Red Cross Laboratory in Dedham, Mass. ACPA and RF determinations were made in the clinical laboratories at MGH.

Enzyme-Linked Immunospot (ELISpot) T Cell Assay.

A detailed description of the methods for isolation and identification of HLA-DR presented peptides is given in Seward et al., 2011. In initial experiments in this study, one microbial peptide ($^{2}$KRIILILTVLLAMLGQVAY$^{20}$)(SEQ ID NO: 6) derived from a 27 kDa *P. copri* protein (WP_022121928.1) was identified from the PBMC of one RA patient. This *P. copri* peptide and 2 additional peptides from the same protein, which were predicted to be promiscuous T cell epitopes ($^{52}$DYRGYWTMRYQFDSATVS$^{69}$ (SEQ ID NO: 7), $^{118}$EKINSLPTSSTGI$^{130}$ (SEQ ID NO: 8)), were synthesized and HPLC-purified in the Core Proteomics Laboratory at MGH. PBMC from RA patients were then stimulated with the peptides (1 µM) in duplicate along with positive (phytohemagglutinin) and negative (no antigen) controls, and incubated for 5 days in culture in a $CO_2$ incubator at 37° C. Cells were then transferred to Dual Color ELISpot plates coated with IFN-γ/IL17 antibodies (Cellular Technology Limited), and incubated overnight at 37° C. Images of wells were captured using ImmunoSpot series 3B analyzer, and spots were counted using ImmunoSpot software. A positive T cell response was defined as 3 standard deviations (SD) above the mean value of healthy subjects.

ELISA for Serum IgG and IgA Antibodies to the *P. Copri* Protein (Pc-p27).

ELISA plates were coated with 0.25 µg/ml of the *P. copri* protein Pc-p27 (GenScript USA Inc, Piscataway, N.J.) overnight at 4° C. Subsequent incubations and washes were performed at room temperature. After washing with phosphate buffered saline with 0.05% Tween-20 (PBST), the plates were incubated with blocking buffer (5% nonfat dry milk in PBST) for one hour. Afterwards, 100 µl of each patient's serum sample (diluted 200-fold) was added in duplicate wells for 1.5 hours, followed by horseradish-peroxidase (HRP)-conjugated goat anti-human IgG (sc-2453, Santa Cruz Biotech) or HRP-conjugated goat anti-human IgA (Bio-Rad, Hercules, Calif.) and then TMB substrate (BD, San Diego, Calif.). For inter-plate standardization, 2 control samples were included on each plate.

ELISA for Serum IgG and IgA Antibodies to Gut Microbial Organisms.

The *P. copri* type strain (DSM 18205) was obtained from the Leibniz Institute DSMZ-German Collection of Microorganisms and Cell Cultures (Braunschweig, Germany). *B. fragilis* (ATCC 25285) and *E. coli* (ATCC 25922) isolates were obtained from the American Type Culture Collection (ATCC, Manassas, Va.). The bacterial cultures were inactivated in 1% formalin for 24 hours and washed twice in PBS and diluted in PBS at a final concentration of $10^6$ cells/ml.

IgG and IgA antibody responses against whole-cell *P. copri*, *B. fragilis* or *E. coli* were determined by ELISA. All analyses were done in duplicate using 100 µl of solution per well. ELISA plates were coated overnight at 4° C. with suspensions of inactivated whole bacterial cells ($10^6$ cells/ml). After washing with PBST, the plates were incubated with blocking buffer for one hour. Afterwards, each patient's serum sample (diluted 1:100) was added in duplicate wells for 1.5 hours, followed by horseradish-peroxidase (HRP)-conjugated goat anti-human IgG (sc-2453, Santa Cruz Biotech) or HRP-conjugated goat anti-human IgA (Bio-Rad) and then TMB substrate (BD). For inter-plate standardization, 2 control samples were included on each plate.

Cytokine and Chemokine Determinations.

The levels of 14 cytokines and chemokines associated with innate immune responses (IFN-γ, TNF, MIP-1α, MIP-1β), and Th1 (IFNγ, IL-12, CXCL9, and CXCL10) or Th17 (IL-1β, IL-17A, IL-17E, IL-17F, IL-22, and IL-23) adaptive immune responses were determined in serum or SF samples from RA patients. Samples were diluted 1:5 in PBS and incubated with Heteroblock (Omega Biologicals) at a concentration of 150 μg/ml to limit the possible confounding effects of rheumatoid factor. Protein levels of all 14 inflammatory mediators in serum or SF were assessed in one complete experiment using bead-based Luminex assays (EMD-Millipore) coupled with the Luminex-200 System Analyzer (Luminex, Austin, Tex.). Data were assessed using the xPONENT 3.1 software.

Detection of *P. Copri* DNA in Patients' Samples by PCR.

DNA was isolated from 200 μl of serum or synovial fluid using the QIAamp DNA mini (QIAGEN), according to manufacturer's protocol. Nested PCR primers were designed to detect DNA for the *P. copri* ribosomal 16S RNA gene (16S rDNA) using Primer3 software. Target DNA was amplified for outer PCR using the forward primer CCAAGTAGCGTGCAGGATGA (SEQ ID NO: 9) and the reverse primer TTCAAGCCCGGGTAAGGTTC (SEQ ID NO: 10). One μl of the amplified DNA (1:10 in sterile distilled water) was used for the second PCR reaction using the forward primer CGCGGTAATACGGAAGGTCC (SEQ ID NO: 11) and the reverse primer GATACCCGCACTTTCGAGCT (SEQ ID NO: 12). Both reactions were carried out using 2.5 U of HotStarTaq DNA polymerase (QIAGEN), according to manufacturer's protocol. The amplification program included 40 cycles with denaturation 94° C. for 30 s, annealing 59° C. for 30 s, extension 72° C. for 50 s, and a final extension of 10 min. For both outer and nested PCR reactions, one positive control (*P. copri* DNA derived from the type strain, DSM 18205) and a negative control (sterile distilled water) were included. When enough DNA was available, samples were tested in duplicates. Amplified products (10 μl) were visualized by electrophoresis in a 2% agarose gel. Correct identity of PCR products were validated by direct DNA sequencing carried out in the Center for Computational & Integrative Biology DNA CORE facility at MGH. The sequenced product was aligned with all human and known microbial genomes using Genomic Blast Sequence.

Statistical Analyses.

Categorical data were analyzed by Fisher's exact test, and quantitative data were analyzed using unpaired t test with Welch correction. Correlations were sought using Pearson's correlation test. All analyses were performed using GraphPad Prism 6. All P values were two-tailed. P values <0.05 were considered statistically significant.

Results

Identification of Naturally Presented, Microbial HLA-DR-presented Peptides

Using tandem mass spectrometry (LC-MS/MS), HLA-DR-presented peptides in synovial tissue (N=4), SFMC (N=3) or PBMC (N=2) were identified from 5 patients with NORA or chronic RA (CRA). From the 17 HLA-DR-presented peptides identified from the PBMC of one patient (called here RA1), one *P. copri* sequence was found (FIG. 1A). In contrast, no sequences from *P. gingivalis* or from *B. burgdorferi*, the Lyme disease agent, were identified in any sample.

At disease onset, patient RA1, who had 2 copies of the RA "shared epitope" (HLA-DRB1*0401 and 0101), had severe symmetrical polyarthritis affecting large and small joints. During the course of the disease, patient RA1 developed a positive test for ACPA, but not RF. Despite treatment with disease modifying anti-rheumatic drugs (DMARDs), patient RA1 had recurrent episodes of knee swelling with evidence of destructive changes in cartilage and bone. The HLA-DR-presented peptide derived from *P. copri* was identified from PBMC obtained during one such episode 7 years after disease onset.

The peptide sequence of 19 amino acids had 100% sequence homology with the signal sequence of a 27-kD protein of *P. copri* (Pc-p27, WP_022121928.1) (FIG. 1A). The peptide had minimal sequence homology with any other human peptide, indicating that it was not a human protein erroneously assigned with a microbial database. Using signalP 4.0 software (Petersen et al., 2011), this HLA-DR-presented *P. copri* peptide was predicted to be part of the Sec secretion signal peptide sequence (D score=0.869), indicating that the peptide would be cleaved from the source protein. In addition, the algorithm TEPITOPE predicted that the peptide would be highly promiscuous and would bind all 25 HLA-DR molecules modeled in the program (Sturniolo et al., 1999), including the patient's DRB1*0101 and 0401 molecules. When patient RA1 PBMC were stimulated with various concentrations of this *P. copri* peptide in an IFN-γ ELISpot assay, patient RA1 T cells secreted levels of IFN-γ that were >3 times background (FIG. 1A insert), attesting to the peptide's immunogenicity.

T Cell Reactivity to *P. copri* Peptides in NORA Patients

Figures 1B, 1C, 1D, 1E:
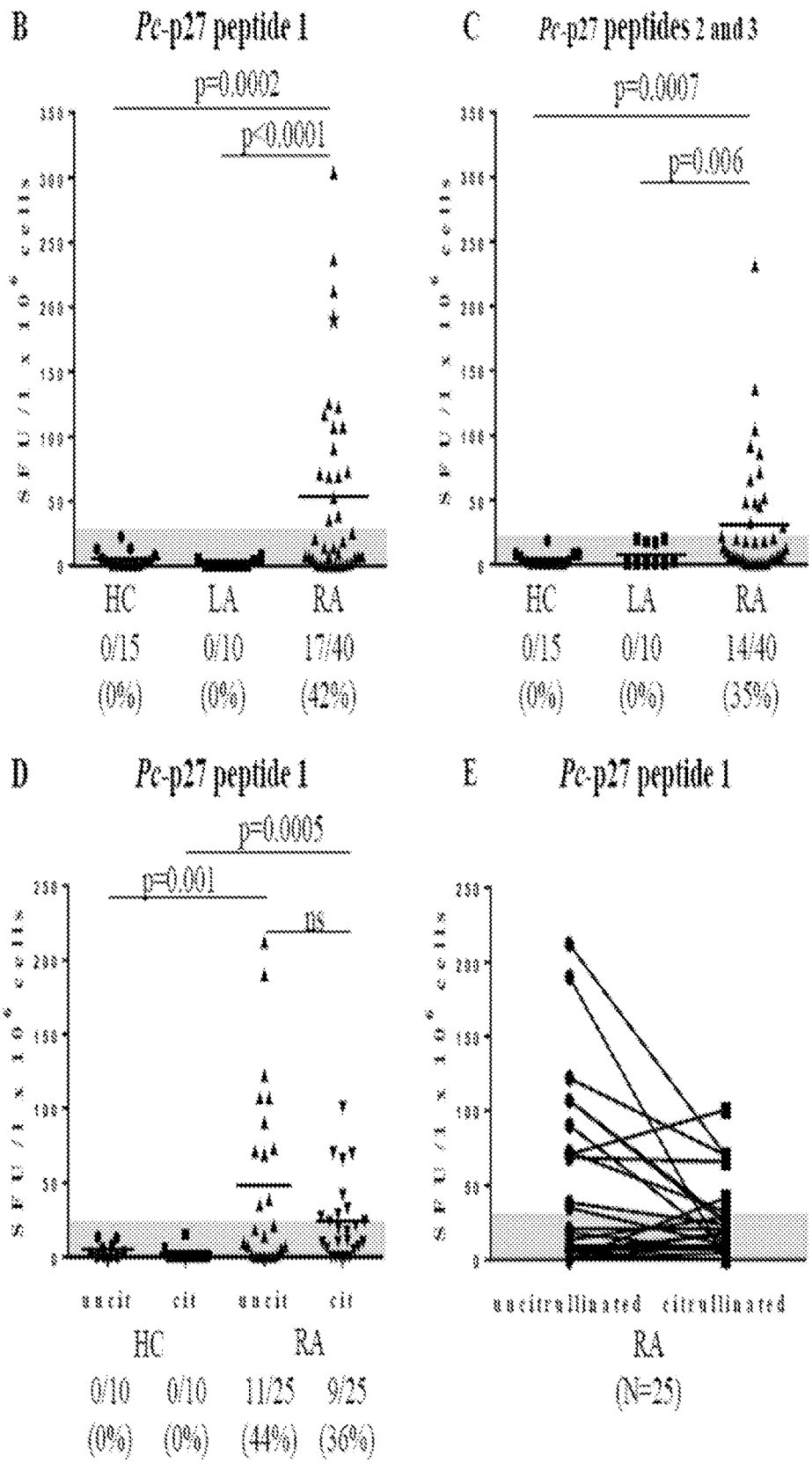

To determine the immunogenicity of HLA-DR-presented peptides of Pc-p27 more broadly, PBMC obtained from the cohort of patients with new-onset RA (NORA) seen prior to DMARD therapy was used, the time when immune responses would be expected to be most robust. When PBMC from 39 NORA patients and from the case patient RA1 (a CRA patient) were stimulated with the signal peptide sequence from Pc-p27 peptide 1, 17 of the 40 patients (42%) secreted levels of IFN-γ that were >3 SD above the mean value of HC (P=0.0002), using an IFN-γ/IL-17 Double-Color ELISpot assay (FIG. 1B). In comparison, patients with Lyme arthritis (LA) lacked reactivity with this peptide (P<0.0001). The predominant response to stimulation with Pc-p27 in the RA patients was a Th1-type response with IFN-γ secretion, whereas PBMC from only one RA patient secreted small amounts of IL-17 (data not shown).

To determine whether patients had reactivity with other epitopes of the Pc-p27 protein, TEPITOPE was used to predict 2 additional promiscuous peptides derived from the same protein (Pc-p27 peptides 2 and 3). The 2 peptides together were predicted to be presented by all 25 HLA-DR molecules in the program, and therefore, these peptides were pooled for testing. PBMC from 14 of the 40 patients (35%) secreted levels of IFN-γ to peptides 2 and 3 that were >3 SD above the mean value of HC (P=0.0007) or patients with LA (P=0.006) (FIG. 1C). Altogether, PBMC from 24 of the 40 patients (60%) had reactivity with 1 or more of the 3 *P. copri* peptide sequences, showing that Th1 immune responses to this protein were common in NORA patients.

Because of the importance of citrullinated proteins in RA pathogenesis (Brink et al., 2013; McInnes and Schett, 2011), peptide 1 was re-synthesized with a citrulline in place of the only arginine in the peptide, which was predicted to be in the—P1 position in the flanking region of the HLA-DR binding pocket. The citrullinated peptide induced an IFN-γ response in 36% of patients compared with 44% who had reactivity with the uncitrullinated peptide (FIG. 1D). In most patients, the response to the citrullinated peptide was lower than that to the uncitrullinated peptide. Moreover, no patient who lacked reactivity with the unmodified peptide had a response to the citrullinated peptide (FIG. 1E). Thus, the Pc-p27 signal peptide sequence is not citrullinated in vivo.

IgG and IgA Antibody Responses to Pc-p27 and Whole *P. copri*

Since the role of *P. copri*-specific CD4+ T cells is to help B cells produce antibodies to the organism, the antibody responses to Pc-p27 in serum samples from 303 individuals was determined. These included samples from 127 patients with new-onset or chronic RA, 28 patients with connective tissue diseases (14 with systemic lupus, 4 with mixed connective tissue disease, 4 with scleroderma, and 6 with Sjogren's syndrome), 28 patients with spondyloarthropathy (15 with psoriatic arthritis, 10 with ankylosing spondylitis, and 3 with reactive arthritis), 70 patients with Lyme arthritis, and 50 healthy control subjects.

Figures 2A, 2B, 2C, 2D:
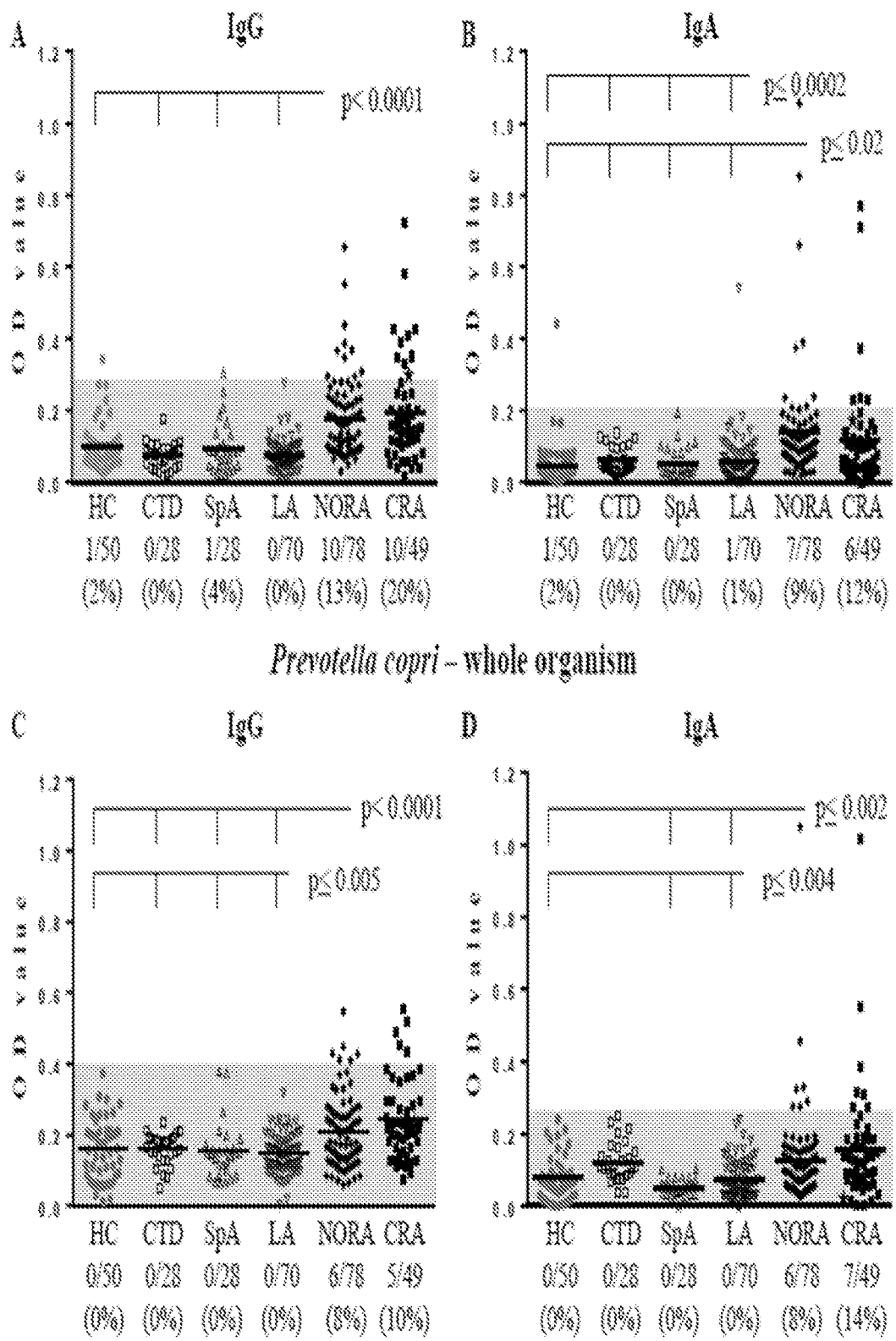
FIGS. 2A-2D show IgG and IgA responses to *P. copri* in RA patients and control subjects. Serum samples from 303 individuals with NORA, CRA, other forms of chronic inflammatory arthritis, connective tissue diseases, or healthy controls were tested for *P. copri* antibodies. ELISA of IgG (FIG. 2A) and IgA (FIG. 2B) against the bacterial protein Pc-p27; ELISA of IgG (FIG. 2C) and IgA (FIG. 2D) against 1% formalin-inactivated *P. copri*. For all analyses, positivity was defined as >3 SD above the mean value of healthy controls (area above the shaded region). Symbols represent values in individual patients and horizontal lines show mean values. The value for patient RA1 is indicated with a star. Only significant P values are shown. HC, healthy control; CTD, connective tissue diseases; SpA, spondyloarthropathies; LA, Lyme arthritis; NORA, new onset rheumatoid arthritis; CRA, chronic rheumatoid arthritis.

Of the 78 NORA patients, 10 (13%) had IgG antibody responses to Pc-p27 that were >3 SD above those in HC (P<0.0001) (FIG. 2A). Moreover, 10 of 49 patients (20%) with chronic RA (CRA) had positive IgG antibody responses to the protein (P<0.0001), including patient RA1 in whom 4 serial samples obtained 4 to 9 years after disease onset yielded positive results. In contrast, of the 126 patients with other diseases and 50 healthy control subjects, only one with a spondyloarthropathy (SpA) and one healthy subject had borderline positive IgG antibody responses to the protein.

Because the first interactions between *P. copri* and immune cells would presumably occur in the gut mucosa, the IgA antibody responses to the organism was also determined. About 10% of the patients in both the NORA and CRA groups had IgA antibody responses to Pc-p27 (P<0.0002 and P<0.02, respectively), and the responses was more robust in NORA patients (FIG. 2B). In contrast, only 1 patient with LA and 1 healthy subject had IgA antibody reactivity with the protein. Except for 2 RA patients who had both IgG and IgA responses to Pc-p27, the other Pc-p27-positive patients had either an IgG or IgA response, but not both. Altogether, 24% of the 127 RA patients had IgG or IgA antibody responses to Pc-p27.

When both T and B cell responses were considered together, 3 of the 24 patients who had T cell reactivity with Pc-p27 peptides also had IgG Pc-p27 antibody responses, but none had IgA responses to the protein. In comparison, among 16 patients lacking T cell reactivity with Pc-p27 peptides, only 1 had an IgG antibody response to the protein, but 5 had IgA responses (P=0.05). The frequencies of "shared epitope" alleles in patients with *P. copri* T or B cell responses was not significantly different than those in patients who lacked these responses.

To confirm and extend these findings, the frequency of IgG and IgA antibody responses to whole *P. copri* was determined using the same set of 303 serum samples. Six of the 78 NORA patients (8%) and 5 of the 49 CRA patients (10%) had IgG antibody responses to *P. copri* that were >3 SD above the mean values in healthy controls (HC) (P<0.005 and P<0.0001, respectively) (FIG. 2C). Similarly, 6 of 78 NORA patients (8%) had IgA antibody responses to *P. copri* (P<0.004), and 7 of 49 patients (14%) with CRA had elevated IgA antibody levels to the organism (P<0.002) (FIG. 2D). Among the 19 patients who had positive IgG or IgA responses to *P. copri*, only 4 (21%) had both responses. No patient with CTD, SpA, or LA had IgG or IgA antibody reactivity with the organism. Altogether, 15% of 127 RA patients had IgG or IgA antibody responses to whole *P. copri*.

When the antibody responses to whole *P. copri* or recombinant Pc-p27 were combined, 41 (32%) of the 127 RA patients had IgG or IgA antibody reactivity with the organism. With both preparations, antibody responses to *P. copri* were common in RA patients, both early and late in the disease, yet they were rarely found in patients with other types of arthritis, implying specificity in RA.

Testing for Antibody Responses to other Commensal Bowel Flora

For comparison, antibody responses were determined to two other gut commensal organisms, using whole cell preparations of *Bacteroides fragilis* and *Escherichia coli*. In contrast to the findings with *P. copri*, very few RA patients or those with other types of chronic inflammatory arthritis or connective tissue diseases had IgG or IgA antibody responses to *B. fragilis* or *E. coli* that were >3 SD above the mean values in healthy control subjects (FIG. 3A-3D). However, IgG absorbance values for *B. fragilis* were significantly lower in NORA patients than in patients in the other groups (P<0.03) (FIG. 3A), consistent with the decrease in *B. fragilis* abundance noted previously in NORA patients (Scher et al., 2013). Conversely, IgG and IgA absorbance values to *B. fragilis* in the CTD group were significantly higher than those in the other groups. Thus, in contrast with *P. copri* antibody responses, antibody levels to *B. fragilis* and *E. coli* were similar or less in RA patients compared with those in patients with other types of arthritis or in healthy control subjects.

Correlation of *P. copri* Antibodies with Serum Cytokine Levels and RA Autoantibodies To link *P. copri* with inflammatory responses and autoantibody production, IgG and IgA *P. copri* antibody values were correlated with serum cytokine levels and RA autoantibody frequencies (ACPA and RF) in 120 of the 127 RA patients in whom sufficient serum samples were still available. For this analysis, the values in the 37 NORA and CRA patients who had positive *P. copri* antibody responses were compared with either Pc-p27 or the whole organism with those in the 83 patients who lacked these antibody responses. The 14 cytokines and chemokines measured were representative of innate, Th1 and Th17 immune responses. These assays were performed with Heteroblock to limit the possible interference by rheumatoid factor.

Figures 4A, 4B, 4C:
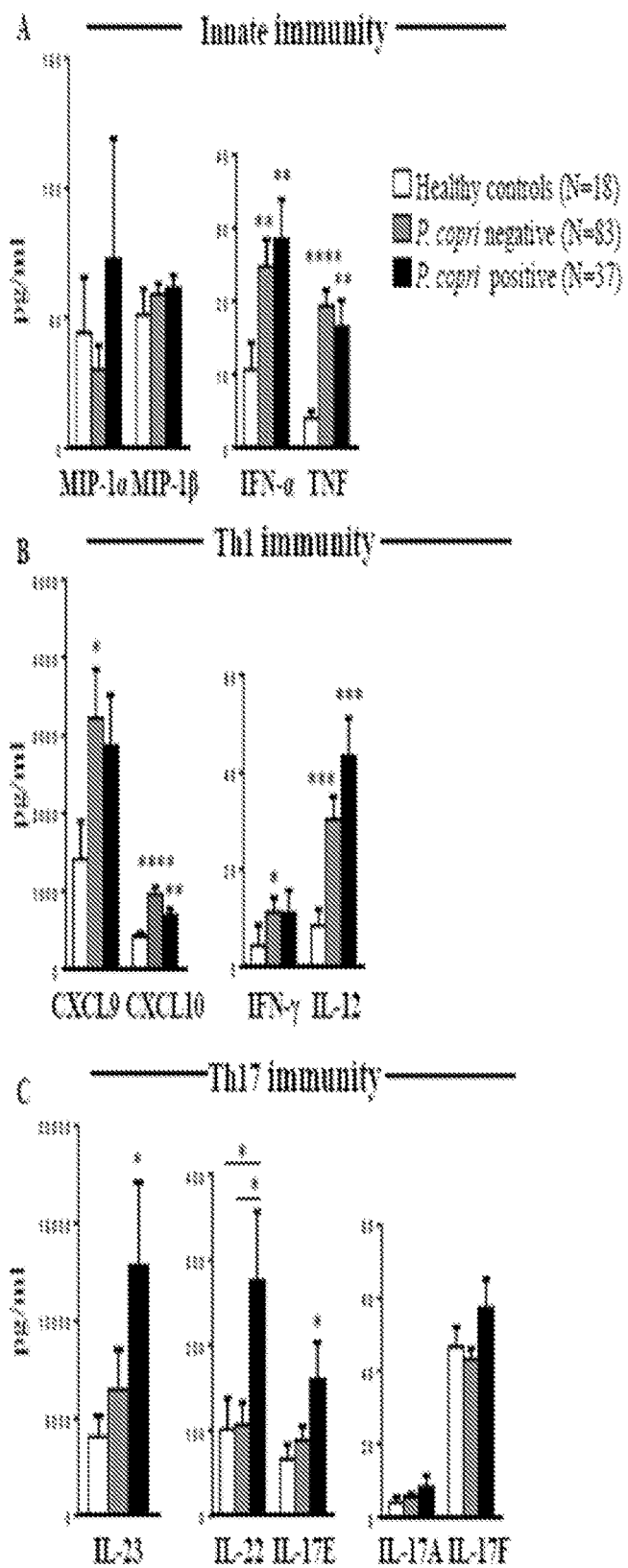
FIGS. 4A-4C show serum cytokine and chemokine levels according to *P. copri* antibody responses. The levels of 14 cytokines and chemokines were determined by Luminex in serum samples from 18 healthy controls, 83 RA patients who had negative *P. copri* antibody responses, and 37 RA patients who had positive *P. copri* antibody responses. Cytokines associated with innate immunity (FIG. 4A), Th1 immunity (FIG. 4B), and Th17 immunity (FIG. 4C) are shown. Data are presented as mean±SEM. P values show significance vs. healthy control levels, except for IL-22 where significance was reached also between the *P. copri* positive and *P. copri* negative patients. *P≤0.05, P<0.01, *P<0.001, ****P<0.0001 Student's t-test.

When the levels of these mediators were compared in patients and healthy controls, two cytokines associated with innate immunity (IFN-α and TNF) and four cytokines and chemokines associated with Th1 immunity (CXCL9, CXCL10, IFN-γ, and IL-12) were significantly higher both in *P. copri*-positive and *P. copri*-negative RA patients compared with healthy controls. However, no significant differences were observed between patients who did or did not have *P. copri* antibodies (FIG. 4A-B). In contrast, the levels of three cytokines associated with Th17 immunity (IL-23, IL-22, and IL-17E) were significantly higher only in RA patients who had *P. copri* antibodies compared with healthy controls (FIG. 4C), and the levels of these cytokines in *P. copri*-negative patients were similar to those in healthy controls. The differences between *P. copri*-positive and *P. copri*-negative patients reached statistical significance for IL-22 (P=0.05).

Figures 5A, 5B:
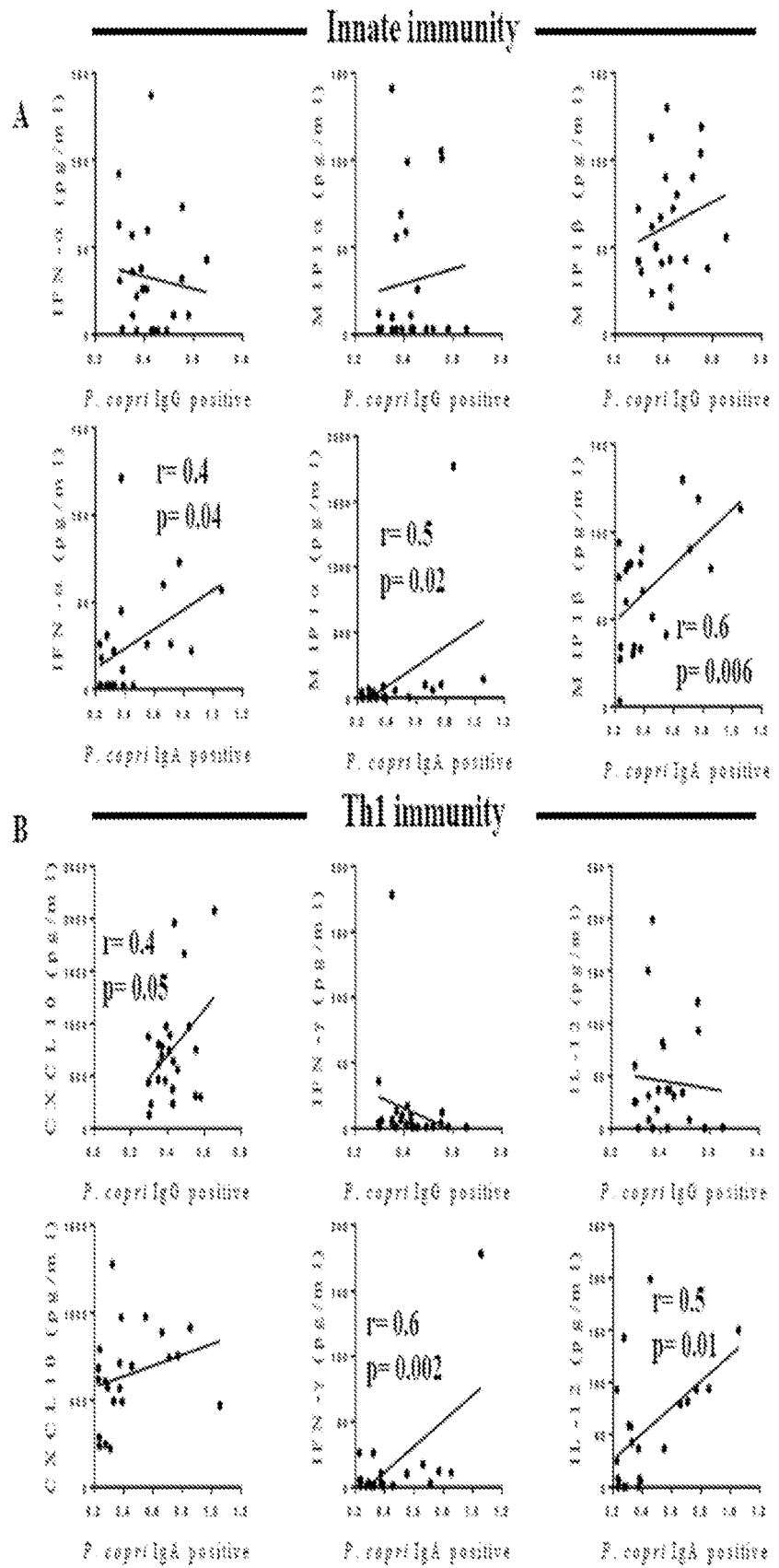
FIGS. 5A-5C show correlation between cytokine levels and *P. copri* antibody responses. Correlation between *P. copri* specific IgG or IgA responses and cytokines associated with innate immunity (FIG. 5A), Th1 immunity (FIG. 5B) and Th17 immunity (FIG. 5C). Correlations were performed using the Pearson's correlation test.
Figure 5C:
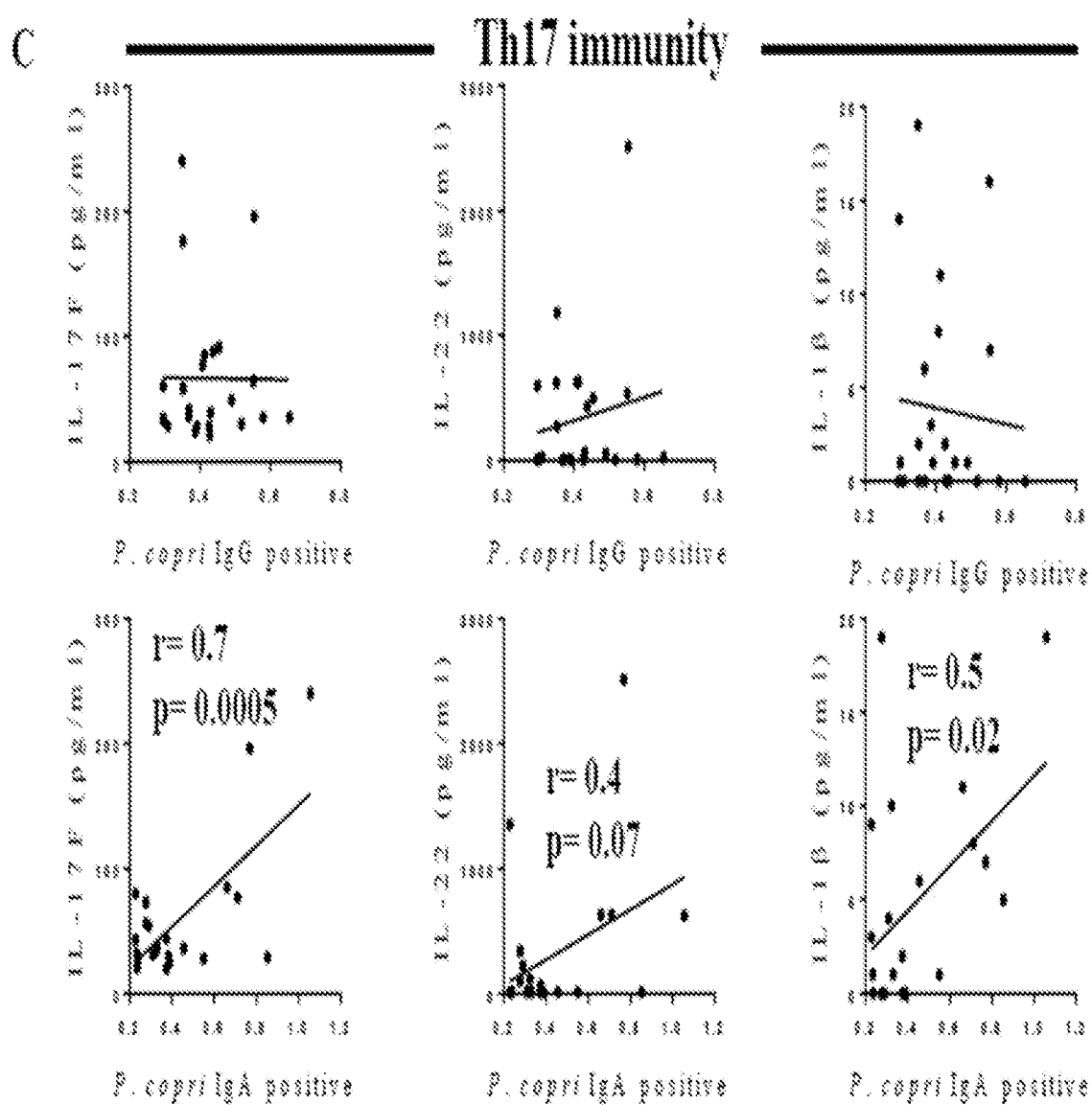

When the magnitude of *P. copri* IgG or IgA antibody responses were correlated with cytokine levels, there were strong, positive correlations between IgA antibody values and the levels of three innate cytokines (IFN-γ, MIP-1α, and MMP-1β), but no correlations were found with *P. copri* IgG antibody responses (FIG. 5A). In addition, IgA *P. copri* antibody levels correlated directly with the levels of two Th1-associated cytokines (IFN-γ and IL-12) and with three Th17 cytokines (IL-17F, IL-22, and IL-1β) (FIG. 5C). In contrast, IgG *P. copri* antibody values correlated only with levels of the Th1 chemoattractant CXCL10 (FIG. 5B). Absorbance values in *P. copri*-negative patients did not correlate with any innate, Th1 or Th17 cytokine level (data not shown).

Among 14 patients in whom SF samples were available, the innate inflammatory mediators (IFN-γ, TNF, MIP-1α, MIP-1β) and pro-inflammatory Th1 mediators (IFN-γ, IL-12, CXCL9 and CXCL10) were concentrated in SF, whereas the levels of several Th17-associated cytokines (IL-23, IL-22, IL-17E and IL-17F) were significantly greater in serum (FIG. 5C). Thus, innate and Th1 inflammatory responses were concentrated in affected joints, whereas serum Th17 cytokine responses were presumably a reflection of immune responses at mucosal sites. However, this group of 14 patients was not large enough for meaningful subgroup analysis according to IgG or IgA *P. copri* antibody responses.

Figures 6A, 6B:
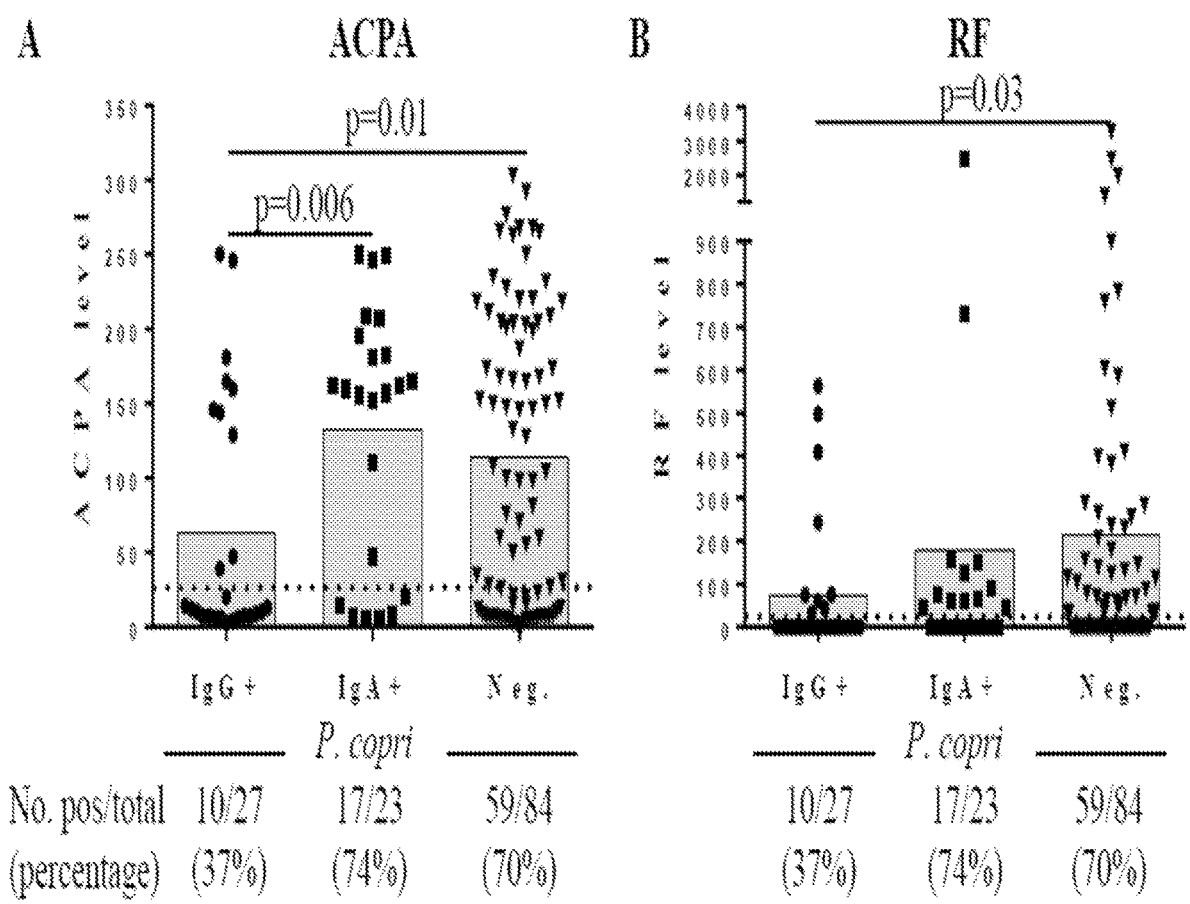
FIGS. 6A-6B show standard RA autoantibodies according to *P. copri* antibody responses. In patients with RA, the levels of anti-citrullinated protein antibodies (ACPA) (FIG. 6A) and rheumatoid factor (RF) (FIG. 6B) are stratified according to IgG or IgA antibody responses to *P. copri*. ACPA values >20 and RF values >30 (above the scattered line) were defined as positive. Symbols represent values in individual patients and gray bars show mean values. Only significant P values are shown.

When *P. copri* IgG or IgA antibody responses were stratified according to RA autoantibodies, only 37% of the patients with IgG *P. copri* antibody responses had ACPA compared with 74% with IgA *P. copri* antibodies (P=0.006) and 70% with no *P. copri* antibodies (P=0.01) (FIG. 6A). There was a similar trend for RF (FIG. 6B). Thus, ACPA, and to a lesser degree RF, was significantly less common in patients with IgG *P. copri* antibodies than in patients in the other two groups. Taken together, the strong association of IgA immune responses to *P. copri* with key pro-inflammatory cytokines and high frequencies of ACPA indicate that this antibody response is linked to systemic inflammation and autoimmunity in this subgroup of RA patients, whereas the IgG response to *P. copri* may be a component of a Th1 response primarily localized in joints and less often associated with classic RA autoantibodies.

Detection of *P. copri* 16S rDNA in Synovial Fluid

Because *P. copri* IgG antibody responses were indicative of a systemic immune response to the organism and because Th1 cytokines were concentrated in SF, the question of whether *P. copri* itself may spread to joints was addressed. For this purpose, nested PCR primers were designed in an effort to detect DNA for the 16S ribosomal RNA gene of *P. copri* (16S rDNA) in patients' samples. Of 18 patients in whom paired serum and SF samples were available, 10 were obtained from NORA patients who were seen prior to DMARD therapy, and 8 were collected from CRA patients who were seen from 3-to-50 years after disease onset. Five of the 18 patients had IgG antibody responses to *P. copri*; 2 had IgA antibody reactivity with the organism, and 11 did not have *P. copri* antibody responses.

Figures 7A, 7B:
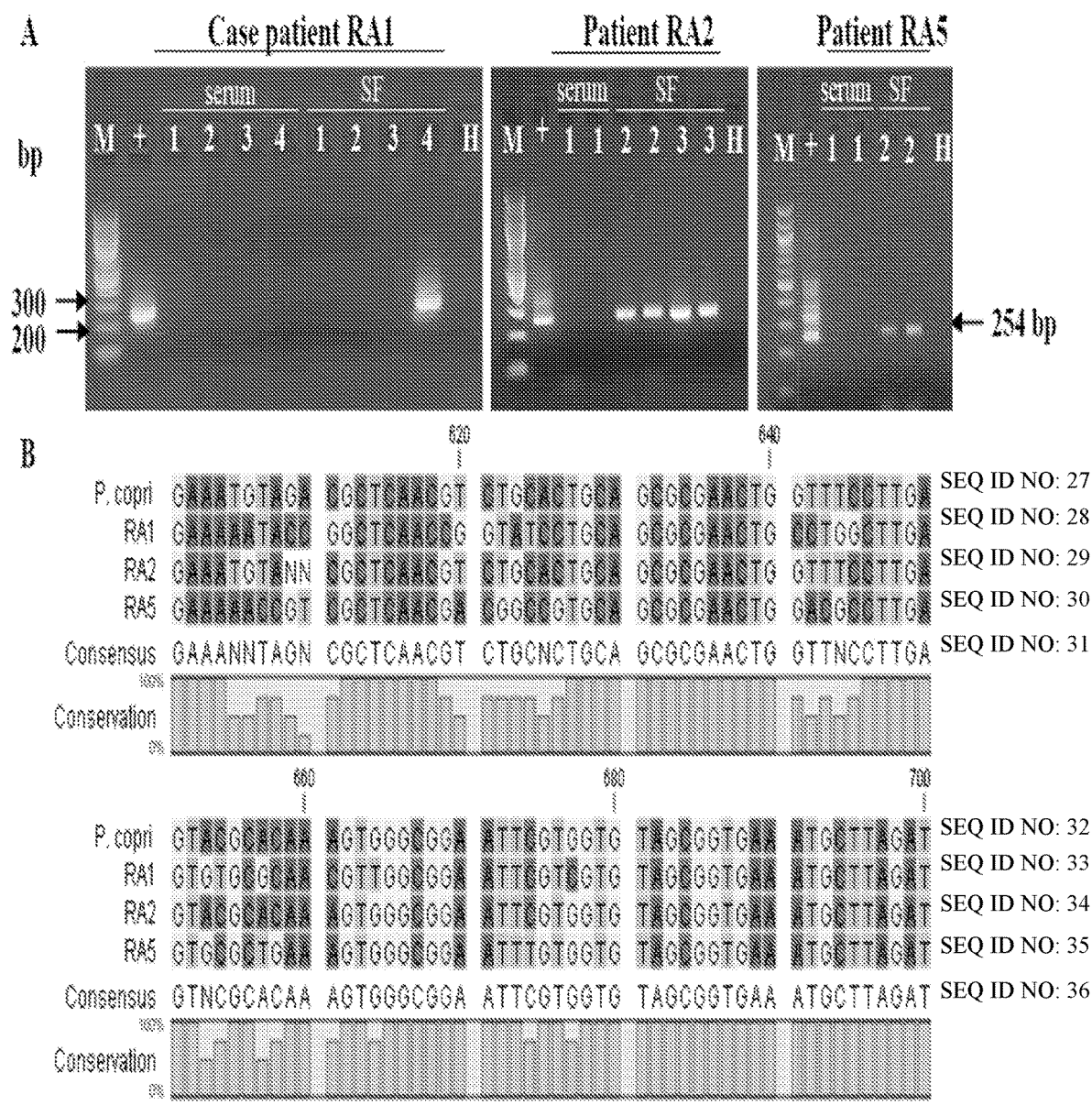
FIGS. 7A-7B show PCR testing for *Prevotella copri* 16S rDNA in concomitant serum and SF samples of RA patients.
Figure 8A:
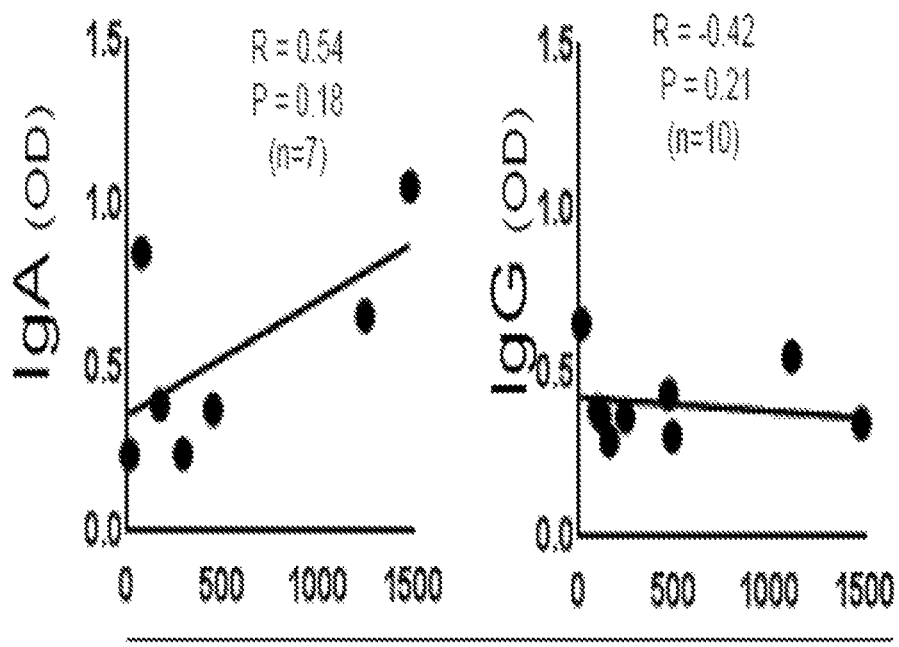
FIGS. 8A-8B show correlation between IL-23 levels and Pc-p27 IgA and IgG antibody responses. IL 23 levels were determined by Luminex and correlated to the levels of IgG and IgA antibodies in RA patients. IgA antibody responses to Pc-p27 correlated with higher serum IL-23 levels (indicative of Th17 responses) whereas IgG antibody responses to the protein correlated with lower IL-23 levels.
Figure 8B:
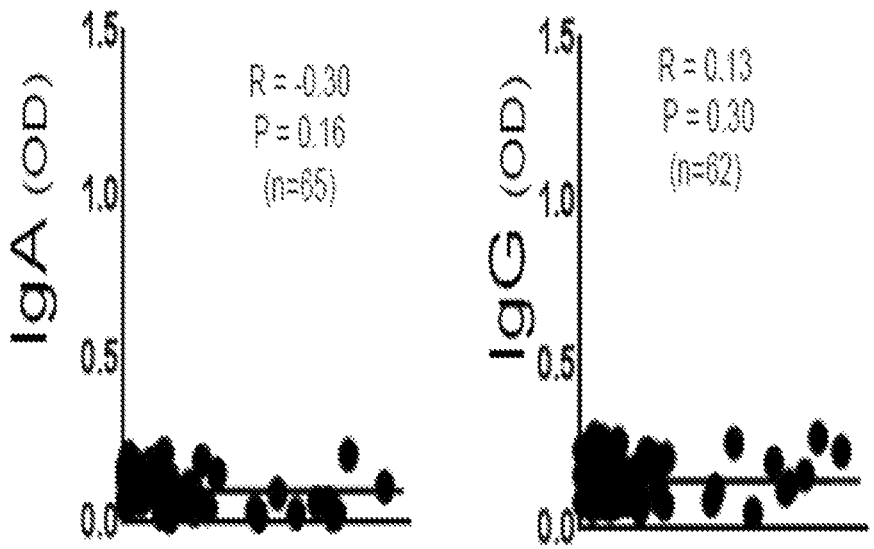
Figure 9:
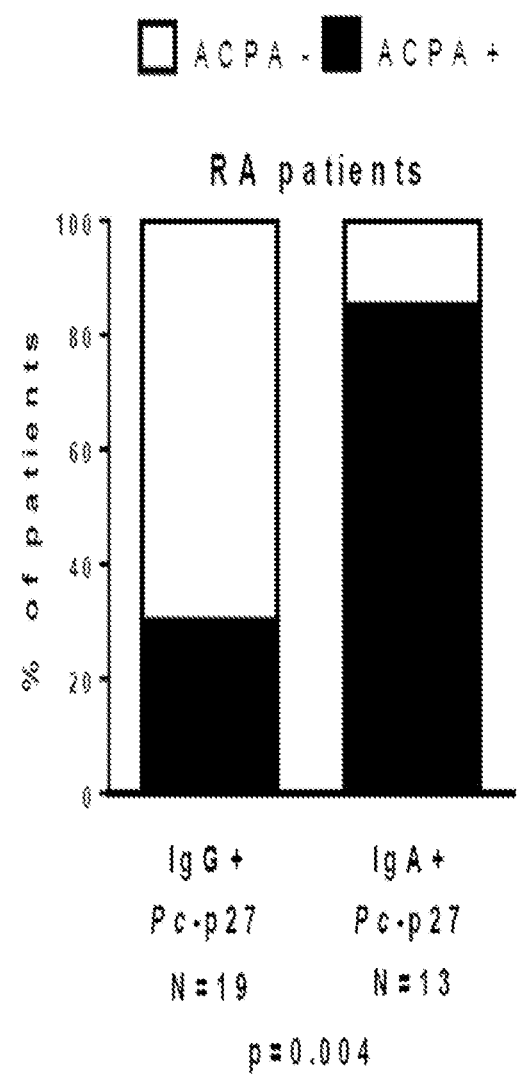
FIG. 9 shows positivity ACPA positivity in anti-Pc-p27 IgG (left) or IgA (right) seropositive patients. IgA antibody responses to Pc-p27 correlated with more frequent ACPA, whereas IgG antibody responses to the protein correlated with less frequent ACPA.

Of the 5 patients (RA1 to RA5) with IgG *P. copri* antibodies, 3 had *P. copri* 16S rDNA detected in SF. Of 2 samples from NORA patient RA2, 16S rDNA was found in one SF sample obtained prior to DMARD therapy and in one collected 2 months after the start of therapy (FIG. 7A). In NORA patient RA5, *P. copri* 16S amplicons were detected in the only SF sample, which was obtained prior to DMARD therapy, one year after disease onset (FIG. 7A). In these 2 patients, enough sample was available to perform the test in duplicate, and positive results were obtained from duplicate samples. In CRA patient RA1, in whom the original HLA-DR-presented *P. copri* peptide was identified in PBMC collected 7 years after disease onset (FIG. 1A), *P. copri* 16S rDNA was detected in SF obtained 9 years after disease onset (FIG. 7A). NORA patient RA3 and CRA patient RA4 also had IgG *P. copri* antibodies, but *P. copri* DNA was not detected in their single SF samples (data not shown). Similarly, *P. copri* DNA was not detected in SF samples from the remaining 13 patients, 2 with IgA *P. copri* antibodies and 11 without *P. copri* antibodies. Serum samples from all 18 patients had negative PCR results. Thus, 3 of the 5 patients with IgG *P. copri* antibodies had positive PCR results for *Prevotella* DNA in SF compared with none of 13 patients in the other 2 groups (P=0.01).

All positive results were confirmed by sequencing. Amplicons from patient RA2 had 100% sequence identity with the sequence for *P. copri* 16S rDNA in the NCBI database, which was obtained from a Japanese isolate. Interestingly, patient RA2 grew up in Korea. Amplicons from patient RA1 and from patient RA5 annealed with *P. copri* sequences (DSM18205), but they had 86% and 89% sequence homology, respectively (FIG. 7B), indicating that the sequence could be from another *Prevotella* species (FIG. 7B). Alternately, the differences in *P. copri* 16S rDNA sequences may be explained by strain variation since the 3 patients grew up in widely different geographic locations (Korea, the United States, or the Caribbean Islands).

Discussion

In this study, using a discovery-based search for HLA-DR-presented peptides derived from *P. copri*, one spectrum-to-peptide match was identified from 1 of the 2 RA patients in whom sufficient PBMC were available for this type of high-throughput analysis. This peptide sequence was found in the signal domain of a 27-kD protein of *P. copri*, which was predicted to be a secreted protein. Signal sequences, which are cleaved prior to secretion, can accumulate in transmembrane locations; they are often highly antigenic, and they typically bind many different HLA-DR molecules (Kovjazin et al., 2011). In addition, the secreted portion of the protein may become an immunogenic soluble antigen (Han and Wang, 2013; Yang et al., 2014). It was then found that the signal sequence peptide and two other peptides from the Pc-p27 protein induced Th1 responses in 60% of patients with RA. Although RA SE alleles correlated inversely with *P. copri* overexpansion in the gut (Scher et al., 2013), the findings showed no significant correlations between these T cell epitopes and SE alleles, consistent with the fact that these epitopes are promiscuous HLA-DR binders.

In addition to T cell reactivity, IgA or IgG antibody responses to *P. copri* were found, but usually not both, in 32% of NORA patients. Although over-expansion of *P. copri* in stool samples was previously detected only in NORA patients (Scher et al., 2013), IgG or IgA antibody responses to the organism were found as commonly in CRA patients as in NORA patients, indicating that once initiated, these antibody responses may persist for years. In contrast, immune reactivity with *P. copri* was rarely detected in patients with other chronic inflammatory arthritides, including those with Lyme arthritis, spondylarthropathies or other connective tissue diseases, implying specificity in RA.

It was recently reported in mice that gut symbiotic gram-negative bacteria may disseminate systemically to other sites and induce IgG antibody responses (Zeng et al., 2016). These homeostatic IgG responses may help later in protection against invasion by pathogenic gram-negative bacteria. High background in *E. coli* and *B. fragilis* antibody assays were found, perhaps reflecting positive responses to these bacteria in some individuals. However, the distribution of antibody values to these bacteria was not greater in RA patients than in other comparison groups, whereas *P. copri* antibody responses were significantly higher in RA patients and correlated with inflammatory cytokine levels. For this reason, these findings could not be explained simply by homeostatic *P. copri* antibody responses.

The magnitude of IgA *P. copri* antibody responses in RA patients were found to correlate with serum levels of a range of cytokines and chemokines associated with innate, Th1 and Th17 immune responses, such that the higher the IgA antibody response, the greater the cytokine level. Although Pc-27-specific Th17 cells in PBMC in this subgroup of patients was not found, it is likely that such cells were present in their intestinal mucosa, as shown by the strong correlation of IgA antibody responses with a range of Th17-associated cytokines. Th17 responses are important in containing the organism in the bowel, but they can also promote systemic inflammation and autoimmunity (Ruff and Kriegel, 2015). This idea is indicated here by strong correlations between IgA antibody values and serum levels of innate, Th1, and Th17-associated cytokines along with high frequencies of ACPA, which could react with citrullinated proteins in joints (Romero et al., 2013).

Conversely, the other RA subgroup had IgG *P. copri* antibody responses, sometimes with *Prevotella* DNA in joints, which was associated with inflammatory Th1 responses and infrequent ACPA. Although a mucosal IgA response might occur prior to systemic spread of the organism, most of the patients had only IgA or IgG antibody responses, but usually not both. In IgG-positive patients, it was postulated that *P. copri*, a strict anaerobe, may spread to joints within phagocytic cells. In 2 of 3 patients, *Prevotella* DNA was detected in SF obtained early in the disease. However, in the remaining patient (RA1), in whom the Pc-p27 HLA-DR-presented peptide was identified in PBMC obtained 7 years after disease onset, *P. copri* DNA was detected in SF collected 9 years after onset. This indicates that *P. copri* may sometimes spread from the bowel in repeated waves over a period of years, perhaps explaining the persistence of antibody responses to *P. copri* in CRA patients. In addition to *P. copri*, it is possible that other *Prevotella* species or other yet-to-be-identified commensal gut microbes may have an immune-relevant function in RA.

There are parallels between the potential role *P. copri* in RA pathogenesis and that of the periodontal pathogen, *Porphyromonas gingivalis* (Mikuls et al., 2014; Pischon et al., 2008). In patients with periodontitis, the composition of the oral flora shifts in favor of organisms, particularly anaerobes such as *P. gingivalis*, which thrive in an inflammatory environment (Hajishengallis, 2015). IgG antibody responses to *P. gingivalis* in RA patients correlate strongly with systemic inflammation and co-existent periodontal disease (Arvikar et al., 2013; Mikuls et al., 2014; Scher and Abramson, 2013). In addition, *P. gingivalis* has a PPAD enzyme, which catalyzes the post-translational conversion of arginine to peptidylcitrulline (Konig et al., 2015; Rosenstein et al., 2004; Wegner et al., 2010), and this may lead to the generation of neoepitopes and ACPA (Wegner et al., 2010). Furthermore, *P. gingivalis* may disseminate from the gingiva, presumably via dendritic cells, also leading to infection or inflammation at distant sites (Carrion et al., 2012; Han and Wang, 2013), and DNA from periodontal bacteria has been detected by PCR in SF of a few RA patients with periodontal disease (Martinez-Martinez et al., 2009).

Provided herein is evidence that *P. copri* is an immune-relevant bacterium in a subgroup of RA patients. Th17 and IgA immune responses may help contain the organism in the bowel, but may enhance systemic inflammation and autoimmunity, whereas *P. copri* IgG antibodies, sometimes with *Prevotella* DNA in joints, were associated with *P. copri*-specific Th1 responses and infrequent ACPA. These new insights are likely to have implications for both the diagnosis and treatment of RA. For example, *P. copri* IgG antibody responses could provide support for the diagnosis in RA patients who lack ACPA or RF. Regarding therapy, approaches that target *P. copri*, such as specifically tailored antibiotic regimens or diet alterations or probiotic therapies, could have an adjunctive role to DMARDs in treatment of the disease. Previously, patients with early RA who received tetracycline or its derivatives had significantly better outcomes than placebo-treated patients (O'Dell et al., 1997; Stone et al., 2003). These results are often attributed to the anti-inflammatory effects of tetracyclines, but recent insights about the microbiota indicate an additional explanation. Importantly, insights about specific immune-relevant commensal organisms in the microbiota promise a new era in the understanding and treatment of RA.

REFERENCES FOR BACKGROUND AND EXAMPLE 1

Aletaha, D., Neogi, T., Silman, A. J., Funovits, J., Felson, D. T., Bingham, C. O., 3rd, Birnbaum, N. S., Burmester, G. R., Bykerk, V. P., Cohen, M. D., et al. (2010). 2010 Rheumatoid arthritis classification criteria: an American College of Rheumatology/European League Against Rheumatism collaborative initiative. Arthritis Rheum. 62, 2569-2581.

Arvikar, S. L., Collier, D. S., Fisher, M. C., Unizony, S., Cohen, G. L., McHugh, G., Kawai, T., Strle, K., and Steere, A. C. (2013). Clinical correlations with *Porphyromonas gingivalis* antibody responses in patients with early rheumatoid arthritis. Arthritis Res. Ther. 15, R109.

Atarashi, K., Tanoue, T., Shima, T., Imaoka, A., Kuwahara, T., Momose, Y., Cheng, G., Yamasaki, S., Saito, T., Ohba, Y., et al. (2011). Induction of colonic regulatory T cells by indigenous *Clostridium* species. Science 331, 337-341.

Brink, M., Hansson, M., Mathsson, L., Jakobsson, P. J., Holmdahl, R., Hallmans, G., Stenlund, H., Ronnelid, J., Klareskog, L., and Rantapaa-Dahlqvist, S. (2013). Multiplex analyses of antibodies against citrullinated peptides in individuals prior to development of rheumatoid arthritis. Arthritis Rheum. 65, 899-910.

Carrion, J., Scisci, E., Miles, B., Sabino, G. J., Zeituni, A. E., Gu, Y., Bear, A., Genco, C. A., Brown, D. L., and Cutler, C. W. (2012). Microbial carriage state of peripheral blood dendritic cells (DCs) in chronic periodontitis influences DC differentiation, atherogenic potential. J. Immunol. 189, 3178-3187.

Catrina, A. I., Deane, K. D., and Scher, J. U. (2014). Gene, environment, microbiome and mucosal immune tolerance in rheumatoid arthritis. Rheumatology (Oxford) 55, 391-402.

Crowley, J. T., Drouin, E. E., Pianta, A., Strle, K., Wang, Q., Costello, C. E., and Steere, A. C. (2015). A highly expressed human protein, apolipoprotein B-100, serves as an autoantigen in a subgroup of patients with Lyme disease. J. Infect. Dis. 212, 1841-50.

Crowley, J. T., Strle, K., Drouin, E. E., Pianta, A., Arvikar, S. L., Wang, Q., Costello, C. E., and Steere, A. C. (2016). Matrix metalloproteinase-10 is a target of T and B cell responses that correlate with synovial pathology in patients with antibiotic-refractory Lyme arthritis. J. Autoimmun. (in press).

Drouin, E. E., Seward, R. J., Strle, K., McHugh, G., Katchar, K., Londono, D., Yao, C., Costello, C. E., and Steere, A. C. (2013). A novel human autoantigen, endothelial cell growth factor, is a target of T and B cell responses in patients with Lyme disease. Arthritis Rheum. 65, 186-196.

Firestein, G. S. (2003). Evolving concepts of rheumatoid arthritis. Nature 423, 356-361.

Hajishengallis, G. (2015). Periodontitis: from microbial immune subversion to systemic inflammation. Nature Rev. Immunol. 15, 30-44.

Han, Y. W., and Wang, X. (2013). Mobile microbiome: oral bacteria in extra-oral infections and inflammation. J. Dent. Res. 92, 485-491.

Hooper, L. V., Littman, D. R., and Macpherson, A. J. (2012). Interactions between the microbiota and the immune system. Science 336, 1268-1273.

Ivanov, I I, Atarashi, K., Manel, N., Brodie, E. L., Shima, T., Karaoz, U., Wei, D., Goldfarb, K. C., Santee, C. A., Lynch, S. V., et al. (2009). Induction of intestinal Th17 cells by segmented filamentous bacteria. Cell 139, 485-498.

Ivanov, I I, and Honda, K. (2012). Intestinal commensal microbes as immune modulators. Cell Host Microbe 12, 496-508.

Konig, M. F., Paracha, A. S., Moni, M., Bingham, C. O., 3rd, and Andrade, F. (2015). Defining the role of *Porphyromonas gingivalis* peptidylarginine deiminase (PPAD) in rheumatoid arthritis through the study of PPAD biology. Ann. Rheum. Dis. 74, 2054-2061.

Kovjazin, R., Volovitz, I., Daon, Y., Vider-Shalit, T., Azran, R., Tsaban, L., Carmon, L., and Louzoun, Y. (2011). Signal peptides and trans-membrane regions are broadly immunogenic and have high CD8+ T cell epitope densities: Implications for vaccine development. Mol. Immunol. 48, 1009-1018.

Longman, R. S., and Littman, D. R. (2015). The functional impact of the intestinal microbiome on mucosal immunity and systemic autoimmunity. Curr Opinion Rheumatol. 27, 381-387.

Martinez-Martinez, R. E., Abud-Mendoza, C., Patino-Marin, N., Rizo-Rodriguez, J. C., Little, J. W., and Loyola-Rodriguez, J. P. (2009). Detection of periodontal bacterial DNA in serum and synovial fluid in refractory rheumatoid arthritis patients. J. Clin. Periodontol. 36, 1004-1010.

McInnes, I. B., and Schett, G. (2011). The pathogenesis of rheumatoid arthritis. N. Engl. J. Med. 365, 2205-2219.

Mikuls, T. R., Payne, J. B., Yu, F., Thiele, G. M., Reynolds, R. J., Cannon, G. W., Markt, J., McGowan, D., Kerr, G. S., Redman, R. S., et al. (2014). Periodontitis and *Porphyromonas gingivalis* in patients with rheumatoid arthritis. Arthritis Rheumatol. 66, 1090-1100.

Nishimura, K., Sugiyama, D., Kogata, Y., Tsuji, G., Nakazawa, T., Kawano, S., Saigo, K., Morinobu, A., Koshiba, M., Kuntz, K. M., et al. (2007). Meta-analysis: diagnostic accuracy of anti-cyclic citrullinated peptide antibody and rheumatoid factor for rheumatoid arthritis. Ann. Intern. Med. 146, 797-808.

O'Dell, J. R., Haire, C. E., Palmer, W., Drymalski, W., Wees, S., Blakely, K., Churchill, M., Eckhoff, P. J., Weaver, A., Doud, D., et al. (1997). Treatment of early rheumatoid arthritis with minocycline or placebo: results of a randomized, double-blind, placebo-controlled trial. Arthritis Rheum. 40, 842-848.

Petersen, T. N., Brunak, S., von Heijne, G., and Nielsen, H. (2011). SignalP 4.0: discriminating signal peptides from transmembrane regions. Nature Methods 8, 785-786.

Pianta, A., Drouin, E. E., Arvikar, S., Strle, K., Crowley, J. T., Wang, Q., Costello, C. E., and Steere, A. C. (2015a). Identification of a broadly immunogenic *Prevotella copri* T cell epitope in patients with rheumatoid arthritis. [abstract]. Arthritis Rheumatol. 67 (suppl 10).

Pianta, A., Drouin, E. E., Wang, Q., Arvikar, S., Costello, C. E., Steere, A. C. (2015b). Identification of N-acetylglucosamine-6-sulfatase and filamin A as novel targets of autoimmune T and B cell responses in rheumatoid arthritis. Ann. Rheum. Dis. 74, (Suppl 2):112.

Pianta, A., Drouin, E. E., Crowley, J. T., Arvikar, S., Strle, K., Costello, C. E., and Steere, A. C. (2015). Annexin A2 is a target of autoimmune T and B cell responses associated with synovial fibroblast proliferation in patients with antibiotic-refractory Lyme arthritis. Clin. Immunol. 160, 336-341.

Pischon, N., Pischon, T., Kroger, J., Gulmez, E., Kleber, B. M., Bernimoulin, J. P., Landau, H., Brinkmann, P. G., Schlattmann, P., Zernicke, J., et al. (2008). Association among rheumatoid arthritis, oral hygiene, and periodontitis. J. Periodontol. 79, 979-986.

Plenge, R. M. (2009). Rheumatoid arthritis genetics: 2009 update. Curr. Rheumatol. Rep. 11, 351-356.

Romero, V., Fert-Bober, J., Nigrovic, P. A., Darrah, E., Haque, U. J., Lee, D. M., van Eyk, J., Rosen, A., and Andrade, F. (2013). Immune-mediated pore-forming pathways induce cellular hypercitrullination and generate citrullinated autoantigens in rheumatoid arthritis. Sci. Transl. Med. 5, 209ra150.

Rosenstein, E. D., Greenwald, R. A., Kushner, L. J., and Weissmann, G. (2004). Hypothesis: the humoral immune response to oral bacteria provides a stimulus for the development of rheumatoid arthritis. Inflammation 28, 311-318.

Round, J. L., Lee, S. M., Li, J., Tran, G., Jabri, B., Chatila, T. A., and Mazmanian, S. K. (2011). The Toll-like receptor 2 pathway establishes colonization by a commensal of the human microbiota. Science 332, 974-977.

Ruff, W. E., and Kriegel, M. A. (2015). Autoimmune host-microbiota interactions at barrier sites and beyond. Trends Mol. Med. 21, 233-244.

Schellekens, G. A., de Jong, B. A., van den Hoogen, F. H., van de Putte, L. B., and van Venrooij, W. J. (1998). Citrulline is an essential constituent of antigenic determinants recognized by rheumatoid arthritis-specific autoantibodies. J. Clin. Investig. 101, 273-281.

Scher, J. U., and Abramson, S. B. (2011). The microbiome and rheumatoid arthritis. Nat. Rev. Rheumatol. 7, 569-578.

Scher, J. U., and Abramson, S. B. (2013). Periodontal disease, *Porphyromonas gingivalis*, and rheumatoid arthritis: what triggers autoimmunity and clinical disease? Arthritis Res. Ther. 15, 122.

Scher, J. U., Sczesnak, A., Longman, R. S., Segata, N., Ubeda, C., Bielski, C., Rostron, T., Cerundolo, V., Pamer, E. G., Abramson, S. B., et al. (2013). Expansion of intestinal *Prevotella copri* correlates with enhanced susceptibility to arthritis. Elife 2, e01202.

Seward, R. J., Drouin, E. E., Steere, A. C., and Costello, C. E. (2011). Peptides presented by HLA-DR molecules in synovia of patients with rheumatoid arthritis or antibiotic-refractory Lyme arthritis. Mol. Cell. Proteomics 10, M110 002477.

Stone, M., Fortin, P. R., Pacheco-Tena, C., and Inman, R. D. (2003). Should tetracycline treatment be used more extensively for rheumatoid arthritis? Metaanalysis demonstrates clinical benefit with reduction in disease activity. J. Rheumatol. 30, 2112-2122.

Sturniolo, T., Bono, E., Ding, J., Raddrizzani, L., Tuereci, O., Sahin, U., Braxenthaler, M., Gallazzi, F., Protti, M. P., Sinigaglia, F., and Hammer, J. (1999). Generation of tissue-specific and promiscuous HLA ligand databases using DNA microarrays and virtual HLA class II matrices. Nat. Biotechnol. 17, 555-561.

Suzuki, K., Sawada, T., Murakami, A., Matsui, T., Tohma, S., Nakazono, K., Takemura, M., Takasaki, Y., Mimori, T., and Yamamoto, K. (2003). High diagnostic performance of ELISA detection of antibodies to citrullinated antigens in rheumatoid arthritis. Scand. J. Rheumatol. 32, 197-204.

Wegner, N., Wait, R., Sroka, A., Eick, S., Nguyen, K. A., Lundberg, K., Kinloch, A., Culshaw, S., Potempa, J., and Venables, P. J. (2010). Peptidylarginine deiminase from *Porphyromonas gingivalis* citrullinates human fibrinogen and alpha-enolase: implications for autoimmunity in rheumatoid arthritis. Arthritis Rheum. 62, 2662-2672.

Yang, Y., Torchinsky, M. B., Gobert, M., Xiong, H., Xu, M., Linehan, J. L., Alonzo, F., Ng, C., Chen, A., Lin, X., et al. (2014). Focused specificity of intestinal TH17 cells towards commensal bacterial antigens. Nature 510, 152-156.

Zeng, M. Y., Cisalpino, D., Varadarajan, S., Hellman, J., Warren, H. S., Cascalho, M., Inohara, N., and Nunez, G. (2016). Gut microbiota-induced immunoglobulin G controls systemic infection by symbiotic bacteria and pathogens. Immunity 44, 1-12.

Zhang, X., Zhang, D., Jia, H., Feng, Q., Wang, D., Liang, D., Wu, X., Li, J., Tang, L., Li, Y., et al. (2015). The oral and gut microbiomes are perturbed in rheumatoid arthritis and partly normalized after treatment. Nature Med. 21, 895-905.

Asquith D L, Miller A M, McInnes I B, Liew F Y. Animal models of rheumatoid arthritis. Eur J Immunol. 2009 August; 39(8):2040-4.

Sturniolo, T., Bono, E., Ding, J., Raddrizzani, L., Tuereci, O., Sahin, U., Braxenthaler, M., Gallazzi, F., Protti, M. P., Sinigaglia, F., and Hammer, J. (1999). Generation of tissue-specific and promiscuous HLA ligand databases using DNA microarrays and virtual HLA class II matrices. Nat. Biotechnol. 17, 555-561.

Arnett F C, Edworthy S M, Bloch D A, et al: The American Rheumatism Association 1987 revised criteria for the classification of rheumatoid arthritis. Arthritis Rheum. 1988, 31: 315-324.

Aletaha D, Neogi T, Silman A J, et al. 2010 Rheumatoid arthritis classification criteria: an American College of Rheumatology/European League against Rheumatism collaborative initiative. Ann Rheum Dis 2010; 69:1580-1588.

Example 2—Two Rheumatoid Arthritis-Specific Autoantigens Correlate Microbial Immunity With Autoimmune Responses in Joints Rheumatoid arthritis (RA) is an HLA class II-associated autoimmune disease, in which arthritogenic T cells drive progressive inflammation and destruction of synovial joints (1). Both genetic and environmental factors are thought to contribute to disease development and progression. The greatest genetic risk factor is HLA-DRB1 susceptibility alleles that share a 5 amino acid sequence in the B1 chain, termed the RA "shared epitope" (SE) (2). HLA-DRB1 SE alleles largely influence the development of seropositive RA, which is defined by positive tests for rheumatoid factor (RF) and/or anti-citrullinated-protein antibodies (ACPA) (3), the latter being the only known specific autoantibodies for this disease (4-6). RF and/or ACPA may develop years before the onset of clinical arthritis (7-9), indicating that autoimmunity may be triggered at sites other than joints in RA patients.

Causative environmental factors are less well characterized. However, T cell epitope mimicry between microbial pathogens and self proteins has been implicated as a possible factor in the induction or exacerbation of autoimmune disease (10-12). In addition, alteration in the oral or gut microbiota may affect mucosal immunity inducing aberrant immune responses affecting joints in RA patients (13, 14). Using high through-put sequencing, Scher et al. showed that *Prevotella* species, including *P. copri*, in the gut microbiota were expanded in stool samples from patients with new-onset RA (NORA), indicating that these organisms might have this role in RA pathogenesis (13). Moreover, a recent study in mice showed that gut dysbiosis contributes to arthritis development via activation of autoreactive T cells in the intestine (15). Proposed mechanisms to link infection and autoimmunity include molecular mimicry between T-cell microbial and host epitopes (16); infection-induced alteration and release of sequestered self antigens (11), or non-specific, infection-induced inflammatory responses which function as adjuvants in the induction of pathogenic autoimmunity (17, 18).

Identification of disease-relevant infectious or self antigens has been challenging in any autoimmune disease, but current discovery-based methods offer innovative approaches to this problem.

A novel approach for antigen detection in chronic inflammatory arthritides was developed in which HLA-DR-presented peptides (T cell epitopes) are identified directly from patients' inflamed synovial tissue, synovial fluid mononuclear cells (SFMC), or peripheral blood mononuclear cells (PBMC) by tandem mass spectrometry (LC-MS/MS), and tested for immunogenicity using patients' samples (19-24). With this approach, it was recently identified an HLA-DR-presented peptide from a 27-kD protein of *P. copri* (Pc-p27), which stimulated T and B cell responses in about 40% of RA patients, but not in patients with other rheumatic diseases or in healthy controls (25). Using the same methodology, 2 novel autoantigens were identified, N-acetylglucosamine-6-sulfatase (GNS) and filamin A (FLNA), that are targets of T and B cell responses which appear to be specific for RA. Both autoantigens are highly expressed in inflamed synovial tissue; they share homologous T cell epitopes with *Prevotella* and several other gut microbes, and they are targets of specific T and B cell responses in patients with RA, providing evidence that may link immune responses to microbial peptides from gut commensals and autoimmune responses affecting joints.

Results

Identification of naturally presented HLA-DR-peptides (T cell epitopes). In a recent study (20), HLA-DR-presented peptides were identified in synovial tissue, SFMC, or PBMC from 5 patients with RA using LC-MS/MS, and immunogenicity of the peptides was determined using patients' samples in ELISpot assays. The findings from one patient (referred to herein as RA1) were of particular interest. RA1 had classic, seropositive RA, with severe symmetrical polyarthritis, a positive test for anti-citrullinated protein antibodies (ACPA), and 2 copies of SE alleles (HLA-DRB1*0401 and 0101). In this patient, an immunogenic HLA-DR-presented peptide derived from a *Prevotella copri* protein (Pc-p27) was identified from her PBMC (25). I was shown that about 40% of RA patients have T and/or B cell responses to Pc-p27 or to the whole *Prevotella copri* organism (25).

In patient RA1, 2 immunogenic HLA-DR-presented human, self peptides derived from N-acetyl-glucosamine-6-sulfatase (GNS) and filamin A (FLNA) were also identified from RA1synovial tissue, and the same FLNA peptide was also found in her PBMC (20). The HLA-DR-presented peptide derived from GNS was predicted to be promiscuous, binding to 24 of the 25 HLA-DR molecules modeled in the program TEPITOPE (26), and the FLNA-derived peptide was predicted to bind 9 of the 25 HLA-DR molecules. With both peptides, this included binding by HLA-DR molecules encoded by SE alleles *0101, *0401, *0404, and *0405. Neither the GNS nor FLNA protein nor the *P. copri* protein had previously been noted to be antigens in RA.

T cell reactivity to N-acetylglucosamine-6-sulfatase and filamin A peptides. To determine the immunogenicity of HLA-DR-presented peptides and their source proteins more broadly, cohort was developed of patients with new-onset RA (NORA) seen prior to therapy with disease-modifying anti-rheumatic drugs (DMARDs), the time when immune responses would be expected to be most robust. For comparison, samples from Lyme arthritis (LA) patients and from healthy control subjects were tested. HLA-DR typing showed that 60% of the 40 RA patients had shared epitope (SE) alleles; 50% of the 10 LA patients and 42% of 15 healthy subjects also had SE alleles. Nevertheless, since patients and control subjects had a range of different HLA-DR alleles and since cell numbers are limited in human patients, the initial approach for determining T cell responses in multiple individuals comprises pooling the original peptide with 3 additional peptides from the same protein that are predicted by the program TEPITOPE to be promiscuous HLA-DR binders (26). In addition, because of limited cells, testing of irrelevant, control peptides in these experiments were not included. However, it was previously shown that RA patients do not have reactivity to peptides derived from endothelial cell growth factor (ECGF) or MMP-10 peptides (21, 23). These autoantigens in Lyme arthritis (LA) are irrelevant in RA.

Figures 10A, 10B:
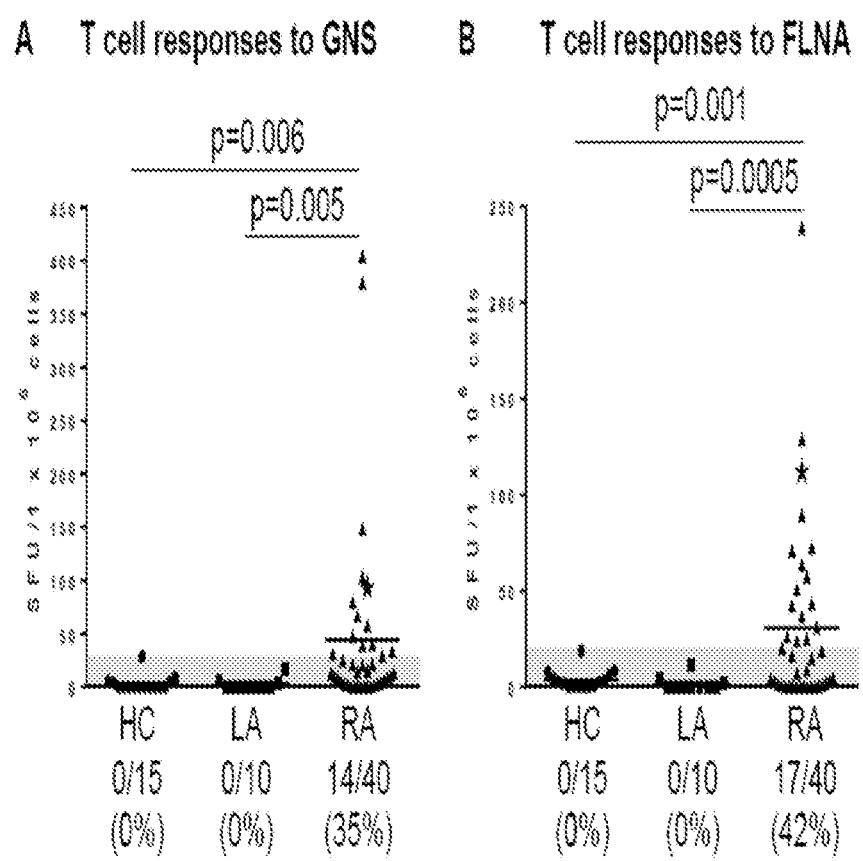
(FIG. 10B) PBMC from patients and control subjects were incubated with a pool of 4 peptides, including the single FLNA HLA-DR presented peptide identified from the synovial tissue and PBMC of patient RA1 and 3 predicted promiscuous HLA-DR binding peptides from FLNA (1 µM each). In each assay, a positive control (phytohemagglutinin) and a negative control (no peptide) were included. The amount of IFN-γ secretion is shown as determined by an ELISpot assay. A positive response was defined as >3 SD above the mean value of the HC (area above the shaded region). The values in the case patient RA1 are indicated with a star. Horizontal lines represent the mean values of each group. The P-values for the unpaired t test with Welch's correction are indicated. SFU, spot forming units per million PBMC.

When PBMC from 40 NORA patients were stimulated with the GNS peptides, 14 of the 40 patients (35%) secreted levels of IFN-γ that were >3 SD above the mean value of HC (P=0.006), using an IFN-γ/IL-17 Double-Color ELISpot assay (FIG. 10A). In comparison, PBMC from patients with Lyme arthritis (LA) lacked reactivity with these peptides (P=0.005). When FLNA peptides were used to stimulate PBMC from the same set of patients and control subjects, 17 of the 40 NORA patients (42%) had IFN-γ levels that were >3 SD above the mean value of HC (P=0.001) and in LA patients (P=0.0005) (FIG. 10B). In RA patients, the predominant response to stimulation with both peptide sets was a Th1-type response with IFN-γ secretion, whereas PBMC from only 3 RA patients secreted IL-17 (data not shown). Altogether, 21 of the 40 patients (52%) had T cell reactivity to GNS and/or FLNA peptides, and 10 (25%) had reactivity with both.

Figure 11A:
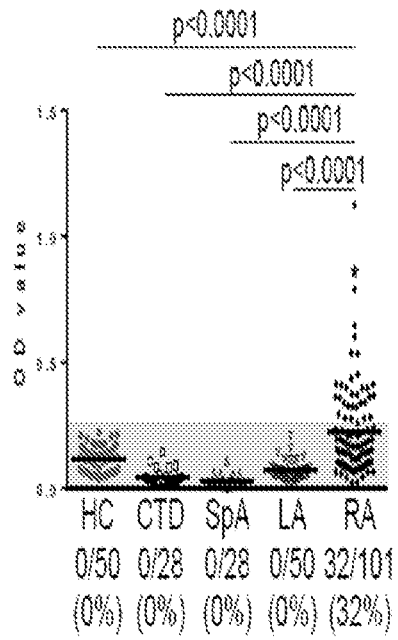
(FIGS. 11A and 11C) Plates were coated with the GNS protein and incubated with serum from patients or control subjects. All serum samples were tested in duplicate for anti-GNS IgG (FIG. 11A) or IgA (FIG. 11C) antibody responses.
Figure 11B:
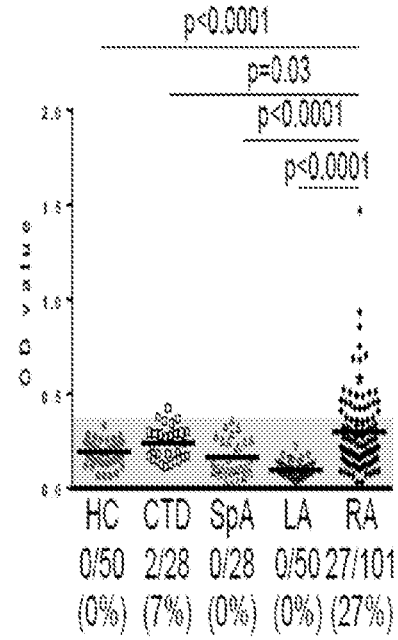
(FIGS. 11B and 11D) Plates were coated with the FLNA protein and incubated with serum from patients or control subjects. All serum samples were tested in duplicate for anti-FLNA IgG (FIG. 11B) or IgA (FIG. 11D) antibody responses. For all analyses, positivity was defined as >3 SD above the mean value of healthy controls (HC) (area above the shaded region). Symbols represent values in individual patients and horizontal lines show mean values. Values in the case patient RA1 are indicated with a star. Only significant P values of unpaired t test with Welch correction are shown. HC, healthy control; CTD, connective tissue diseases; SpA, spondyloarthropathies; LA, Lyme arthritis; RA, rheumatoid arthritis.

B cell reactivity to N-acetylglucosamine-6-sulfatase and filamin A proteins. Since the role of CD4+ T cells would likely be to help B cells to produce autoantibodies to GNS or FLNA, IgG levels to these proteins were examined in serum samples from RA patients and control groups. Since sera (but not PBMC) were also available from patients with chronic RA (CRA), testing was done in 48 NORA patients and in 53 CRA patients. Because the results were similar in both groups, they are presented together here. Of the 101 RA patients, 32 (32%) had IgG antibody responses to GNS that were >3 SD above those in HC (P<0.0001) (FIG. 11A). In contrast, none of the 106 patients with other diseases, including those with Lyme arthritis (LA), spondyloarthropathy (SpA), or connective tissue diseases (CTD), and none of 50 healthy control subjects had positive IgG antibody responses to the protein (in each instance, P<0.0001). Similarly, 27 of the 101 RA patients (27%) had IgG levels to FLNA that were >3 SD above those in HC (P<0.0001), whereas only 2 patients with CTD had borderline positive IgG antibody responses to FLNA, and none of the other control subjects had positive responses (FIG. 11B). Altogether, 48 (48%) of the 101 RA patients had IgG autoantibodies to GNS and/or FLNA, and 10 (10%) had IgG reactivity with both proteins.

Figure 11C:
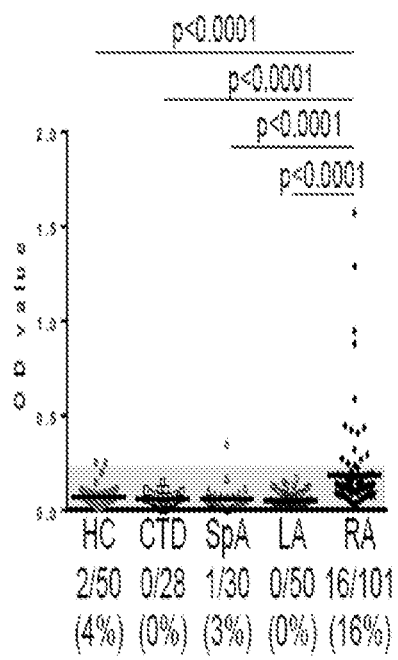
Figure 11D:
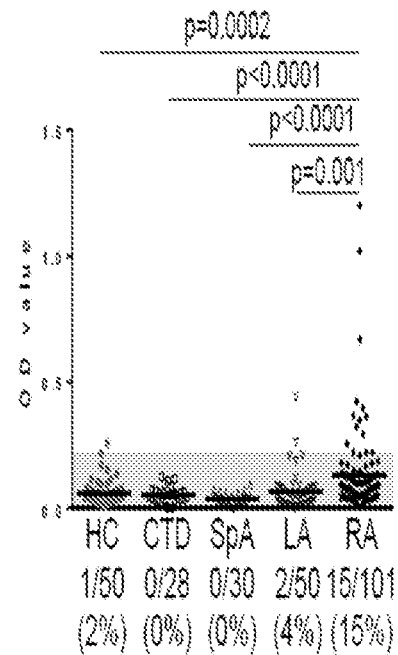

Because autoimmune processes in RA may be triggered at mucosal sites, IgA levels to GNS and FLNA were also tested in serum samples from patients and control subjects. Of the 101 RA patients, 16 (16%) had elevated IgA antibody responses to GNS that were >3 SD above those in HC (P<0.0001) (FIG. 11C). In contrast, of the 106 patients with other rheumatic diseases and 50 healthy control subjects, only 1 patient with spondyloarthropathy had borderline positive IgA antibodies. Similarly, 15 (15%) of the 101 RA patients had FLNA IgA responses that were >3 SD above those in HC (P=0.0002), whereas only 1 healthy subject and 2 patients with LA had low-level positive responses (FIG. 11D). Altogether, 21 (21%) of the 101 RA patients had IgA antibody responses to GNS and/or FLNA, and 10 (10%) had IgA responses to both proteins.

When IgG and IgA responses were considered together, 48 of the 101 RA patients (48%) had IgG responses to GNS and/or FLNA; 21 (21%) had IgA responses to 1 or both of the proteins, and 56 (55%) had IgG and/or IgA responses to the proteins. Of the 14 patients who had T cell responses to GNS peptides, 11 (79%) had IgG and/or IgA antibody responses to the GNS protein. Among the 17 patients who had T cell reactivity with the FLNA peptides, 6 (35%) had IgG and/or IgA antibody responses to FLNA protein. Thus, T and B cell concordance was greater with GNS than with FLNA.

Correlation of antibody responses to *P. copri*, GNS and FLNA. Using these same serum samples (25), IgG and IgA antibody responses were previously tested to two RA-associated bacteria, *Prevotella copri*, a gut microbe, and *Porphyromonas gingivalis*, a periodontal pathogen (27). Antibody responses to *P. copri* were found in 32% of RA patients, but were absent in patients with other connective tissue diseases, spondyloarthropathy, Lyme arthritis, or healthy subjects (25). Therefore, using these data, IgG and IgA antibody responses to these two organisms were correlated with the GNS and FLNA antibody responses determined here.

Figure 12A:
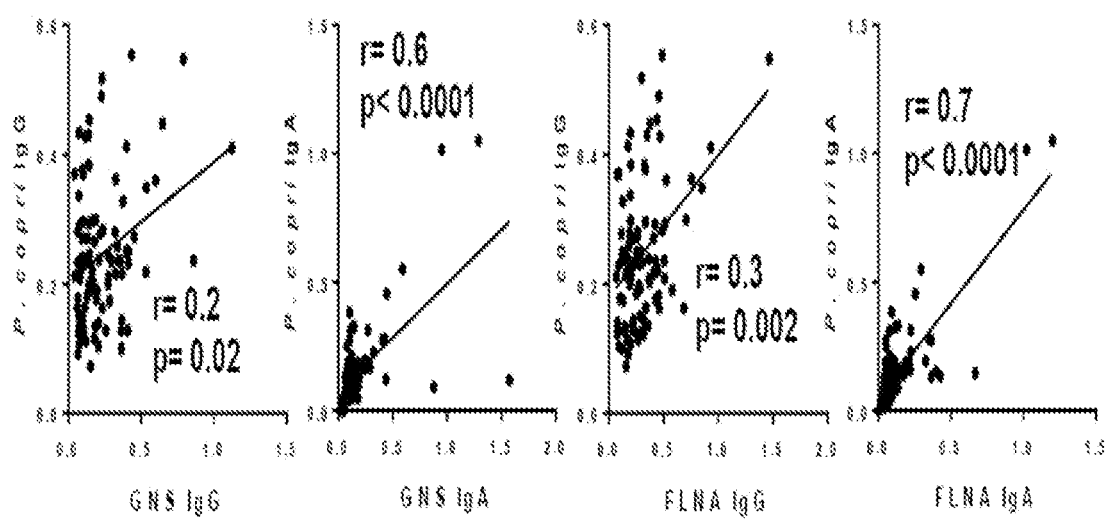
FIG. 12 shows autoantibody correlations with *P. copri* and *P. gingivalis* antibodies. Correlations between anti-GNS or anti-FLNA antibodies (IgG or IgA) and antibodies to *P. copri* (FIG. 12A), or *P. gingivalis* (FIG. 12B), in 101 RA patients. The r and P values for the corresponding statistical comparisons are indicated, as determined by Spearman correlation test.
Figure 12B:
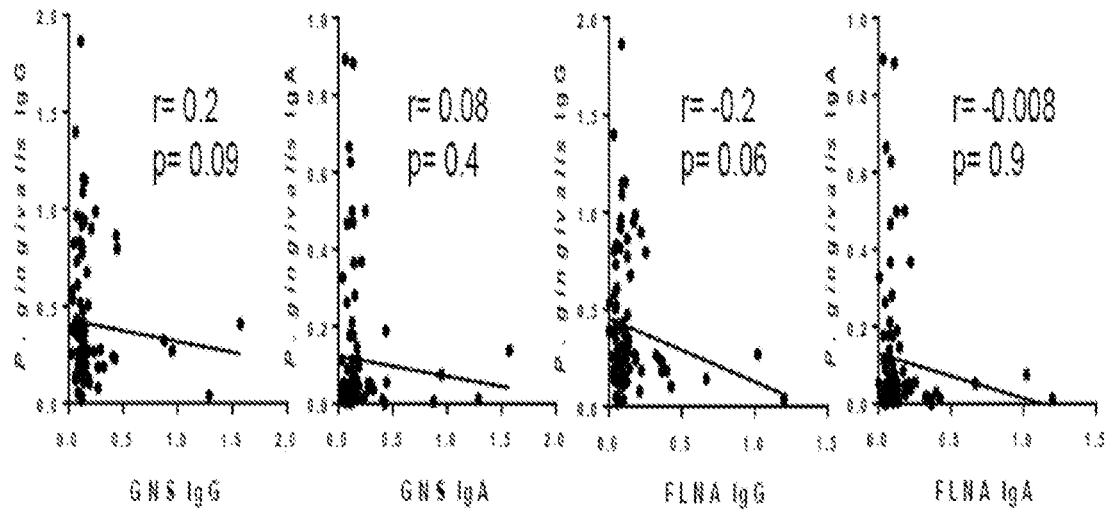

In RA patients, the levels of anti-GNS IgG and IgA antibodies strongly correlated with *P. copri* antibody responses (P=0.002 and P<0.0001, respectively) and a similar correlation was found between anti-FLNA IgG and IgA antibody responses and *P. copri* antibodies (P<0.0001 and P<0.0001, FIG. 12A). In contrast, anti-GNS and anti-FLNA IgG or IgA levels did not correlate with *Porphyromonas gingivalis* antibody responses (FIG. 12B). Additionally, there were no correlations among these parameters in healthy subjects. Thus, in RA patients, the higher the IgG or IgA antibody responses to *P. copri*, the greater the autoantibody responses to these autoantigens.

Figures 13A, 13B, 13C, 13D:
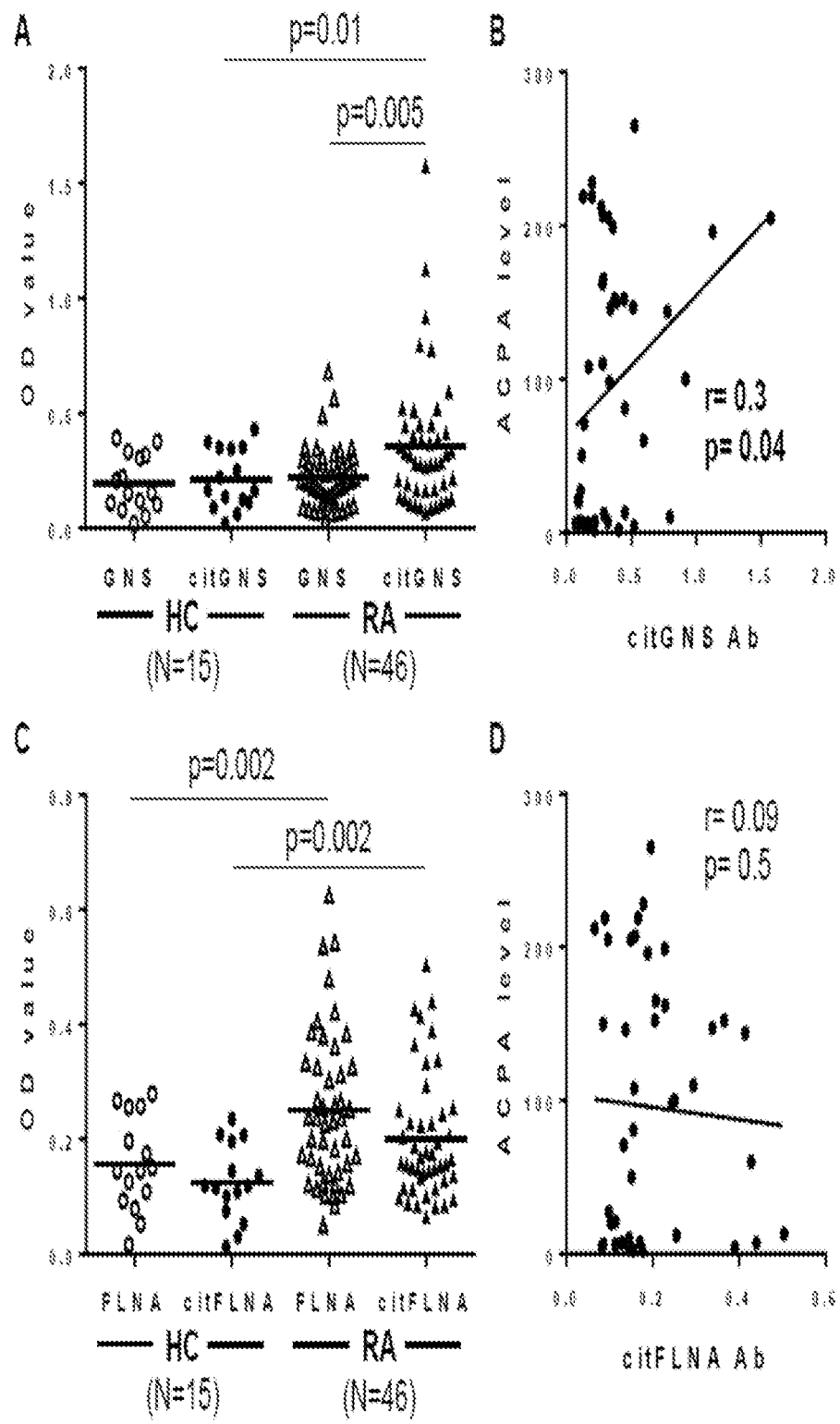
(FIG. 13B) Correlation between IgG antibody responses to citrullinated GNS or to citrullinated FLNA (FIG. 13D), and ACPA levels in the 46 patients with RA. The r and P values for the Spearman correlations are indicated.

Testing of citrullinated N-acetylglucosamine-6-sulfatase and filamin A proteins. Because citrullinated autoantigens are thought to play a central role in RA, particularly in those with SE alleles, it was investigated whether autoantibody responses to GNS or FLNA were greater when these proteins were citrullinated. For this purpose, the native proteins were citrullinated in vitro using recombinant human PAD4 enzyme. Using samples from 46 RA patients in whom enough serum still remained, IgG antibody responses were higher to citrullinated GNS compared with responses to the uncitrullinated protein (P=0.005), whereas the responses were negative to both forms of the protein in 15 healthy control subjects (FIG. 13A). Moreover, the magnitude of anti-citrullinated-GNS antibody responses correlated with ACPA levels in these patients (P=0.03, FIG. 13B). In contrast, IgG antibody responses to citrullinated and uncitrullinated FLNA were not significantly different in the 46 patients (FIG. 13C), and the levels of anti-citrullinated-FLNA antibodies did not correlate with ACPA levels (FIG. 13D). These results indicate that the GNS protein may be citrullinated in vivo in RA patients, whereas the FLNA protein is not.

Utility of GNS and FLNA autoantibodies evaluation in the diagnosis of rheumatoid arthritis. In the patient cohort, 70 (69%) of the 101 new-onset and chronic RA patients were seropositive for ACPA and/or RF, which are standard, commercially available autoantibody determinations for support of the diagnosis in RA patients. Among the 31 patients who did not have a positive test for ACPA and/or RF, 13 had a positive test for IgG and/or IgA GNS autoantibodies and 9 had positive test for IgG and/or IgA FLNA autoantibodies. Taken together, 17 of 31 seronegative patients (55%) had such autoantibodies, 15 of whom could be identified with the IgG test alone. Overall, when autoantibody responses to GNS and FLNA were combined with standard autoantibody determinations, 87 (86%) of the 101 RA patients had a positive test result for support of the diagnosis, and only 14 (14%) lacked a specific marker for RA.

Figures 14A, 14B:
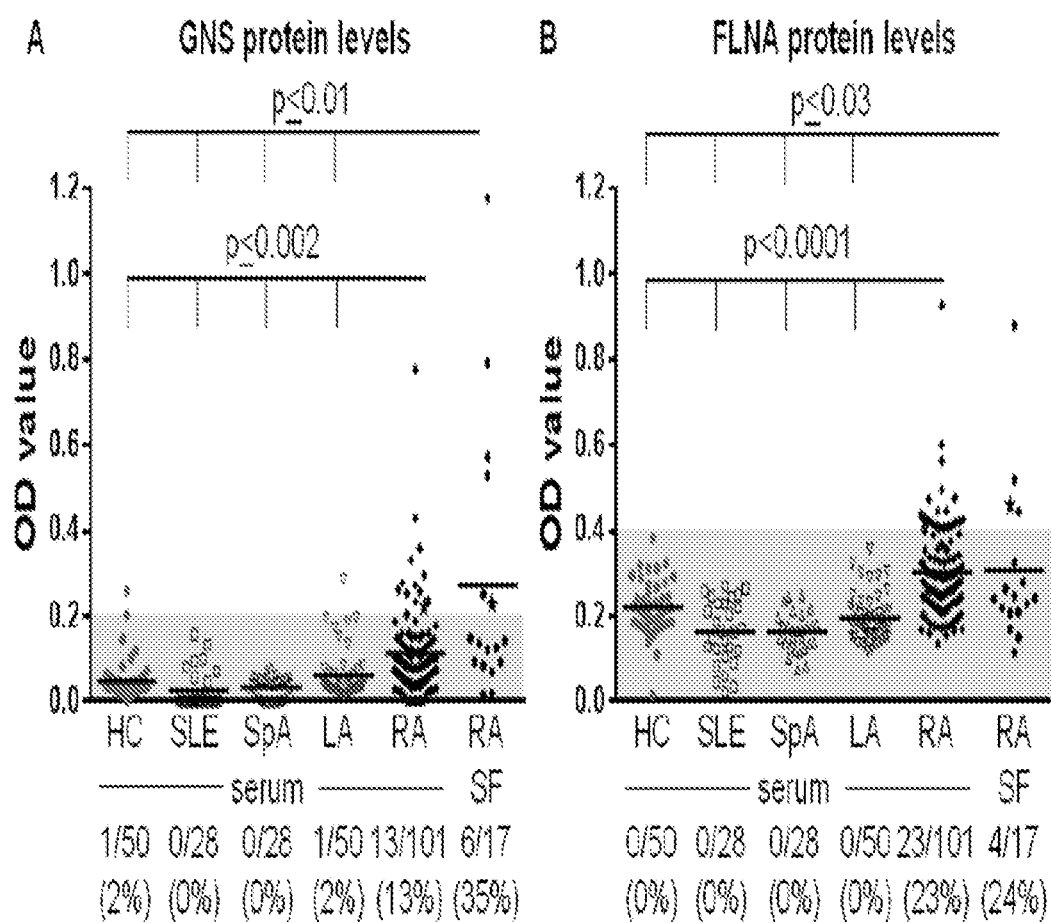
(FIG. 14A) GNS and (FIG. 14B) FLNA protein concentrations were measured in serum and synovial fluid (SF) samples in patients with rheumatoid arthritis (RA), and in serum samples from patients with connective tissue diseases (CTD), spondyloarthropathies (SpA), Lyme arthritis (LA), and in healthy controls (HC) subjects. (A) GNS protein concentrations and (B) FLNA protein concentrations are shown, as measured by ELISA assay. For both analyses, positivity was defined as >3 SD above the mean value of healthy control (HC) subjects (area above the shaded region). Symbols represent values in individual patients and horizontal lines show mean values. The value in the case patient RA1 are indicated with a star. Only significant P values of unpaired t test with Welch correction are shown.

N-acetylglucosamine-6-sulfatase and filamin A protein levels in serum and joints. For a self-protein to become the target of autoimmune responses in RA patients' inflamed joints, one would predict that the protein would be present in high concentrations there. For this purpose, GNS and FLNA protein concentrations in serum samples were measured from the 101 RA patients and in synovial fluid (SF) from 17 patients in whom such samples were available. The levels of GNS were higher in the serum of RA patients compared with those in control groups (P<0.002, FIG. 14A), and in RA patients, the levels of this protein tended to be higher in SF than in serum. Similarly, the levels of the FLNA protein were significantly greater in the serum of RA patients than in healthy controls (P<0.0001), but in RA patients, FLNA protein levels in SF and serum were similar (FIG. 14B).

Figure 15:
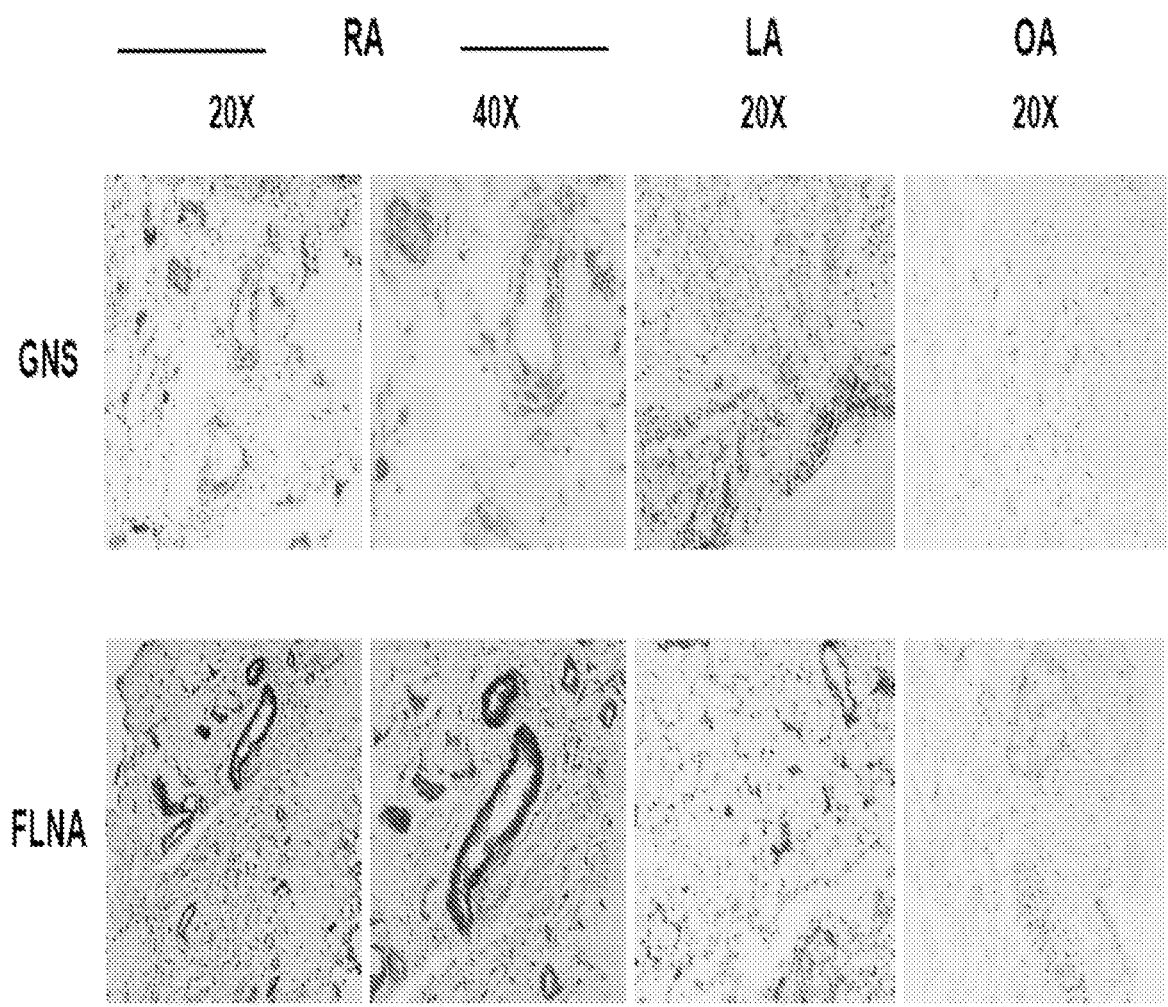
FIG. 15 show immunohistochemical staining of synovial tissue for GNS and FLNA. Synovial tissue images from a representative patient with rheumatoid arthritis (RA), one with Lyme arthritis (LA) and one with osteoarthritis (OA) are shown for expression of the GNS or the FLNA protein. Specific staining of the self proteins GNS or FLNA were visualized as brown. The hematoxylin staining was visualized as purple. Images were taken at 20× magnification, and 40× magnification was used for the RA patient to highlight the staining around blood vessels.

To gain further insight into protein abundance and distribution, synovial tissue from 10 patients, 4 with RA, and 3 each with LA or osteoarthritis (OA), were stained for expression of GNS and FLNA, using immunohistologic methods. GNS showed a fine, reticular pattern in and around endothelial cells in 3 of the 4 RA patients, but not in those with LA or OA (FIG. 15). FLNA was intensely expressed in the tunica muscularis around blood vessels and in large or elongated cells, presumably synoviocytes, and it was also faintly expressed in the extracellular matrix. FLNA expression was found in all RA patients, and lesser staining was seen in 2 LA patients, but not in OA patients (FIG. 15). Thus, in RA, these two proteins were present in inflamed synovial tissue, particularly around blood vessels, where they could become targets of autoimmune responses.

Figures 16A, 16B:
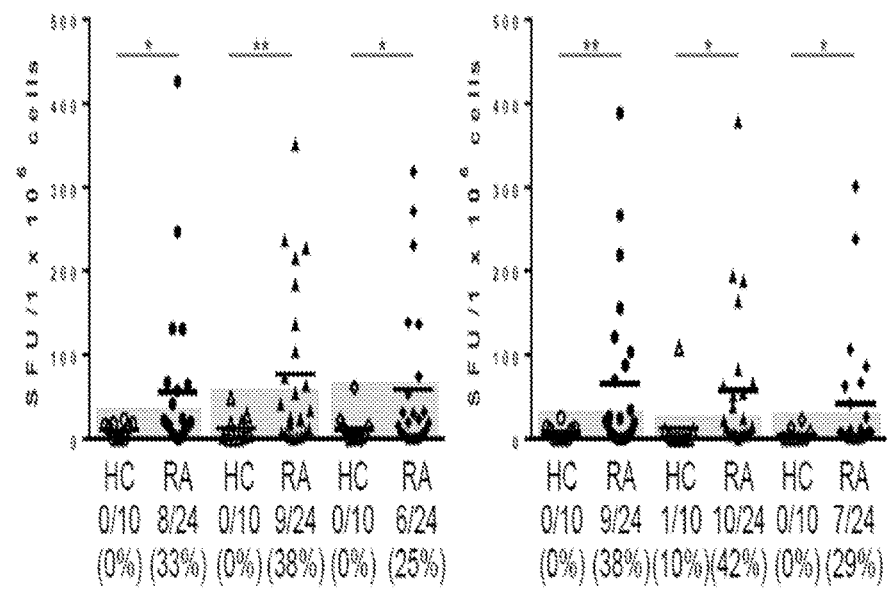
(FIG. 16A) Sequence alignment of the self and corresponding microbial peptides are shown (Clustal Omega), and the predicted binding frames of the self peptides are given for the HLA-DRB1*0101 and 0401 molecules. The amino acids that occupy the P1 position (TEPITOPE predicted 3 binding registers for GNS (both HLA-DRB1*0101 and 0401) and 2 for FLNA (HLA-DRB1*0401) and positions P2 trough P9 were identified. The line through the amino acid residues indicates the peptide binding register contains amino acid with an R-group that may not interact favorably with one of the MHC binding pockets.
(FIG. 16B) PBMC from 24 RA patients and 10 healthy controls (HC) were incubated with one of the 2 self peptides (GNS or FLNA), or each of the 2 corresponding microbial peptides (1 µM each). In each assay, a positive control (phytohemagglutinin) and a negative control (no peptide) were included. The amount of IFN-γ secretion is shown, as determined by ELISpot assay. A positive response was defined as >3 SD above the mean value of the HC (area above the shaded region). Horizontal lines represent the mean values of each group. P values were calculated using unpaired t test with Welch correction. *, P<0.05; **, P<0.005. SFU, spot forming units.

Sequence homology between T cell epitopes of microbial and self peptides. In an effort to determine whether T cell epitope mimicry may play a role in linking Prevotella reactivity with GNS and FLNA autoimmune responses, the sequence of each of the 2 self-peptides isolated from patient RA1 was used first to search for regions of similarity with any microbial protein using the microbial protein database in the Blastp program (https://blast.ncbi.nlm.nih.gov/Blast.cgi). For both self-peptides, Prevotella sp. peptides were among the top sequences producing significant alignment, specifically in areas predicted to be in the HLA-DR binding groove. Therefore, the search for sequence similarity was refined by screening only microbial sequences from Prevotellaceae (taxid:171552). To evaluate sequence homology, self and microbial peptides were aligned using the program Clustal Omega (28). The peptide derived from GNS had 67% sequence homology with a peptide from the Prevotella arylsulfatase protein (WP_062433009) (FIG. 16A), which was predicted to have a periplasmic location by CELLO software (29). Importantly, the major area of homology for this microbial peptide was restricted to amino acids predicted to be in the HLA-DR binding groove (FIG. 16A). For the Prevotella peptide, 5 of the 9 amino acids were identical to one of the predicted binding registers (P1=the first F) in the GNS peptide. Moreover, the peptides shared amino acid identity at the P1, P4, and P6 sites, which are critical for peptide binding, as well as in the flanking regions at each end of the peptide, which also influence peptide binding (FIG. 16A). The FLNA peptide had 80% identity with a peptide derived from an uncharacterized Prevotella protein (WP_028897633) (FIG. 16A), which was predicted to have an extracellular location (a secreted protein). Moreover, the major area of homology was again found in the HLA-DR binding groove where 7 of the 9 amino acids were identical in the Prevotella and FLNA peptides and the remaining 2 amino acids had conserved properties (FIG. 16A).

For comparison, GNS and FLNA sequences were analyzed for homology with Porphyromonas gingivalis, a periodontal pathogen of interest in RA, using Porphyromonadaceae (taxid:171551) as the reference database in the Blastp search. However, no homology was found between P. gingivalis and GNS or FLNA sequences. P. gingivalis also stimulates antibody responses in the subgroup of RA patients who have periodontal disease (27, 30), but there is little overlap between RA patients with P. gingivalis antibodies and those with P. copri antibodies (25).

Instead, among the Porphyromonadaceae, the GNS epitope had partial sequence similarity with a peptide from the periplasmic protein N-acetylgalactosamine-6-sulfatase of Parabacteroides sp. (WP_046148720) (FIG. 16A). Thus, similar to the homology between the GNS peptide and the peptide from the Prevotella arylsulfatase protein, the Parabacteroides protein was also a sulfatase. These enzymes are key in the adaptation and persistence of human commensal bacteria in the gut (31, 32). Moreover, the Parabacteroides peptide had 4 amino acids identical to the GNS peptide and 1 amino acid with conserved properties. These included amino acids with shared identity in the P1 through P4 and P6 sites. A similar evaluation of the FLNA peptide showed sequence homology with a predicted cytoplasmic uncharacterized protein of Butyricimonas sp. (WP_065219401.1), another gut commensal. The Butyricimonas peptide shared identity with 6 of 9 amino acids in one of the predicted HLA-DR registers (P1=F) of the FLNA peptide, and 2 of the 3 remaining amino acids had conserved properties (FIG. 16A). Prevotella, Parabacteroides, and Butyricimonas are each members of the Bacteroidetes phylum, one of the two major phyla of gut commensal organisms.

T cell responses to homologous microbial and self peptides. To address whether patients had reactivity with these self epitopes and the corresponding microbial epitopes, ELISpot assays were preformed with each of these peptides using PBMC from the 24 NORA patients in whom enough cells remained and in 10 HC. When cells were stimulated with the GNS peptide or each of the 2 corresponding microbial peptides (one derived from *Prevotella* and the other from *Parabacteroides*), Th1 cell reactivity was found with all 3 peptides. Of the 24 RA patients, 8 (33%) had T cell reactivity with the GNS peptide, 9 (38%) showed responses to the *Prevotella* peptide, and 6 (25%) had reactivity with the *Parabacteroides* peptide that were >3SD above the mean values in HC (FIG. 16B). Of the 8 patients who had reactivity with the GNS peptide, 7 also had responses to the microbial peptides. When PBMC were incubated with the FLNA peptide, 9 of the 24 RA patients (38%) had T cell responses; 10 (42%) showed reactivity with the corresponding *Prevotella* peptide, and 7 (29%) had responses to the *Butyricimonas* peptide (FIG. 16B). Furthermore, all 9 patients with reactivity with the FLNA peptide also had responses to the microbial peptides. Thus, except for one patient, the same patients who had reactivity with the GNS and/or FLNA peptides also had responses to the corresponding microbial peptides. Additionally, among the microbial peptides, there was a trend toward a higher percentage of patients who had reactivity with the *Prevotella* peptides than with the other gut commensals.

Figures 16C, 16D:
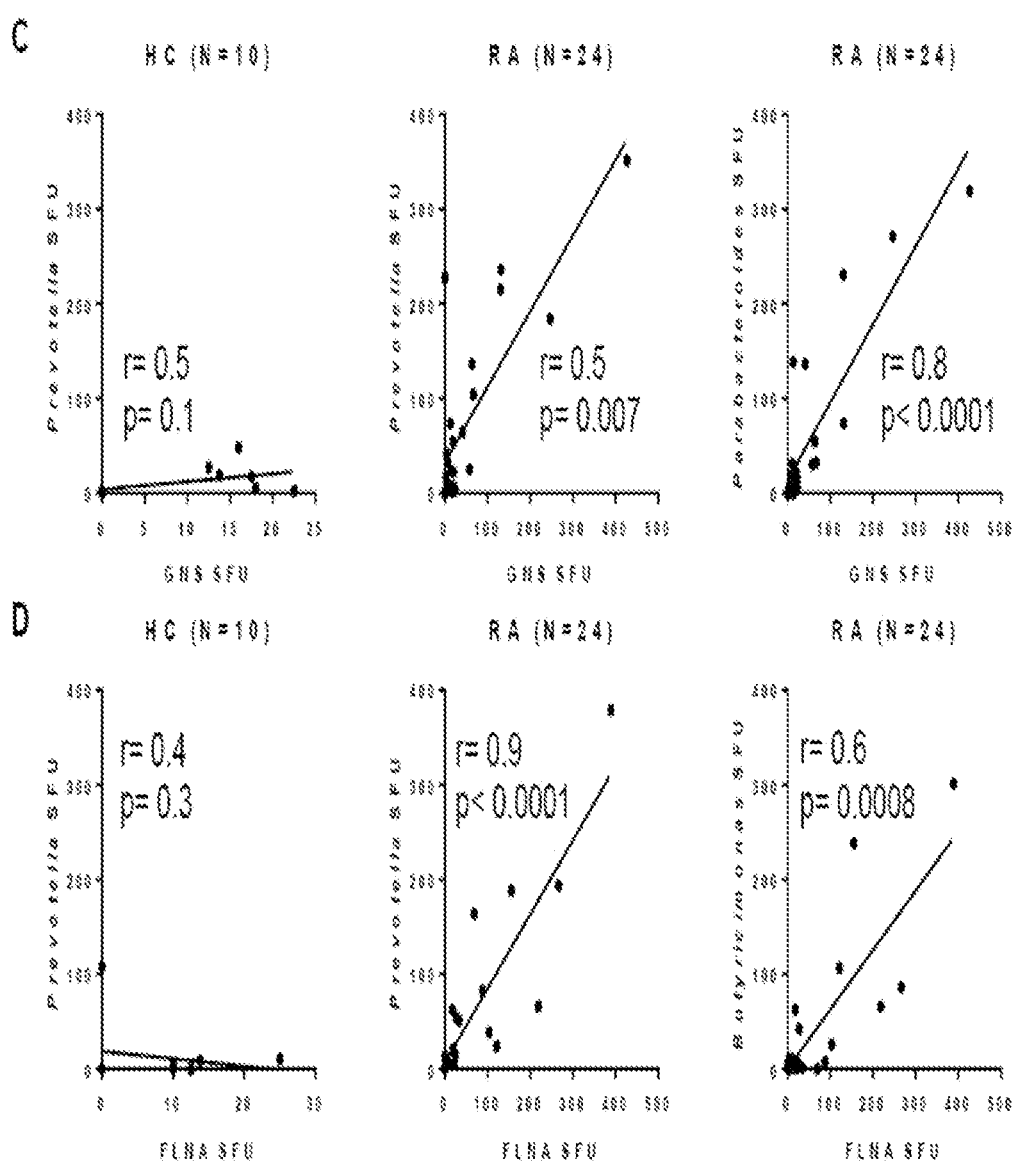
(FIG. 16C) Correlations between the T cell reactivity to the GNS peptide and the 2 corresponding microbial peptides, one derived from the *Prevotella* arylsulfatase protein and the other one from the *Parabacteroides* N-acetylgalactosamine-6-sulfatase protein.
(FIG. 16D) Correlations between the T cell reactivity to the FLNA peptide and the 2 corresponding microbial peptides derived from two hypothetical protein, one from *Prevotella* sp. and the other one from *Butyricimonas* sp. P and r values were calculated using Spearman correlation.

Moreover, when the magnitude of the T cell responses to each self peptide was correlated with that of the corresponding microbial peptides, the responses to the GNS or FLNA peptide strongly correlated with reactivity to each of the two microbial peptides (in each instance, P<0.0001, FIGS. 16C and D). Therefore, the stronger the response to the microbial peptides, the higher the response to the self peptide. In contrast, PBMC from 10 HC did not show a correlation with any of the self or microbial peptides (FIGS. 16C and 16D).

Figures 17A, 17B:
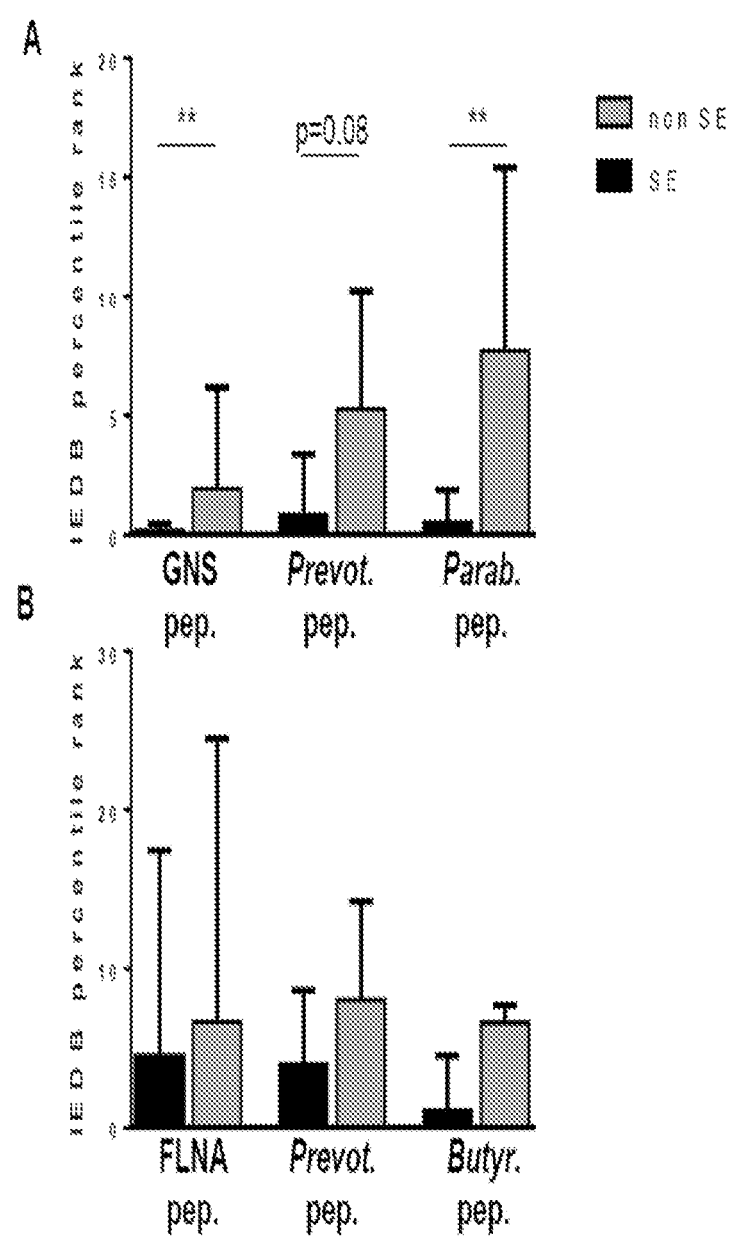
(FIG. 17A) MHC class II binding prediction of the GNS peptide and the corresponding microbial peptides.
(FIG. 17B) MHC class II binding prediction of the FLNA peptide and the corresponding microbial peptides. SE alleles: *0101, *0102, *0401, *0404, *1001. Non SE alleles: *0103, *0301, *0403, *0803, *1101, *1201, *1302, *1501, *1601. Prevot., *Prevotella*; Parab., *Parabacteroides*; Butyr., *Butyricimonas*. Data represent median values with interquartile ranges. P values were calculated using Mann Whitney test. **, P<0.005.

Using an in silico prediction method (Immune Epitope Database and Analysis resource, IEDB), the GNS peptide and the corresponding microbial peptides were predicted to bind HLA-DR molecules encoded by "shared epitope" (SE) alleles with significantly higher affinity than non-SE alleles (FIG. 17A). In addition, there was a trend toward greater affinity of SE binding of the FLNA peptide and the corresponding microbial peptides (FIG. 17B). Of the 24 RA patients, 15 (62%) had SE alleles. Consistent with the IEDB binding predictions, 9 of 11 patients (82%) with self and microbial T cell reactivity had SE alleles compared with 5 of 13 patients (38%) without T cell responses to these antigens (P=0.05). Thus, patients who had reactivity with the self peptides often responded to the corresponding microbial peptides; the magnitude of the self responses showed significant correlation with the microbial responses, and these responses were more frequent in patients with SE alleles.

Discussion

Rheumatoid arthritis (RA) is an HLA class-II associated autoimmune disease in which mucosal immunity, often resulting from interaction with oral or gut microbes or from inhaled antigens in the lung, is hypothesized to cause autoimmune phenomena leading to joint inflammation and damage. However, the factors linking mucosal immunity to autoimmunity in joints have been unclear. In this study in which HLA-DR-presented peptides were identified directly from patients' synovial tissue or PBMC, two novel self-antigens, N-acetylglucosamine-6-sulfatase (GNS) and filamin A (FLNA), were shown to be targets of T and B cell responses in 52% and 56% of RA patients, respectively. Importantly, the GNS and FLNA HLA-DR-presented T cell epitopes have considerable sequence homology with *Prevotella* epitopes and with similar epitopes from several related gut commensals belonging to the same order, particularly in areas predicted to be in the HLA-DR binding groove. Moreover, T cell responses to the corresponding microbial and self peptides correlated strongly, indicating that T cell epitope mimicry may provide a potential link between mucosal immunity and immune responses in affected joints. Moreover, GNS and FLNA autoantibodies correlated with *P. copri* antibody responses. This finding can also be due to cross-reactive *Prevotella* and host protein B cell epitopes, but the recombinant microbial proteins to test this hypothesis directly is lacking. Alternately, this correlation might simply be a reflection of T cell help resulting from T cell epitope mimicry.

The presence of natural IgM, IgG, or IgA autoantibodies has been reported in the serum of normal control subjects, characterized by broad reactivity to self and microbial antigens (33, 34). However, these findings cannot be explained simply by non-specific physiological responses. First, GNS and FLNA autoantibodies were increased specifically in a large subgroup of RA patients, and not in those with other rheumatic diseases or in HC. Second, these self autoantibodies correlated strongly with *P. copri* antibodies, but not with *Porphyromonas gingivalis* antibodies. Third, RA patients, but not healthy subjects, often had both T and B cell responses to these self antigens. For control of the microbiota, the generation of specific, high affinity IgA antibody responses requires T and B cell interactions (35), whereas the "natural" antibody pool consists primarily of low-affinity polyreactive IgA antibodies whose production is independent of T cell help (36-38).

Currently, the only known antibody responses that are specific for RA are directed against citrullinated proteins, particularly to enolase, vimentin, and fibronectin (39). Moreover, there is hypercitrullination of a range of proteins in the joints of many RA patients (40). The GNS protein appeared to be citrullinated in vivo and antibodies to it correlated with ACPA levels, whereas antibody levels to the FLNA protein, which did not appear to be citrullinated, did not correlate with ACPA levels. Moreover, HLA-DR molecules encoded by RA "shared epitope" alleles bound the GNS peptide and to a lesser degree the FLNA peptide with higher affinity than non-SE alleles, and SE alleles largely influence the generation of ACPA (3).

Both self antigens, which are often highly expressed in RA synovial tissue, represent good autoimmune targets. GNS is an enzyme located in lysosomes and is involved in the degradation and recycling of different molecules, such as glycosaminoglycans (GAGs) (https://ghr.nlm.nih.gov/gene/GNS), a major component of joint cartilage and other soft connective tissues (41). FLNA is an ubiquitous, fundamental protein for building the cell cytoskeleton and for organization of the extracellular matrix (42). In addition, FLNA is required for cell-cell contact in vascular development (43). Consistent with its function, the FLNA protein was especially prominent in the tunica muscularis around blood vessels in RA synovial tissue, and was also faintly expressed in the extracellular matrix. However, it is not yet clear why the GNS protein was seen only in a reticular pattern around blood vessels. Nevertheless, the important point is that both host proteins would be available for HLA-DR presentation in synovial tissue and they represent potential targets for autoimmune responses.

Based on high through-put sequencing of stool samples, gut dysbiosis has been shown in two studies of RA patients (13, 14) and overexpansion of *Prevotella* sp., particularly *P. copri*, was reported in one study (13). However, little is known about potential bowel pathology in RA. The major limitation of the study is the lack of specific information about pathology or immune responses in the bowel. The study of NORA patients was originally intended as a study of mouth flora and periodontal disease (30), and therefore, collection of stool samples was not a part of the protocol. Nevertheless, the finding of gut dysbiosis favoring *Prevotella* (13), the identification of *P. copri* as an immune-relevant bacterium in RA (25), and the finding here of specific T and B cell responses to *Prevotella* and corresponding GNS and FLNA epitopes indicate that mucosal immune responses in the gut may be a part of the disease in a sizable subgroup of RA patients. Although DMARDs therapy may resolve dysbiosis (14) and *P. copri* overexpansion (13), immune reactivity to the organism, once triggered, appeared to persist or even increase in patients with chronic RA who were taking these medications. In contrast, patients with spondyloarthropathy or post-infectious, antibiotic-refractory Lyme arthritis, which may also be treated with DMARDs, did not have reactivity with this organism (25).

Taken together, the studies described herein highlight a mechanism that may link gut and joint inflammation. Thus, dysbiosis or low-grade gut inflammation can compromise the mucosal barrier resulting in leakage of commensal organisms, leading to activation of lymphocytes targeting microbial antigens. Evidence that T cell epitopes of a related order of gut microbes, particularly *Prevotella* species, may cross-react with self epitopes of highly expressed proteins in joints, especially in patients with SE alleles is provided. T cells activated by microbial peptides at mucosal surface may then home to inflamed joints and cross-react with homologous self antigens. In addition, as previously reported (25), commensal organisms or their remnants or microbial-activated APCs may occasionally home to joints where they further amplify joint inflammation and re-stimulate self-reactive T cells. Thus, an initial trigger in the gut mucosa activates cross-reactive microbial immune responses which have the potential to shift to an autoimmune phenotype at sites where the homologous self antigens are expressed. Even though proof of cross-reactivity will require the cloning of single T cells, the prominence of homologous epitopes among multiple related families of gut microbes and epitopes from two self proteins in synovial tissue, the greater affinity of HLA-DR molecules encoded by SE alleles in binding these epitopes, and the demonstration that RA patients often have T cell responses to corresponding microbial and self epitopes indicate the potential for these immune responses to have a role in RA pathogenesis. These mechanisms are the entire explanation for the marked inflammatory and proliferative responses in the RA synovial lesion. Rather, they play a role in linking gut and joint immune responses and in amplifying synovial inflammation in a large subgroup of RA patients.

Although knowledge of bowel pathology is not yet clear in RA patients, the identification of immune responses to *P. copri*, GNS and FLNA has practical implications regarding the diagnosis and treatment of the disease. First, these immune responses appear to be specific for RA. As shown here, the addition of GNS and FLNA to standard autoantibody determinations (ACPA and RF) increased the percentage of seropositive patients from 69% to 86%, improving diagnostic support for some patients with seronegative RA, which currently lack specific markers. Furthermore, inclusion of citrullinated GNS in a test for ACPA increases the sensitivity of that testing. These determinations have increased in importance because earlier treatment with DMARDs may improve long-term outcomes, whereas lack of diagnostic markers for seronegative patients may delay appropriate DMARD treatment, leading to less favorable clinical outcomes (44, 45). Finally, in addition to DMARDs, identification of patients with these antibody responses may allow the testing and development of adjunctive forms of treatment, such as brief, targeted antibiotic regimens or diet alterations. Ultimately, the identification of pathogenic T cell epitopes in synovial tissue, as was done here, may make it possible to engineer blocking peptides, which would limit autoimmune stimulation and ameliorate these presumably disadvantageous autoimmune responses.

Methods

Patients and Control Subjects.

The study, "Autoantigens in RA," was approved by the Human Investigations Committee at Massachusetts General Hospital (MGH) (2008-2014). The 101 study patients met the American College of Rheumatology/European League Against Rheumatism Collaborative Initiative criteria for that disease (46). Of the 101 patients, 49 had new-onset RA (NORA) for <12 months and had not yet been treated with DMARDs. The remaining 52 patients had chronic RA (CRA) of >1 year's duration (usually for many years), often treated with DMARDs. For isolation of HLA-DR-presented peptides, synovial tissue and peripheral blood mononuclear cells (PBMC) were obtained from patient RA1 who was undergoing arthroscopic synovectomy. To test implicated peptides and their source proteins for immunoreactivity in additional patients, PBMC and serum samples were collected from patients with NORA, but only serum samples were available from patients with CRA.

For other comparison groups, serum samples were collected from 28 patients with connective tissue diseases (CTD), including systemic lupus, mixed connective tissue disease, scleroderma, and Sjogren's syndrome, from 28 patients with spondyloarthropathy (SpA), and from 50 patients with Lyme arthritis (LA). Additionally, serum samples and PBMC were collected from 15 healthy hospital personnel who did not have a history of RA or other autoimmune diseases, and serum samples were obtained from 40 healthy blood bank donors. HLA-DR typing was performed on blood samples from all RA or LA patients and from healthy subjects at the American Red Cross Laboratory in Dedham, Mass. All patients and control subjects gave written informed consent.

Enzyme-Linked Immunospot (ELISpot) T Cell Assay.

A detailed description of the methods for isolation and identification of HLA-DR presented peptides is given in previous publications (19, 20). In the current study, all non-redundant HLA-DR-presented peptides identified from patient RA1 were synthesized (Mimotopes, Australia) and tested for reactivity in sets of 3 (1 µM of each peptide) with the patient's PBMC using IFN-γ ELISpot assays. In this initial screen, 2 self-peptides derived from GNS and FLNA were implicated; the remaining 138 peptides showed no reactivity. For testing in larger numbers of patients and control subjects who would have a range of HLA-DR genotypes, the original peptides identified from the patient (shown in bold) and 3 additional promiscuous peptides that were predicted to bind >16 HLA-DR molecules were synthesized and HPLC-purified in the MGH Core Facility. The sequences of the GNS peptides were as follows: 47PNVVLLLTDDQDE59 (SEQ ID NO: 13), 222FEPFFM- MIATPAPH235 (SEQ ID NO: 14), 451TYACVRTMSALWNLQ465 (SEQ ID NO: 15), 504NYRLMMLQSCSGPTC518 (SEQ ID NO: 16). The sequences of the FLNA peptides were as follows: 73DGLRLIALLEVLSQKK88 (SEQ ID NO: 17), 118SIKLVSIDSKAIVDG132 (SEQ ID NO: 18), 416VEVVIQDPMGQKG428 (SEQ ID NO: 19), 2446NPAEFVVNTSNAGAG2460 (SEQ ID NO: 20).

To assess microbial sequence homology with the GNS peptide 222FEPFFMMIATPAPH235 (SEQ ID NO: 21), the following microbial peptides were tested: 231KKPFFMMVAMNPPH245 (SEQ ID NO: 22), which was derived from the arylsulfatase protein of *Prevotella* sp. (WP_062433009.1) and 247DVPFFMMWTTPLPH261 (SEQ ID NO: 23), derived from the N-acetylgalactosamine-6-sulfatase of *Parabacteroides* sp. (WP_046148720.1).

To evaluate the microbial sequence homology for the FLNA peptide 2446NPAEFVVNTSNAGAG2460 (SEQ ID NO: 24), the following microbial peptides were tested: 133QGFVVKTANAGAL146 (SEQ ID NO: 25), which was derived from an uncharacterized protein of *Prevotella* sp. (WP_028897633.1) and 90ANFMINVSNAGAL103 (SEQ ID NO: 26), derived from an uncharacterized protein of *Butyricimonas* sp. (WP_065219401.1). The RA patients' PBMC were stimulated with the pool of peptides or single peptides, and analyzed for reactivity with a human IFN-γ/IL17 Double-Color ELISpot kit (Cellular Technology Limited). All peptides (1 µM) were tested in duplicate wells, as were positive (phytohemagglutinin) and negative (no antigen) control samples. After 5 days, cells were transferred to ELISpot plates coated with IFN-γ/IL17 antibodies, and incubated overnight. Images of wells were captured using ImmunoSpot series 3B analyzer, and spots were counted using ImmunoSpot software. A positive T cell response was defined as 3 standard deviations (SD) above the mean value of healthy control subjects.

ELISA for Serum IgG and IgA Anti-GNS and Anti-FLNA Autoantibodies.

ELISA plates were coated with 0.5 µg/ml of recombinant human N-acetylglucosamine-6-sulfatase (Novoprotein, Summit, N.J.) or filamin A (Novusbio, Littleton, Col.) overnight at 4° C. Subsequent incubations and washes were performed at room temperature. After washing with phosphate buffered saline with 0.05% Tween-20 (PBST), the plates were blocked with blocking buffer (5% nonfat dry milk in PBST) for one hour. Afterwards, 100 µl of each patient's serum sample (diluted 50-fold) was added in duplicate wells for 1.5 hours, followed by horseradish-peroxidase (HRP)-conjugated goat anti-human IgG (sc-2453, Santa Cruz Biotech) or HRP-conjugated goat anti-human IgA (Bio-Rad, Hercules, Calif.), and then TMB substrate (BD, San Diego, Calif.). For inter-plate standardization, 2 control samples were included with each assay.

In Vitro Citrullination Assay.

Human recombinant N-acetylglucosamine-6-sulfatase (2 µg) or filamin A (2 µg) were incubated with rhPAD-4 (400 ng), generously provided by Maximilian Koenig from the laboratory of Felipe Andrade, in 1 M Tris (pH 7.6) in presence of 200 mM CaCl2. A negative control reaction was performed substituting 200 mM CaCl2 with 200 mM EDTA. Incubation was performed at 3° C. for 3 hours. Protein citrullination was determined by anti-modified citrulline immunoblotting, according to the recommendations of the manufacturer (Millipore).

Quantification of GNS and FLNA Protein Levels in Serum and Joint Fluid.

ELISA plates were coated with 5 µg/ml capture antibody (sc-161669 for GNS, and sc-58764 for FLNA, Santa Cruz Biotech) overnight at 4° C. Plates were then washed with PBS and blocked with 5% milk PBST (blocking buffer) for one hour. Afterwards, serum or joint fluid samples (diluted 1:10 in blocking buffer) were added in duplicate and incubated for two hours at room temperature. Next, detection antibody (5 µg/ml) (SAB1410557 for GNS, Sigma; and sc-28284 for FLNA, Santa Cruz Biotech) was added for 2 hours. The plates were then incubated with goat anti-rabbit IgG-HRP (sc-2030, Santa Cruz Biotech), followed by TMB substrate. For inter-plate standardization, 2 control samples were included on each plate.

Immunohistochemistry.

Fresh frozen synovial tissue samples were stained for GNS and FLNA proteins. After blocking, the sections were incubated with rabbit polyclonal antibody against GNS (SAB1410557, Sigma-Aldrich) and with mouse monoclonal antibody against FLNA (sc-17749, Santa Cruz Biotech) at 4° C. overnight. For negative controls, non-specific rabbit or mouse IgG were used. The following day, the sections were incubated with biotinylated anti-rabbit or anti-mouse secondary antibody, peroxidase-streptavidin, and then, diaminobenzidine substrate. The slides were counterstained with Mayer's hemotoxylin and mounted with Permount. Microscopic images were obtained with a Zeiss widefield microscope.

In silico determinations of HLA-DR binding affinity. The affinity of HLA-DR binding of the GNS, FLNA, and related microbial peptides was determined using the T cell epitope—MHC class II molecules binding prediction tool from the Immune Epitope Database and Analysis resource (IEDB). This tool employs different methods to predict MHC Class II epitopes, including a consensus approach which combines NN-align, SMM-align and combinatorial library methods. For the analysis, all HLA-DR alleles found in the RA cohort were analyzed, including 5 shared-epitope alleles and 9 non-SE alleles.

Statistics.

Categorical data were analyzed by Fisher's exact test, and quantitative data were analyzed using unpaired t test with Welch correction. Correlations were sought using Spearman correlation test. All analyses were performed using GraphPad Prism 6. All P values were two-tailed. P values <0.05 were considered statistically significant.

REFERENCE EXAMPLE 2

1. Li Y, et al. Deficient activity of the nuclease MRE11A induces T cell aging and promotes arthritogenic effector functions in patients with rheumatoid arthritis. Immunity. 2016; 45(4):903-16.
2. Gregersen P K, Silver J, and Winchester R J. The shared epitope hypothesis. An approach to understanding the molecular genetics of susceptibility to rheumatoid arthritis. Arthritis Rheum. 1987; 30(11):1205-13.
3. McInnes I B, and Schett G. The pathogenesis of rheumatoid arthritis. N Engl J Med. 2011; 365(23):2205-19.
4. Nishimura K, et al. Meta-analysis: diagnostic accuracy of anti-cyclic citrullinated peptide antibody and rheumatoid factor for rheumatoid arthritis. Ann Intern Med. 2007; 146(11):797-808.
5. Schellekens G A, de Jong B A, van den Hoogen F H, van de Putte L B, and van Venrooij W J. Citrulline is an essential constituent of antigenic determinants recognized by rheumatoid arthritis-specific autoantibodies. J Clin Invest. 1998; 101(1):273-81.
6. Suzuki K, et al. High diagnostic performance of ELISA detection of antibodies to citrullinated antigens in rheumatoid arthritis. Scand J Rheumatol. 2003; 32(4):197-204.
7. del Puente A, Knowler W C, Pettitt D J, and Bennett P H. The incidence of rheumatoid arthritis is predicted by rheumatoid factor titer in a longitudinal population study. Arthritis Rheum. 1988; 31(10):1239-44.
8. Majka D S, et al. Duration of preclinical rheumatoid arthritis-related autoantibody positivity increases in subjects with older age at time of disease diagnosis. Ann Rheum Dis. 2008; 67(6):801-7.
9. Nielen M M, et al. Specific autoantibodies precede the symptoms of rheumatoid arthritis: a study of serial measurements in blood donors. Arthritis Rheum. 2004; 50(2):380-6.
10. Bachmaier K, Neu N, de la Maza L M, Pal S, Hessel A, and Penninger J M. Chlamydia infections and heart disease linked through antigenic mimicry. Science. 1999; 283(5406):1335-9.
11. Miller S D, et al. Persistent infection with Theiler's virus leads to CNS autoimmunity via epitope spreading. Nat Med. 1997; 3(10):1133-6.
12. Zhao Z S, Granucci F, Yeh L, Schaffer P A, and Cantor H. Molecular mimicry by herpes simplex virus-type 1: autoimmune disease after viral infection. Science. 1998; 279(5355):1344-7.
13. Scher J U, et al. Expansion of intestinal *Prevotella copri* correlates with enhanced susceptibility to arthritis. Elife. 2013; 2e01202.
14. Zhang X, et al. The oral and gut microbiomes are perturbed in rheumatoid arthritis and partly normalized after treatment. Nat Med. 2015; 21(8):895-905.
15. Maeda Y, et al. Dysbiosis contributes to arthritis development via activation of autoreactive T cells in the intestine. Arthritis Rheumatol. 2016; 68:2646-2661.
16. Hemmer B, et al. Predictable TCR antigen recognition based on peptide scans leads to the identification of agonist ligands with no sequence homology. J Immunol. 1998; 160(8):3631-6.
17. Horwitz M S, Bradley L M, Harbertson J, Krahl T, Lee J, and Sarvetnick N. Diabetes induced by Coxsackie virus: initiation by bystander damage and not molecular mimicry. Nat Med. 1998; 4(7):781-5.
18. Ehl S, et al. Viral and bacterial infections interfere with peripheral tolerance induction and activate CD8+ T cells to cause immunopathology. J Exp Med. 1998; 187(5):763-74.
19. Seward R J, Drouin E E, Steere A C, and Costello C E. Peptides presented by HLA-DR molecules in synovia of patients with rheumatoid arthritis or antibiotic-refractory Lyme arthritis. Mol Cell Proteomics. 2011; 10(3):M110 002477.
20. Wang Q, et al. Immunogenic HLA-DR-presented self-peptides identified directly from clinical samples of synovial tissue, synovial fluid, or peripheral blood in patients with rheumatoid arthritis or Lyme arthritis. J Proteome Res. 2016; 16:122-136.
21. Drouin E E, et al. A novel human autoantigen, endothelial cell growth factor, is a target of T and B cell responses in patients with Lyme disease. Arthritis Rheum. 2013; 65(1):186-96.
22. Crowley J T, et al. A highly expressed human protein, apolipoprotein B-100, serves as an autoantigen in a subgroup of patients with Lyme disease. J Infect Dis. 2015; 212:1841-50.
23. Crowley J T, et al. Matrix metalloproteinase-10 is a target of T and B cell responses that correlate with synovial pathology in patients with antibiotic-refractory Lyme arthritis. J Autoimmun. 2016; 69:24-37.
24. Pianta A, et al. Annexin A2 is a target of autoimmune T and B cell responses associated with synovial fibroblast proliferation in patients with antibiotic-refractory Lyme arthritis. Clin Immunol. 2015; 160(2):336-41.
25. Pianta A, et al. Evidence for immune relevance of *Prevotella copri*, a gut microbe, in patients with rheumatoid arthritis [published online ahead of print Oct. 18, 2016]. Arthritis Rheumatol. doi: 10.1002/art.40003.
26. Sturniolo T, et al. Generation of tissue-specific and promiscuous HLA ligand databases using DNA microarrays and virtual HLA class II matrices. Nat Biotechnol. 1999; 17(6):555-61.
27. Mikuls T R, et al. Periodontitis and *Porphyromonas gingivalis* in patients with rheumatoid arthritis. Arthritis Rheumatol. 2014; 66(5):1090-100.
28. Sievers F, et al. Fast, scalable generation of high-quality protein multiple sequence alignments using Clustal Omega. Mol Syst Biol. 2011; 7:539.
29. Yu C S, Lin C J, and Hwang J K. Predicting subcellular localization of proteins for Gram-negative bacteria by support vector machines based on n-peptide compositions. Protein Sci. 2004; 13(5):1402-6.
30. Arvikar S L, et al. Clinical correlations with *Porphyromonas gingivalis* antibody responses in patients with early rheumatoid arthritis. Arthritis Res Ther. 2013; 15(5): R109.
31. Benjdia A, Martens E C, Gordon J I, and Berteau O. Sulfatases and a radical S-adenosyl-L-methionine (AdoMet) enzyme are key for mucosal foraging and fitness of the prominent human gut symbiont, *Bacteroides thetaiotaomicron*. J Biol Chem. 2011; 286(29):25973-82.
32. Ulmer J E, et al. Characterization of glycosaminoglycan (GAG) sulfatases from the human gut symbiont *Bacteroides thetaiotaomicron* reveals the first GAG-specific bacterial endosulfatase. J Biol Chem. 2014; 289(35): 24289-303.
33. Coutinho A, Kazatchkine M D, and Avrameas S. Natural autoantibodies. Curr Opin Immunol. 1995; 7(6):812-8.
34. Dighiero G. Natural autoantibodies, tolerance, and autoimmunity. Ann N Y Acad Sci. 1997; 815:182-92.
35. Kroese F G, Butcher E C, Stall A M, Lalor P A, Adams S, and Herzenberg L A. Many of the IgA producing plasma cells in murine gut are derived from self-replenishing precursors in the peritoneal cavity. Int Immunol. 1989; 1(1):75-84.
36. Macpherson A J, Gatto D, Sainsbury E, Harriman G R, Hengartner H, and Zinkernagel R M. A primitive T cell-independent mechanism of intestinal mucosal IgA responses to commensal bacteria. Science. 2000; 288 (5474):2222-6.
37. Suzuki K, Ha S A, Tsuji M, and Fagarasan S. Intestinal IgA synthesis: a primitive form of adaptive immunity that regulates microbial communities in the gut. Semin Immunol. 2007; 19(2):127-35.
38. Kubinak J L, and Round J L. Do antibodies select a healthy microbiota? Nat Rev Immunol. 2016; 16(12):767-74.

39. Klareskog L, Ronnelid J, Lundberg K, Padyukov L, and Alfredsson L. Immunity to citrullinated proteins in rheumatoid arthritis. Annu Rev Immunol. 2008; 26:651-75.
40. Romero V, et al. Immune-mediated pore-forming pathways induce cellular hypercitrullination and generate citrullinated autoantigens in rheumatoid arthritis. Sci Transl Med. 2013; 5(209):209ra150.
41. Wang J Y, and Roehrl M H. Glycosaminoglycans are a potential cause of rheumatoid arthritis. Proc Natl Acad Sci USA. 2002; 99(22):14362-7.
42. Kim H, and McCulloch C A. Filamin A mediates interactions between cytoskeletal proteins that control cell adhesion. FEBS Lett. 2011; 585(1):18-22.
43. Feng Y, et al. Filamin A (FLNA) is required for cell-cell contact in vascular development and cardiac morphogenesis. Proc Natl Acad Sci USA. 2006; 103(52):19836-41.
44. Kuriya B, et al. Earlier time to remission predicts sustained clinical remission in early rheumatoid arthritis—results from the Canadian Early Arthritis Cohort (CATCH). J Rheumatol. 2014; 41(11):2161-6.
45. van Nies J A, Tsonaka R, Gaujoux-Viala C, Fautrel B, and van der Helm-van Mil A H. Evaluating relationships between symptom duration and persistence of rheumatoid arthritis: does a window of opportunity exist? Results on the Leiden early arthritis clinic and ESPOIR cohorts. Ann Rheum Dis. 2015; 74(5):806-12.
46. Aletaha D, et al. 2010 Rheumatoid arthritis classification criteria: an American College of Rheumatology/European League Against Rheumatism collaborative initiative. Arthritis Rheum. 2010; 62(9):2569-81.

The invention claimed is:

1. A method of treating Rheumatoid arthritis in a subject, the method comprising:
   (a) receiving the results of an assay that indicates that the subject is immunologically reactive with one or more *Prevotella copri* polypeptides comprising an amino acid sequence selected from the group consisting of: SEQ ID NO: 1, KRIILILTVLLAMLGQVAY (SEQ ID NO: 2), DYRGYWTMRYQFDSATVS (SEQ ID NO: 3), and EKINSLPTSSTGI (SEQ ID NO: 4); and then
   (b) administering to the subject a therapeutically effective amount of a disease modifying anti-rheumatic drug (DMARD).

2. The method of claim 1, wherein the assay detects an increase in the level of a T cell response to the *Prevotella copri* polypeptide compared with an appropriate control.

3. The method of claim 2, wherein the T cell response is a Th17 response.

4. The method of claim 2, wherein the assay in step (a) comprises:
   a. stimulating peripheral blood mononuclear cells (PBMC) of the subject or the synovial fluid mononuclear cells (SFMC) of the subject in vitro with the *Prevotella copri* polypeptide; and
   b. measuring T cell proliferation in vitro or secretion of IFN-γ into cell culture supernatants;
   c. identifying the subject as having T cells reactive the *Prevotella copri* polypeptide when T cell proliferation or secretion of IFN-γ is measured as significantly increased over that of an appropriate control.

5. The method of claim 1, wherein the assay is an enzyme-linked immunosorbent assay (ELISA), agglutination test, direct immunofluorescence assay, indirect immunofluorescence assay, or an immunoblot assay.

6. The method of claim 1, wherein prior to step (a), a biological sample is obtained from the subject from peripheral blood, synovial fluid, synovial tissue, peripheral blood mononuclear cells (PBMC), or synovial fluid mononuclear cells (SFMC).

7. The method of claim 1, wherein the subject exhibits symptoms of arthritis or other autoimmune related disease manifestation.

8. The method of claim 1, wherein the subject has or is suspected of having Rheumatoid arthritis.

9. The method of claim 1, wherein the subject is suspected of having or suffers from new onset rheumatoid arthritis or chronic rheumatoid arthritis.

10. The method of claim 1, wherein the subject has been further tested for one or more of rheumatoid factor (RF), anti-citrullinated protein antibodies (ACPA), *Prevotella* DNA in their synovial fluid, immunological reactivity to filamin-A, immunological reactivity to N-acetylglucosamine-6-sulfatase, and one or more HLA-DR alleles.

11. The method of claim 1, wherein the results of the assay indicates an increase in the level of immunocomplexes with one or more of a *Prevotella copri* polypeptides compared to an appropriate control sample.

12. The method of claim 1, further comprising receiving the results of an assay that indicates an increase in the level of IFNγ secretion and/or T cell proliferation following contact of a biological sample from the subject with one or more of a *Prevotella copri* polypeptide compared to an appropriate control sample.

13. The method of claim 1, wherein the subject has one or more HLA-DR alleles selected from the group consisting of: HLA-DRB*0101, HLA-DRB*0401, HLA-DRB*0405, and HLA-DRB*0408.

14. The method of claim 1, further comprising administering to the subject one or more of a nonsteroidal anti-inflammatory drug (NSAIDs), a steroid, a biologic, or an antibiotic.

\* \* \* \* \*